US009051564B2

(12) United States Patent
Higgins et al.

(10) Patent No.: US 9,051,564 B2
(45) Date of Patent: Jun. 9, 2015

(54) COMPOSITIONS FOR AND METHODS OF IDENTIFYING ANTIGENS

(75) Inventors: Darren E. Higgins, Jamaica Plain, MA (US); Michael N. Starnbach, Needham, MA (US); Todd Gierahn, Brookline, MA (US); Nadia R. Roan, San Francisco, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 1629 days.

(21) Appl. No.: 12/224,074

(22) PCT Filed: Feb. 21, 2007

(86) PCT No.: PCT/US2007/004675
§ 371 (c)(1),
(2), (4) Date: Jun. 17, 2010

(87) PCT Pub. No.: WO2007/098255
PCT Pub. Date: Aug. 30, 2007

(65) Prior Publication Data
US 2011/0076288 A1    Mar. 31, 2011

Related U.S. Application Data

(60) Provisional application No. 60/775,462, filed on Feb. 21, 2006, provisional application No. 60/817,471, filed on Jun. 29, 2006.

(51) Int. Cl.
C12N 15/10 (2006.01)
C07K 14/295 (2006.01)
C12Q 1/70 (2006.01)
C12Q 1/68 (2006.01)
A61K 38/00 (2006.01)
A61K 39/00 (2006.01)

(52) U.S. Cl.
CPC .............. *C12N 15/1034* (2013.01); *C12Q 1/70* (2013.01); *C12Q 1/68* (2013.01); *A61K 38/00* (2013.01); *A61K 39/00* (2013.01); *C07K 14/295* (2013.01); *C07K 2319/00* (2013.01)

(58) Field of Classification Search
None
See application file for complete search history.

(56) References Cited

U.S. PATENT DOCUMENTS

| 6,004,815 | A | 12/1999 | Portnoy et al. |
| 6,008,415 | A | 12/1999 | Greene et al. |
| 6,287,556 | B1 | 9/2001 | Portnoy et al. |
| 6,569,435 | B1 | 5/2003 | Punnonen et al. |
| 6,599,502 | B2 | 7/2003 | Portnoy et al. |
| 2002/0198162 | A1 | 12/2002 | Punnonen et al. |
| 2003/0202989 | A1 | 10/2003 | Collier et al. |
| 2003/0219752 | A1 | 11/2003 | Short |
| 2005/0106162 | A1 | 5/2005 | Grandi et al. |

OTHER PUBLICATIONS

Stemke-Hale et al. (Vaccine, 2005, 23:3016-3025).*
Novagen (pET System Manual 1999).*
(Continued)

*Primary Examiner* — Christopher M Babic
*Assistant Examiner* — Jeremy C Flinders
(74) *Attorney, Agent, or Firm* — Clark & Elbing LLP; Kristina Bieker-Brady

(57) ABSTRACT

Replicable libraries having discrete members in defined locations for screening for antigens to a pathogenic organism are provided. Also provided are methods for using such libraries as well as a specific antigen, CT788, which induces T-cell activation during a *Chlamydia* infection.

19 Claims, 26 Drawing Sheets

(56) References Cited

OTHER PUBLICATIONS

Adu-Bobie et al. (Vaccine, 2003, 21:605-610).*
Tscharke et al. (The Journal of Experimental Medicine, 2005, 1:95-104).*
Rogozin et al. (Nucleic Acids Research, 2002, 30:4264-4271).*
Kitawaga et al., "Complete set of ORF clones of *Escherichia coli* Aska library (A Complete Set of *E. coli* K-12 ORF Archive): Unique Resources for Biological Research," DNA Res. 12(5):291-9 (2005).
Patent Examination Report No. 2 for Australian Patent Application No. 2007217515, issued Jan. 9, 2014 (15 pages).
Extended European Search Report for European Patent Application No. 12006532.1, dated Oct. 23, 2012 (6 pages).
Balomenos et al., "Incomplete T cell receptor V beta allelic exclusion and dual V beta-expressing cells," *J. Immunol.* 155(7): 3308-3312 (1995).
Beatty et al., "Persistent chlamydiae: from cell culture to a paradigm for chlamydial pathogenesis," *Microbiol. Rev.* 58(4): 686-699 (1994).
Bendtsen et al., "Improved prediction of signal peptides: SignalP 3.0," *J. Mol. Biol.* 340(4): 783-795 (2004).
Bouwer et al., "Directed antigen delivery as a vaccine strategy for an intracellular bacterial pathogen," *Proc. Natl. Acad. Sci. USA* 103(13): 5102-5107 (2006).
Buchholz et al., "Presentation without proteolytic cleavage of endogenous precursors in the MHC class I antigen processing pathway," *J. Biol. Chem.* 270(12): 6515-6522 (1995).
Butz et al., "Massive expansion of antigen-specific CD8+ T cells during an acute virus infection," *Immunity.* 8(2): 167-175 (1998).
Cain et al., "Local Th1-like responses are induced by intravaginal infection of mice with the mouse pneumonitis biovar of *Chalmydia trachomatis*," *Infect. Immunol.* 63(5): 1784-1789 (1995).
Carlson et al., "Comparative genomic analysis of *Chlamydia trachomatis* oculotropic and genitotropic strains," *Infect. Immun.* 73(10): 6407-6418 (2005).
Chen et al., "Genetic fusion of proteins to the SIV Tat protein enhances their immunogenicity," *Vaccine* 24(6): 708-715 (2006).
Cochran et al., "The relationship of MHC-peptide binding and T cell activation probed using chemically defined MHC class II oligomers," *Immunity* 12(3): 241-250 (2000).
Coles et al., "Progression of armed CTL from draining lymph node to spleen shortly after localized infection with herpes simplex virus 1," *J. Immunol.* 168(2): 834-838 (2002).
Critchley et al., "Potential therapeutic applications of recombinant, invasive *E. coli*," *Gene Ther.* 11(15): 1224-1233 (2004).
Fan et al., "Immunological properties of recombinant *Mycobacterium bovis* bacillus Calmette-Guérin strain expressing fusion protein IL-2-ESAT-6," *Acta. Biochim. Biophys. Sin.* 38(10): 683-690 (2006).
Fling et al., "CD8+ T cells recognize an inclusion membrane-associated protein from the vacuolar pathogen *Chlamydia trachomatis*," *Proc. Natl. Acad. Sci. USA* 98(3): 1160-1165 (2001).
Gallichan et al., "Long-lived cytotoxic T lymphocyte memory in mucosal tissues after mucosal but not systemic immunization," *J. Exp. Med.* 184(5): 1879-1890 (1996).
Goodall et al., "Identification of *Chlamydia trachomatis* antigens recognized by human CD4+ T lymphocytes by screening an expression library," *Eur. J. Immunol.* 31(5): 1513-1522 (2001).
Hassell et al., "Identification of T-cell stimulatory antigens of *Chlamydia trachomatis* using synovial fluid-derived T-cell clones," *Immunology* 79(4): 513-519 (1993).
Hawkins et al., "Expression of mucosal homing receptor α4β7 is associated with enhanced migration to the Chalmydia-infected murine genital mucosa in vivo," *Infect. Immunol.* 68(10): 5587-5594 (2000).
Hawkins et al., "A *Chlamydia trachomatis*-specific Th2 clone does not provide protection against a genital infection and displays reduced trafficking to the infected genital mucosa," *Infect. Immunol.* 70(9): 5132-5139 (2002).
Higgins et al., "Delivery of protein to the cytosol of macrophages using *Escherichia coli* K-12," *Mol. Microbiol.* 31(6): 1631-1641 (1999).
Hogan et al., "Chlamydial persistence: beyond the biphasic paradigm," *Infect. Immunol.* 72(4): 1843-1855 (2004).
Hu et al., "*Escherichia coli* expressing recombinant antigen and listeriolysin O stimulate class I-restricted CD8+ T cells following uptake by human APC," *J. Immunol.* 172(3): 1595-1601 (2004).
Huleatt et al., "Vaccination with recombinant fusion proteins incorporating Toll-like receptor ligands induces rapid cellular and humoral immunity," *Vaccine* 25(4): 763-775 (2007).
Inglis et al., "Isolation of two cDNAs encoding novel alpha 1-antichymotrypsin-like proteins in a murine chondrocytic cell line," *Gene.* 1062(2): 213-220 (1991).
Karttunen et al., "Detection of rare antigen-presenting cells by the *lacZ* T-cell activation assay suggests an expression cloning strategy for T-cell antigens," *Proc. Natl. Acad. Sci. USA* 89(13): 6020-6024 (1992).
Kinnunen et al., "*Chlamydia trachomatis* heat shock protein-60 induced interferon-gamma and interleukin-10 production in infertile women," *Clin. Exp. Immunol.* 131(2): 299-303 (2003).
Kouskoff et al., "Cassette vectors directing expression of T cell receptor genes in transgenic mice," *J. Immunol. Methods* 180(2): 273-280 (1995).
Lee et al., "The prolonged half-lives of new erythropoietin derivatives via peptide addition," *Biochem. Biophys. Res. Commun.* 339(1): 380-385 (2006).
Li et al., "Magic, an in vivo genetic method for the rapid construction of recombinant DNA molecules," *Nat. Genet.* 37(3): 311-319 (2005).
Liolios et al., "The Genomes on Line Database (GOLD) v.2: a monitor of genome projects worldwide," *Nucleic Acids Res* 34(Database issue): D332-334 (2006).
Loomis et al., "T cell responses to *Chlamydia trachomatis*," *Curr. Opin. Microbiol.* 5(1): 87-91, (2002).
McSorley et al., "Tracking salmonella-specific CD4 T cells in vivo reveals a local mucosal response to a disseminated infection," *Immunity* 16(3): 365-377 (2002).
Miao et al., "Characterization of gene expression in recombinant *Escherichia coli* cells infected with phage lambda," *Biotechnol. Prog.* 9(2): 153-159 (1993).
Moutaftsi et al., "A consensus epitope prediction approach identifies the breadth of murine T(CD8+)-cell responses to vaccinia virus," *Nat. Biotechnol.* 24(7): 817-819 (2006).
Murby et al., "Hydrophobicity engineering to increase solubility and stability of a recombinant protein from respiratory syncytial virus," *Eur. J. Biochem.* 230(1): 38-44 (1995).
Nandi et al., "Characterization of neutrophils and T lymphocytes associated with the murine vaginal epithelium," *Reg. Immunol.* 5(6): 332-338 (1993).
Pape et al., "Use of adoptive transfer of T-cell-antigen-receptor-transgenic T cell for the study of T-cell activation in vivo," *Immunol. Rev.* 156: 67-78 (1997).
Parr et al., "Antigen recognition in the female reproductive tract: I. Uptake of intraluminal protein tracers in the mouse vagina," *J. Reprod. Immunol.* 17(2): 101-114 (1990).
Parr et al., "Langerhans cells and T lymphocyte subsets in the murine vagina and cervix," *Biol. Reprod.* 44(3): 491-498 (1991).
Perry et al., "Distinct homing pathways direct T lymphocytes to the genital and intestinal mucosae in Chlamydia-infected mice," *J. Immunol.* 160(6): 2905-2914 (1998).
Perry et al., "Chlamydial colonization of multiple mucosae following infection by any mucosal route," *Infect. Immunol.* 67(7): 3686-3689 (1999).
Portnoy et al., "Role of hemolysin for the intracellular growth of *Listeria monocytogenes*," *J. Exp. Med.* 167(4): 1459-1471 (1988).
Radford et al., "A recombinant *E. coli* vaccine to promote MHC class I-dependent antigen presentation: application to cancer immunotherapy," *Gene Ther.* 9(21): 1455-1463 (2002).
Radford et al., "Recombinant *E. coli* efficiently delivers antigen and maturation signals to human dendritic cells: presentation of MART1 to CD8+ T cells," *Int. J. Cancer* 105(6): 811-819 (2003).

(56) References Cited

OTHER PUBLICATIONS

Ramsey et al., "Prior genital tract infection with a murine or human biovar of *Chlamydia trachomatis* protects mice against heterotypic challenge infection," *Infect. Immunol.* 67(6): 3019-3025 (1999).

Rasmussen et al., "*Listeria monocytogenes* isolates can be classified into two major types according to the sequence of the listeriolysin gene," *Infect. Immun.* 59(11): 3945-3951 (1991).

Reche et al., "Enhancement to the RANKPEP resource for the prediction of peptide binding to MHC molecules using profiles," *Immunogenetics* 56(6): 405-419 (2004).

Roan et al., "Monitoring the T cell response to genital tract infection," *Proc. Natl. Acad. Sci. USA.* 103(32): 12069-12074 (2006).

Roman et al., "CD4 effector T cell subsets in the response to influenza: heterogeneity, migration, and function," *J. Exp. Med.* 196(7): 957-968 (2002).

Rott et al., "A fundamental subdivision of circulating lymphocytes defined by adhesion to mucosal addressin cell adhesion molecule-1. Comparison with vascular cell adhesion molecule-1 and correlation with beta 7 integrins and memory differentiation," *J. Immunol.* 156(10): 3727-3736 (1996).

Rottenberg et al., "The role of IFN-gamma in the outcome of chlamydial infection," *Curr. Opin. Immunol.* 14(4): 444-451 (2002).

Sanderson et al., "Identification of a CD4+ T cell stimulating antigen of pathogenic bacteria by expression cloning," *J. Exp. Med.* 182(6): 1751-1757 (1995).

Sano et al., "Swift development of protective effector functions in naïve CD8(+) T cells against malaria liver stages," *J. Exp. Med.* 194(2): 173-179 (2001).

Sato et al., "Immunostimulatory DNA sequences necessary for effective intradermal gene immunization," *Science* 273(5273): 352-354 (1996).

Schulze et al., "The FAI protein of group C streptococci targets B-cells and exhibits adjuvant activity," *Vaccine* 23(11): 1408-1413 (2005).

Shaw et al., "Stimulation of CD8+ T cells following diphtheria toxin-mediated antigen delivery into dendritic cells," *Infect. Immun.* 74(2): 1001-1008 (2006).

Sinclair et al., "Glycoengineering: the effect of glycosylation on the properties of therapeutic proteins," *J. Pharm. Sci.* 94(8): 1626-1635 (2005).

Starnbach et al., "Protective cytotoxic T lymphocytes are induced during murine infection with *Chlamydia trachomatis*," J. Immunol. 153(11): 5183-5189 (1994).

Starnbach et al., "Murine cytotoxic T lymphocytes induced following *Chlamydia trachomatis* intraperitoneal or genital tract infection respond to cells infected with multiple serovars," *Infect. Immunol.* 63(9): 3527-3530 (1995).

Starnbach et al., "An inclusion membrane protein from *Chlamydia trachomatis* enters the MHC class I pathway and stimulates a CD8+ T cell response," *J. Immunol.* 171(9): 4742-4749 (2003).

Steele et al., "Hematopoietic cells are required to initiate a *Chlamydia trachomatis*-specific CD8+ T cell response," *J. Immunol.* 173(10): 6327-6337 (2004).

Stephens et al., "Genome sequence of an obligate intracellular pathogen of humans: *Chlamydia trachomatis*," Science 282(5389): 754-759 (1998).

Swain et al., "Regulation of memory CD4 T cells: generation, localization and persistence," *Adv. Exp. Med. Bio.* 512: 113-120 (2002).

Tough et al., "Viruses and T cell turnover: evidence for bystander proliferation," *Immunol. Rev.* 150: 129-142 (1996).

Tuffrey et al., "Salpingitis in mice induced by human strains of *Chlamydia trachomatis*," *Br. J. Exp. Pathol.* 67(4): 605-616 (1986).

Tuffrey et al., "Severity of salpingitis in mice after primary and repeated inoculation with a human strain of *Chlamydia trachomatis*," *J. Exp. Pathol.* 71(3): 403-410 (1990).

Ulmer et al., "Vaccine manufacturing: challenges and solutions," *Nat. Biotechnol.* 24(11): 1377-1383 (2006).

Vedadi et al., "Genome-scale protein expression and structural biology of *Plasmodium falciparum* and related Apicomplexan organisms," *Mol. Biochem. Parasitol.* 151(1): 100-110 (2007).

Villareal et al., "Persistent Chlamydiae and chronic arthritis," *Arthritis. Res.* 4(1): 5-9 (2002).

von Boehmer, "Developmental biology of T cells in T cell-receptor transgenic mice," *Annu. Rev. Immunol.* 8: 531-556 (1990).

Walhout et al., "Gateway recombinational cloning: application to the cloning of large numbers of open reading frames or ORFeomes," *Methods Enzymol.* 328: 575-592 (2000).

Weinberg et al., "Selective depletion of myelin-reactive T cells with the anti-OX-40 antibody ameliorates autoimmune encephalomyelitis," *Nat. Med.* 2(2): 183-9 (1996).

Wizel et al., "Multiple *Chlamydia pneumonia* antigens prime CD8+ Tc1 responses that inhibit intracellular growth of this vacuolar pathogen," *J. Immunol.* 169(5): 2524-2535 (2002).

Yang et al., "Induction of alloreactive cytotoxic T cells by acute virus infection of mice," *J. Immunol.* 136(4): 1186-1193 (1986).

Ziegler et al., "The activation antigen CD69," *Stem Cells* 12(5): 456-465 (1994).

International Search Report and Written Opinion for International Application No. PCT/US07/04675, dated Sep. 17, 2008.

Supplementary European Search Report for International Application No. PCT/US07/04675, dated Apr. 19, 2010.

* cited by examiner

CT788 protein
  1 mnsgmfpftf fllyiclgml taylankknr nligwflagm ffgifaiifl lilpplpsst
 61 qdnrsmdqqd seefllqntl edseiisipd tmnqiaidte kwfylnkdyt nvgpisivql
121 taflkeckhs pekgidpqel wvwkkgmpnw ekvknipels gtvkde CT788$_{133-152}$ or Ctal$_{133-152}$ kgidpqelwvwkkgmpnwek

Figure 14

COMPOSITIONS FOR AND METHODS OF IDENTIFYING ANTIGENS

CROSS-REFERENCE TO RELATED APPLICATIONS

This application is the national stage of International Application No. PCT/US2007/004675, filed Feb. 21, 2007, which in turn, claims benefit of U.S. Application No. 60/817,471, filed Jun. 29, 2006, and U.S. Application No. 60/775,462, filed Feb. 21, 2006.

STATEMENT AS TO FEDERALLY FUNDED RESEARCH

This invention was made with Government support under the National Institutes of Health awards AI039558 and AI055900. The Government has certain rights in the invention.

INCORPORATION BY REFERENCE OF A SEQUENCE LISTING FILED ELECTRONICALLY

Kindly incorporate the .txt file Sequence Listing, submitted Nov. 16, 2010, having the name 00742_192003_Sequence_Listing.txt, file size 30.2 kB, created on Nov. 10, 2010.

BACKGROUND OF THE INVENTION

Excitement around vaccine technologies has renewed over the past few years, driven by the emergence of new disease threats to humanity, the reemergence of previously curable diseases in the Western World such as TB, the threat of bioterrorism, and increasing evidence that cancers can be treated by vaccination, as long as the right antigens can be found. Infectious diseases still remain as one of the leading causes of morbidity and mortality worldwide, killing more than 13 million young adults and children annually. TB alone is responsible for 2 million deaths annually, while it is estimated that combined over 3 million individuals die from malaria and AIDS each year. New emerging or reemerging infectious diseases, such as SARS or Avian flu, also pose a continual threat to global world health. Many infectious diseases, such as malaria, TB, AIDS, SARS, and influenza are caused by intracellular pathogens that are capable of growing and spreading directly within human cells. Because intracellular pathogens grow sequestered within host cells, the humoral (antibody) immune response is often ineffective in generating protective immunity.

When they work, vaccines are one of the most effective ways of preventing and treating disease. Unfortunately, many research and clinical vaccine programs have a low probability of success because, prior to the present invention, there was no way to screen all possible antigens or predict which ones will be effective.

Thus, there is a need for new strategies to develop effective vaccines for the treatment of infectious diseases and cancer.

SUMMARY OF THE INVENTION

In a first aspect, the present invention provides a replicable library including at least 20 (e.g., 30, 40, 50, 60, 70, 80, 90, 100, 125, 150, 200, 300, 400, 500, 600, 700, 800, 900, 1000, 1200, 1500, 2000, 2500, 3000, 4000, or 5000) discrete members in defined locations, where (a) the members of the library each include a cell or virus including a first polynucleotide encoding at least a portion of a polypeptide encoded by the genome of a pathogenic organism other than the cell or the virus, the first polynucleotide operably linked to a promoter, and (b) the library includes polynucleotides encoding a portion of at least 10% (e.g., 20%, 30%, 40%, 50%, 60%, 70%, 80%, 90%, 95%, 98%, or 99%) of the polypeptides encoded by the genome (i.e., of the proteome) of the pathogenic organism.

In a related second aspect, the invention provides a replicable library including at least 10 (e.g., 15, 20, 30, 40, 50, 60, 70, 80, 90, 100, 125, 150, 200, 300, 400, 500, 600, 700, 800, 900, 1000, 1200, 1500, 2000, 2500, 3000, 4000, or 5000) discrete members in defined locations, where (a) the members of the library each include a cell or virus including a first polynucleotide encoding at least a portion of a polypeptide encoded by the genome of a pathogenic organism other than the cell or virus, the first polynucleotide operably linked to a promoter, (b) the members each include fewer than 24 (e.g., 23, 22, 21, 20, 19, 18, 17, 16, 15, 14, 13, 12, 11, 10, 9, 8, 7, 6, 5, 4, 3, or 2) different polynucleotides each encoding at least a portion of a polypeptide encoded by the genome of a pathogenic organism, and (c) the library includes polynucleotides encoding at least 10% (e.g., 20%, 30%, 40%, 50%, 60%, 70%, 80%, 90%, 95%, 98%, or 99%) of at least portions of the polypeptides encoded by the genome (i.e., of the proteome) of the pathogenic organism.

In either of the first two aspects of the invention, the portion of the polypeptide may have at least 50%, 60%, 70%, 80%, 90%, 93%, 95%, 98%, or 99% sequence identity to the corresponding portion of the polypeptide encoded by the genome of the pathogenic organism. Further, each member of the library may include a single polynucleotide encoded by the genome of the pathogenic organism. Finally, the pathogenic organism may be a bacterium, a virus, or a fungus.

In a third aspect, the invention provides a replicable library including at least 10 (e.g., 15, 20, 30, 40, 50, 60, 70, 80, 90, 100, 125, 150, 200, 300, 400, 500, 600, 700, 800, 900, 1000, 1200, 1500, 2000, 2500, 3000, 4000, or 5000) discrete members, where the members each include a first cell or virus including a polynucleotide encoding a polypeptide, or a portion or a fragment thereof, differentially expressed within a neoplastic cell as compared to the corresponding normal cell, the polynucleotide operably linked to a promoter, and the library includes polynucleotides encoding at least portions of 5% (e.g., 10%, 20%, 30%, 40%, 50%, 60%, 70%, 80%, 90%, 95%, or 99%) of the polypeptides differentially expressed within the neoplastic cell as compared to the corresponding normal cell. The portion of the polypeptide may have at least 50%, 60%, 70%, 80%, 90%, 93%, 95%, 98%, or 99% sequence identity to the corresponding portion of the polypeptide expressed in neoplastic cell. Each member of the library may contain fewer than 50, 40, 30, 20, 15, 14, 13, 12, 11, 10, 9, 8, 7, 6, 5, 4, 3, or 2 polynucleotides each encoding a portion of a different polypeptide differentially expressed in the neoplastic cell.

In any of the above three aspects, the virus may be a phage. The cell or first cell may be a bacterium (e.g., *E. coli*). The bacterium or virus may further include a second polynucleotide encoding a polypeptide, such as a pore-forming protein (e.g., LLO), not naturally expressed in the bacterium. Alternatively, the first polynucleotide may further encode a second polypeptide such as a pore-forming protein (e.g., LLO). Each of the first polynucleotides may further include a first tag sequence, where each of the polynucleotides encode a fusion protein including the first tag and the portion of the polypeptide. Each polynucleotide may further include a second tag sequence. The promoter may be an inducible promoter (e.g., a T7 promoter).

In a fourth aspect, the invention provides a method of determining whether a polypeptide is immunogenic which includes the steps of (a) individually contacting each member of the library of any of the above aspects with a second cell (e.g., a macrophage) capable of (i) endocytosing the cell or the virus in each member and (ii) displaying a peptide on its surface through the MHC class I pathway, where each member of the library includes the polypeptide encoded by the polynucleotide, (b) individually contacting each member of step (a) with a CTL cell (e.g., a plurality of CTL cells) derived from a mammal previously infected with the pathogenic organism or a mammal having or having previously had a neoplasm; and (c) detecting whether the CTL cell is activated, where activation of the CTL cell determines whether the polypeptide contained in the member is immunogenic. Each member of the library may include a polynucleotide encoding a pore-forming protein (e.g., LLO). Each member of the library may be killed prior to the contacting step (a). Prior to the contacting step (b), the second cell may be killed. The method may further include a step (d) recovering the polynucleotide encoding the polypeptide identified in step (c) from a replica copy of the library or may include a step, prior to contacting step (a), making a replica of the library. The method may further include performing the method steps (b) and (c) at least one (e.g., 2, 3, 4, 5, 7, 10, or 15) further time or times using the library, which may involve using a different CTL (e.g., a plurality of CTL cells) each time steps (b) and (c) are performed. In another embodiment, the method may include step (d) identifying an epitope sufficient for CTL activation within the polypeptide determined to be immunogenic in step (c).

In a fifth aspect, the invention also provides compositions (e.g., pharmaceutical compositions or vaccines) including at least one (e.g., 2, 3, 4, 5, 6, 7, 8, 10, 15, 20, 25, 30, 40, or 50) epitope or polypeptide identified using the fourth aspect of the invention. The compositions may further include a pharmaceutically acceptable carrier.

In a sixth aspect, the invention features compositions and methods related to the discovery of the CT788 polypeptide (SEQ ID NO:1) as an immunogenic protein in *Chlamydia* infection and identification of $CT788_{133-152}$ (SEQ ID NO:2) as antigenic epitope. Based on this discovery, the invention features a purified or recombinant polypeptide including CT788 polypeptide (e.g., a CT788 polypeptide or a fusion protein including a CT788 polypeptide), a composition including polypeptide including a CT788 polypeptide (e.g., a. CT788 polypeptide or a fusion protein including a CT788 polypeptide), and a purified or recombinant polypeptide including a fragment of a CT788 polypeptide (e.g., where the fragment is immunogenic or a fusion protein of said fragment) such as KGIDPQELWVWKKGMPNWEK (SEQ ID NO:2) or including a fragment having an amino acid sequence selected from the group consisting of the sequences listed in Table 1 (e.g., an immunogenic fragment listed in Table 1). Also featured is a composition including a polypeptide including a fragment of a CT788 polypeptide (e.g., an immunogenic fragment) such as KGIDPQELWVWKKG-MPNWEK (SEQ ID NO:2) or including a fragment having an amino acid sequence selected from the group consisting of the sequences listed in Table 1 (e.g., an immunogenic fragment listed in Table 1). The CT788 polypeptide or fragment thereof may contain at least 1, 2, 3, 4, 5, 8, 10, 15 or more additional amino acids at either the N-terminal or C-terminus of the molecule.

TABLE 1

Fragments of $Ctal_{133-152}$ (including SEQ ID NOS: 3-154)

| | | | | | | |
|---|---|---|---|---|---|---|
| KGI | GMP | WKKG | VWKKG | WVWKKG | WVWKKGM | VWKKGMPN |
| GID | MPN | KKGM | WKKGM | VWKKGM | VWKKGMP | WKKGMPNW |
| IDP | PNW | KGMP | KKGMP | WKKGMP | WKKGMPN | KKGMPNWE |
| DPQ | NWE | GMPN | KGMPN | KKGMPN | KKGMPNW | KGMPNWEK |
| PQE | WEK | MPNW | GMPNW | KGMPNW | KGMPNWE | KGIDPQELW |
| QEL | KGID | PNWE | MPNWE | GMPNWE | GMPNWEK | GIDPQELWV |
| ELW | GIDP | NWEK | PNWEK | MPNWEK | KGIDPQEL | IDPQELWVW |
| LWV | IDPQ | KGIDP | KGIDPQ | KGIDPQE | GIDPQELW | DPQELWVWK |
| WVW | DPQE | GIDPQ | GIDPQE | GIDPQEL | IDPQELWV | PQELWVWKK |
| VWK | PQEL | IDPQE | IDPQEL | IDPQELW | DPQELWVW | QELWVWKKG |
| WKK | QELW | DPQEL | DPQELW | DPQELWV | PQELWVWK | ELWVWKKGM |
| KKG | ELWV | PQELW | PQELWV | PQELWVW | QELWVWKK | LWVWKKGMP |
| KGM | LWVW | QELWV | QELWVW | QELWVWK | ELWVWKKG | WVWKKGMPN |
| | WVWK | ELWVW | ELWVWK | ELWVWKK | LWVWKKGM | VWKKGMPNW |
| | VWKK | LWVWK | LWVWKK | LWVWKKG | WVWKKGMP | WKKGMPNWE |
| | | WVWKK | | | | KKGMPNWEK |
| KGIDPQELWV | VWKKGMPNWE | | WVWKKGMPNWE | | LWVWKKGMPNWE | |
| GIDPQELWVW | WKKGMPNWEK | | VWKKGMPNWEK | | WVWKKGMPNWEK | |
| IDPQELWVWK | KGIDPQELWVW | | KGIDPQELWVWK | | KGIDPQELWVWKK | |
| DPQELWVWKK | GIDPQELWVWK | | GIDPQELWVWKK | | GIDPQELWVWKKG | |
| PQELWVWKKG | IDPQELWVWKK | | IDPQELWVWKKG | | IDPQELWVWKKGM | |
| QELWVWKKGM | DPQELWVWKKG | | DPQELWVWKKGM | | DPQELWVWKKGMP | |
| ELWVWKKGMP | PQELWVWKKGM | | PQELWVWKKGMP | | PQELWVWKKGMPN | |
| LWVWKKGMPN | QELWVWKKGMP | | QELWVWKKGMPN | | QELWVWKKGMPNW | |
| WVWKKGMPNW | ELWVWKKGMPN | | ELWVWKKGMPNW | | ELWVWKKGMPNWE | |
| | LWVWKKGMPNW | | | | LWVWKKGMPNWEK | |
| KGIDPQELWVWKKG | | | KGIDPQELWVWKKGMP | | | |
| GIDPQELWVWKKGM | | | GIDPQELWVWKKGMPN | | | |
| IDPQELWVWKKGMP | | | IDPQELWVWKKGMPNW | | | |
| DPQELWVWKKGMPN | | | DPQELWVWKKGMPNWE | | | |
| PQELWVWKKGMPNW | | | PQELWVWKKGMPNWEK | | | |
| QELWVWKKGMPNWE | | | KGIDPQELWVWKKGMPN | | | |
| ELWVWKKGMPNWEK | | | GIDPQELWVWKKGMPNW | | | |
| KGIDPQELWVWKKGM | | | IDPQELWVWKKGMPNWE | | | |
| GIDPQELWVWKKGMP | | | DPQELWVWKKGMPNWEK | | | |

TABLE 1-continued

| Fragments of $Cta1_{133-152}$ (including SEQ ID NOS: 3-154) | |
|---|---|
| IDPQELWVWKKGMPN | KGIDPQELWVWKKGMPNW |
| DPQELWVWKKGMPNW | GIDPQELWVWKKGMPNWE |
| PQELWVWKKGMPNWE | IDPQELWVWKKGMPNWEK |
| QELWVWKKGMPNWEK | KGIDPQELWVWKKGMPNWE |
| | GIDPQELWVWKKGMPNWEK |

The invention also features pharmaceutical and vaccine compositions. In one embodiment, the invention features a pharmaceutical composition including a polypeptide including a CT788 polypeptide or including a fragment of a CT788 polypeptide (e.g., an immunogenic fragment such as those described above) and a pharmaceutically acceptable carrier. The pharmaceutical composition may be formulated for administration by any means known in the art such as those described herein (e.g., oral or parenteral). In another embodiment, the invention features a vaccine including a polypeptide including a CT788 polypeptide or including a fragment of a CT788 polypeptide (e.g., an immunogenic fragment such as those described above), and a pharmaceutically acceptable carrier. The vaccine may further include an adjuvant (e.g., those described herein) and may be formulated for administration by any means known in the art such as those described herein (e.g., oral or parenteral). In any of the above embodiments of the sixth aspect, the polypeptide may have the sequence of a CT788 polypeptide or the sequence of a CT788 fragment (e.g., those shown in Table 1 and in Table 2). A polypeptide of the invention may be a fusion protein. Fusion proteins may include a tag useful in purification, e.g., GST, His, or myc, or may include an protein from an immune molecule (e.g., an Ig protein such as IgG, IgM, IgA, or IgE or an Fc region of an Ig protein), or any tag described herein or known in the art.

The invention also features methods for treating or preventing an infection (e.g., a bacterial infection such as a *Chlamydia* infection) in an individual (e.g., an individual in need of such treatment). The method includes administering (e.g., in an amount sufficient to prevent or treat said bacterial infection) to an individual a CT788 polypeptide or fragment thereof (e.g., an immunogenic fragment such as those described above). The administered CT788 polypeptide or fragment thereof may be purified polypeptide or fragment thereof.

By "portion" or "fragment" of a polypeptide is meant at least 5, 6, 7, 8, 9, 10, 15 20, 30, 50, 100, 200, 300, or 500 amino acids of the polypeptide. A fragment or portion may include 5%, 10%, 20%, 30%, 40%, 50%, 60%, 70%, 80%, 90%, 95%, or even 100% of the full length polypeptide (e.g., the polypeptide coded for by the genome of an organism).

By "operably linked" is meant that a nucleic acid molecule and one or more regulatory sequences (e.g., a promoter) are connected in such a way as to permit expression and/or secretion of the product (i.e., a polypeptide) of the nucleic acid molecule when the appropriate molecules (e.g., transcriptional activator proteins) are bound to the regulatory sequences.

By "polypeptide encoded by the genome of a pathogenic organism" is meant a polypeptide having at least 50%, 60%, 70%, 80%, 90%, 95%, 96%, 97%, 98%, 99%, or even 100% sequence identity to the polypeptide encoded by the pathogenic organism.

By "pathogenic organism" is meant any organism capable of infecting a mammal. Exemplary pathogenic organisms are bacteria, viruses, protozoa, and fungi and include the organisms described herein. In the context of the present invention, "pathogenic organism" additionally refers to an organism other than a cell or virus included in a library of the invention.

By "pore-forming protein" is meant any polypeptide, when contacted to a lipid bilayer membrane, which is capable of forming a channel or pore in the membrane. The pore or channel can allow passage of a molecule such as an ion, a polypeptide or a fragment thereof, or a polynucleotide, to pass through the membrane.

By "LLO" is meant listeriolysin O, or any fragment or variant thereof (e.g., a polypeptide substantially identical to the LLO sequence) capable of forming a pore in a eukaryotic membrane.

By "a cell capable of endocytosing" is a cell meant having the ability to internalize a particle such as a cell, virus, or macromolecule into a membrane-bound compartment.

By "differentially expressed" meant an increase in expression of at least 5%, 10%, 25%, 50%, 75%, 100%, 150%, 250%, 500%, or 1000% of expression in a test cell (e.g., a neoplastic cell) as compared to a corresponding control cell.

By "CT788 polypeptide" is meant a polypeptide with at least 40%, 50%, 60%, 70%, 80%, 90%, 95%, 99%, or even 100% identity to the sequence shown in FIG. 14, and having the ability to stimulate an immune response in an organism previously infected with *Chlamydia.*

By "tag sequence" is meant any sequence used to form of fusion protein (e.g., including a fragment or portion of a polypeptide described herein). Exemplary tags include FLAG, His (e.g., $His_6$), hemagglutinin (HA), Myc, glutathione S-transferase (GST), or any other tag known in the art. A tag sequence may be present at either the N- or C-terminus of the protein.

By a "purified polypeptide" or "isolated polypeptide" is meant a polypeptide that has been separated from components which naturally accompany it. Typically, the polypeptide is substantially pure when it is at least 30%, by weight, free from the proteins and naturally-occurring organic molecules with which it is naturally associated. In certain embodiments, the preparation is at least 50%, 60%, 75%, 85%, 90%, 95%, 96%, 97%, 98%, or 99% by weight, free from molecules with which it is naturally associated. A purified polypeptide may be obtained, for example, by extraction from a natural source; by expression of a recombinant polynucleotide encoding such a polypeptide; or by chemically synthesizing the polypeptide. Purity can be measured by any appropriate method, for example, column chromatography, polyacrylamide gel electrophoresis, or by HPLC analysis.

By "substantially identical" is meant a polypeptide or nucleic acid exhibiting at least 50%, 75%, 85%, 90%, 95%, or even 99% identity to a reference amino acid (e.g., CT788) or nucleic acid sequence. For polypeptides, the length of comparison sequences will generally be at least 7 amino acids (e.g., 20 amino acids), preferably at least 30 amino acids, more preferably at least 40 amino acids, and most preferably 50 amino acids, or full-length. For nucleic acids, the length of comparison sequences will generally be at least 20 nucleotides (e.g., 60 nucleotides), preferably at least 90 nucleotides, and more preferably at least 120 nucleotides, or full length.

Another indication that nucleotide sequences are substantially identical is if two molecules hybridize to each other under stringent conditions. Stringent conditions are sequence-dependent and will be different in different circumstances. Generally, stringent conditions are selected to be about 5° C. to about 20° C., usually about 10° C. to about 15° C., lower than the thermal melting point ($T_m$) for the specific sequence at a defined ionic strength and pH. The $T_m$ is the temperature (under defined ionic strength and pH) at which 50% of the target sequence hybridizes to a matched probe. Typically, stringent conditions will be those in which the salt concentration is about 0.02 molar at pH 7 and the temperature is at least about 60° C. For instance, in a standard Southern hybridization procedure, stringent conditions will include an initial wash in 6×SSC at 42° C. followed by one or more additional washes in 0.2×SSC at a temperature of at least about 55° C., typically about 60° C. and often about 65° C.

Nucleotide sequences are also substantially identical for purposes of this invention when the polypeptides and/or proteins which they encode are substantially identical. Thus, where one nucleic acid sequence encodes essentially the same polypeptide as a second nucleic acid sequence, the two nucleic acid sequences are substantially identical, even if they would not hybridize under stringent conditions due to degeneracy permitted by the genetic code (see, Darnell et al. (1990) *Molecular Cell Biology*, Second Edition Scientific American Books W. H. Freeman and Company New York for an explanation of codon degeneracy and the genetic code). Protein purity or homogeneity can be indicated by a number of means well known in the art, such as polyacrylamide gel electrophoresis of a protein sample, followed by visualization upon staining. For certain purposes high resolution may be needed and HPLC or a similar means for purification may be utilized.

By "immunogenic" is meant a compound (e.g., a polypeptide or fragment thereof) having the ability to stimulate an immune response in an organism (e.g., an organism previously infected with *Chlamydia*).

Libraries with discrete members in defined locations provide several advantages over pooled libraries including increased sensitivity for each individual antigen as well as a far more rapid screening procedure.

Other features and advantages of the invention will be apparent from the following Detailed Description, the drawings, and the claims.

BRIEF DESCRIPTION OF THE DRAWINGS

FIG. 14 is the peptide sequence of the CT788 (Cta1) protein (SEQ ID NO:1) and CT788$_{133-152}$ (Cta1$_{133-152}$) (SEQ ID NO:2).

DETAILED DESCRIPTION

In one aspect, the invention permits in vitro screening of proven human immunity effectors to identify their key target antigens from the complete proteome, or a portion thereof, from any disease-causing agent and from differentially expressed polypeptides in neoplastic cells. In another aspect, the invention provides compositions, including purified proteins and vaccines, and methods of treating or preventing a Chlamydia infection involving use of the CT788 polypeptide or fragment thereof as an antigen.

The technology of the first aspect of the invention enables a researcher to predict which epitope cocktail will prove effective in vivo, either as a prophylactic or a therapeutic vaccine. Importantly, it mimics the mammalian immune system in vitro and presents it with every antigen that a given disease-causing agent might express in the infected host. Within a matter of a few days, it is possible to identify, from the entire proteome of a disease-causing agent, or portion thereof, the specific antigens that will stimulate the immune system most effectively in vivo, a task that previously was impossible.

At the core of the invention is the ability to rapidly identify antigens that result in the in vivo stimulation of protective cytotoxic T-lymphocytes, allowing identified immune targets to be incorporated immediately into existing antigen delivery systems to produce multivalent vaccine formulations with the highest probability of generating protective cell-mediated immunity.

Figure 1:
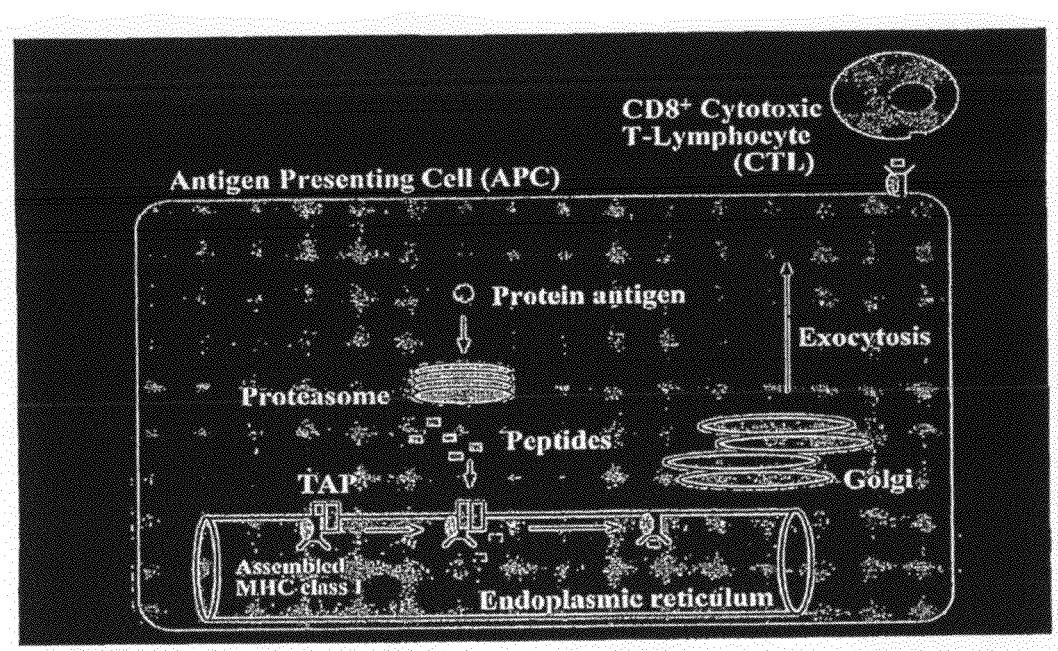
FIG. 1 is a schematic diagram showing conventional MHC class I antigen presentation.
Figure 2:
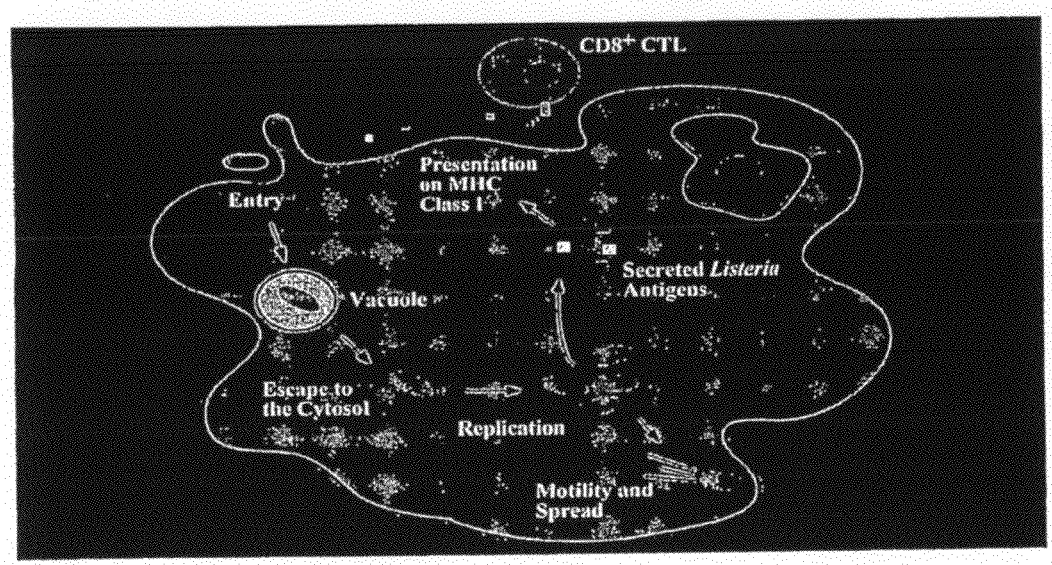
FIG. 2 is a schematic diagram showing stimulation of CD8$^+$ effector T-cell responses during *Listeria monocytogenes* infection.
Figure 3:
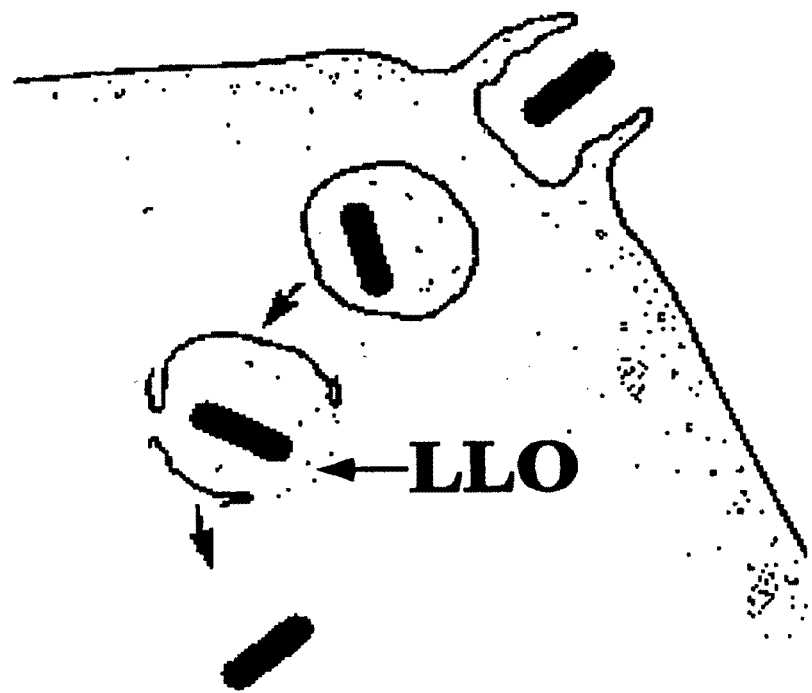
FIG. 3 is a schematic diagram showing listeriolysin O (LLO)-mediated escape of *L. monocytogenes* from a vacuole during infection.
Figure 4:
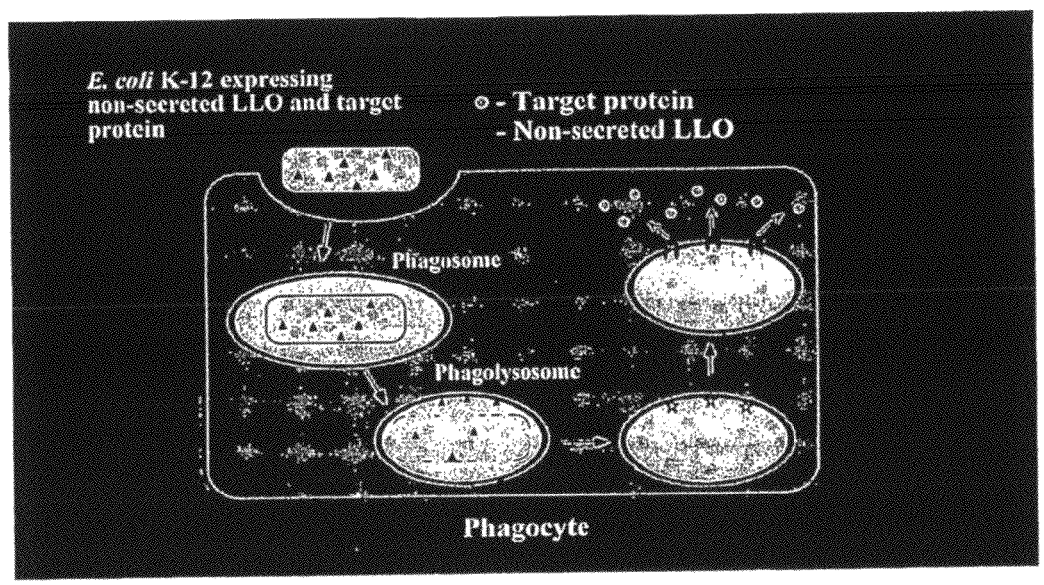
FIG. 4 is a schematic diagram showing LLO-mediated delivery of a polypeptide expressed in *E. coli* to the cytosol of a cell capable of endocytosing a bacterium.
Figure 5:
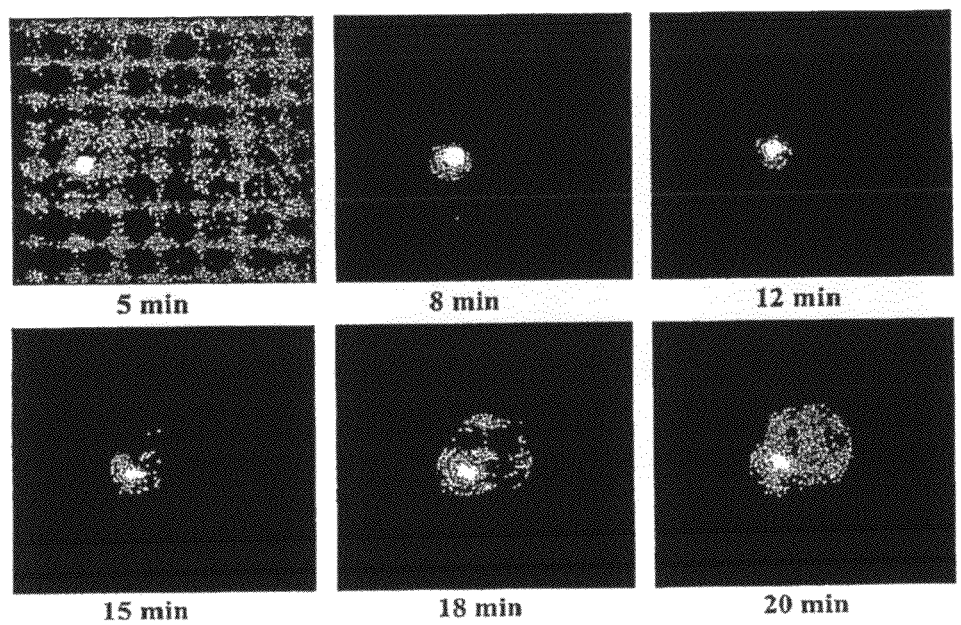
FIG. 5 is a set of images showing delivery of *E. coli* expressing GFP and LLO to the cytoplasm of a cell.
Figure 6:
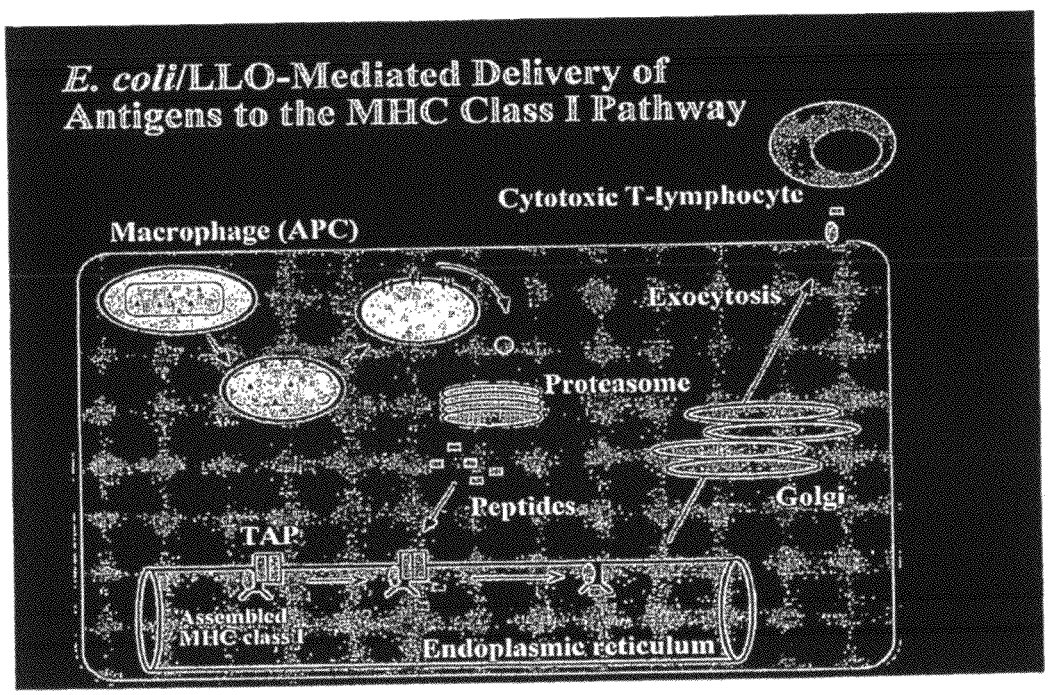
FIG. 6 is a schematic diagram showing *E. coli*/LLO-mediated delivery of antigens to the MHC class I pathway.

One of the key components of a protective cell-mediated immune response are CD8$^+$ cytotoxic T-lymphocytes (CTLs), which can recognize and eliminate pathogen-infected host cells, preventing dissemination of the pathogen within the host. The generation of CTLs during a natural infection often requires the production of pathogen-specific antigenic proteins within the cytosol of host cells. During intracellular infection, antigenic proteins present within the host cell cytosol are proteolytically degraded into peptides. These peptides are subsequently displayed on the surface of host cells in association with major histocompatibility complex (MHC) class 1 molecules (FIGS. 1 and 2). Peptide/MHC complexes on the surface of host cells are recognized by CTLs, leading to CTL-mediated killing of infected host cells and the development of protective T-cell memory. However, relatively few advances have been made in developing strategies to identify pathogen-specific antigens efficiently that are used as targets for the MHC class I pathway. Such targets are the frontline materials for incorporation into component vaccines to stimulate protective CTL memory and prevent infection by an invading microorganism. The development of effective methods to identify pathogen-specific antigenic proteins and target them to the MHC class I presentation pathway is therefore of fundamental importance in the rational design of vaccines against intracellular pathogens. While several current vaccine strategies are in development for in vivo antigen delivery, prior to the present invention, no strategy existed for the rapid determination of the entire antigenic profile of an infectious disease pathogen to determine the most appropriate antigenic determinants to include in a vaccine formulation.

The present invention allows for the efficient in vitro expression of the entire protein complement of an infectious pathogen coupled with targeting of the expressed proteins to host antigen-presenting cells (APC) for the generation of CTL responses. Antigens delivered to host cells through this targeted expression system are processed by the MHC class I pathway (FIG. 1) for presentation to CTLs. Candidate vaccine antigens are identified in this manner through the use of pathogen-specific CTL lines that have been generated from previously infected individuals.

As outlined below, the present invention has been applied to *Chlamydia trachomatis*, an intracellular bacterial pathogen and the most common sexually transmitted disease agent in the United States. *C. trachomatis* is also the leading cause of preventable blindness worldwide, and no vaccine is currently available. *C. trachomatis*-specific CTL lines that provide protective immunity in adoptive transfer studies were obtained from a mouse model and used to identify CTL-eliciting antigens. One antigen that corresponds to a unique member of the 894 possible *C. trachomatis* open reading frames, was identified from each CTL line screened against a *C. trachomatis* expression library. The identified antigens stimulate protective CTLs during *C. trachomatis* infection. Methods for producing libraries of the invention and performing the screening assays are described herein.

Generation of Libraries from a Pathogenic Organism

To generate a library of the invention, open reading frames or portions thereof from the genome of a pathogenic organism (e.g., a virus or a bacterium) are cloned into vectors capable of being expressed (e.g., operably linked to a promoter) in the cell or virus of which the members of the library include. This may be accomplished by any means known in the art. In one embodiment, PCR primers are designed to amplify open reading frames identified in the genome of a pathogenic organism. Sets of primers may be designed to amplify 10%, 20%, 30%, 40%, 50%, 60%, 70%, 80%, 90%, 95%, 98%, 99%, or even 100% of the open reading frames, or portions thereof, from the genome of the pathogenic organism. Primer design may be performed using a computer program, for example, the GAP (Genome-wide Automated Primer finder server) computer program, available from the University of California at Irvine, which allows rapid design of primers targeting large numbers of open reading frames from the genome of a pathogen. In one embodiment, primers are designed such that secretion signal sequences from the proteins of the pathogenic organism are removed. Pathogenic bacteria and viruses whose genomes have been sequenced or are being sequenced may be found, for example, at the Genome Online Database (GOLD) (Liolios K et al., *Nucleic Acids Res.* 34(Database issue):D332-334, 2006). Pathogenic organisms (e.g., bacterial pathogens) whose genomes are fully sequenced are particularly useful in the present invention.

Alternatively, reverse transcription of mRNA may be used to generate a library of the invention. Reverse transcriptase in conjunction with a primer targeted to a specific mRNA sequence may be used to transcribe into a DNA sequence the coding region, or portion thereof, contained within the mRNA. Subsequent amplification by PCR (e.g., as described herein) may be used to generate sufficient quantities of DNA for the cloning the desired polynucleotide in to an expression vector.

To generate the discrete members of the library, each PCR reaction containing primers specific to an open reading frame or portion thereof may be carried out in a separate reaction volume (e.g., in an 96 well plate). In one embodiment, a two step PCR process is used. The first set of primers is used to amplify the desired open reading frames, and a second set of primers is used to append additional sequences onto the amplified sequences for cloning. Such additional sequences may include sites for restriction enzymes or recombination sequences for cloning (e.g., the Gateway system from Invitrogen or the MAGIC system (Li et al. *Nat. Genet.* 7(3):311-9, 2005)), or any sequence tag known in the art (e.g., a $His_6$ tag, a myc tag, or a SIINFEKL epitope (SEQ ID NO:155)). The PCR products are introduced into the cloning vectors as appropriate for the system used, as is known in the art. If a cloning vector lacks a promoter capable of driving expression in the cell or virus of the library, it will be subsequently necessary to clone the ORF or fragment thereof into a vector containing a promoter. During any of the clone steps, peptide tags, such as those described herein, may be added to either the N-terminus or C-terminus of the polypeptides clones, or portions thereof.

Once the polynucleotide encoding at least portions of the polypeptides are cloned into vectors capable of expression, they may each be introduced in to an appropriate host cell or virus, thereby forming a library of the invention. The methods described herein have been used to create a library expressing 888 of the 894 polypeptides found in the *C. trachomatis* genome.

Pathogenic organisms useful in the invention include, for example, adenovirus, *Ascaris lumbricoides*, astrovirus, *Bacteroides* spp., beta-hemolytic streptococci, BK virus, *Blastocystis hominis, Blastomyces dermatitidis, Bordetella pertussis*, Bunyavirus, *Campylobacter fecalis, Candida* spp., *Chlamydia pneumoniae, Chlamydia psittaci, Chlamydia trachomatis, Clonorchis sinensis, Clostridium difficile, Clostridium* spp., Coagulase-negative staphylococci, *Coccidoides immitis, Cornybacterium diphtheriae, Cornybacterium* spp., coronavirus, coxsakievirus A, coxsakievirus B, *Cryptococcus neoformans*, cryptosporidium, cytomegalovirus, echovirus, *Entamoeba histolytica, Enterbater* spp., *Enterobius vermicularis, Enterococcus* spp., Epstein-Barr virus, equine encephalitis virus, *Escherichia coli, Escherichia* spp., fungi, *Giardia lamblia, Haemophilus influenzae*, hepatitis virus, hepatitis C virus, herpes simplex virus, *Histoplasma capsulatum*, HIV, Hymenolepis nana, influenza virus, JC virus, *Klebsiella* spp., *Legionella* spp., *Leishmania donovani*, lymphocytic choriomeningitis virus, microfilariae, microsporidium, *Mycobacterium tuberculosis, Mycoplasma pneumoniae*, myxovirus, *Necator americanus, Nocardia* spp., Norwalk virus, *Opisthorchis viverrini*, parainfluenza virus, paramyxovirus, *Plasmodium* spp., *Pneumocystis carinii, Proteus* spp., *Pseudomonas aeruginosa, Pseudomonas* spp., rabies virus, respiratory syncytial virus, rhinovirus, rotavirus, *Salmonella, Shigella,* St. Louis encephalitis virus, Staphylococcus aureus, Streptococcus pneumoniae, Strongyloides stercoralis, togavirus, *Toxoplasma* spp., *Trichuris trichiura*, Varicella-Zoster virus, vibrio cholera, *Viridans streptococci*, and *Yersinia enterocolitica.*

Particularly useful the present invention are obligate intracellular pathogens. Intracellular bacteria include, for example, *Anaplasma bovis, A. caudatum, A. centrale, A. marginale A. ovis, A. phagocytophila, A. platys, Bartonella bacilliformis, B. clarridgeiae, B. elizabethae, B. henselae, B. henselae phage, B. quintana, B. taylorii, B. vinsonii, Borrelia afrelii, B. andersonii, B. anserina, B. bissettii, B. burgdorferi, B. crocidurae, B. garinii, B. hermsii, B. japonica, B. miyamotoi, B. parkeri, B. recurrentis, B. turdi, B. turicatae, B. valaisiana, Brucella abortus, B. melitensis, Chlamydia pneumoniae, C. psittaci, C. trachomatis, Cowdria ruminantium, Coxiella burnetii, Ehrlichia canis, E. chaffeensis, E. equi, E. ewingii, E. muris, E. phagocytophila, E. platys, E. risticti, E. ruminantium, E. sennetsu, Haemobartonella canis, H. felis, H. muris, Mycoplasma arthriditis, M. buccale, M. faucium, M. fermentans, M. genitalium, M. hominis, M. laidlawii, M lipophilum, M. orale, M. penetrans, M. pirum, M. pneumoniae, M. salivarium, M. spermatophilum, Rickettsia australis, R. conorii, R. fells, R. helvetica, R. japonica, R. massiliae, R. montanensis, R. peacockii, R. prowazekii, R. rhipicephali, R. rickettsii, R sibirica*, and *R. typhi*. Exemplary intracellular protozoans are *Brachiola vesicularum, B. connori, Encephalitozoon cuniculi, E. hellem, E. intestinalis, Enterocytozoon*

*bieneusi, Leishmania aethiopica, L. amazonensis, L. braziliensis, L. chagasi, L. donovani, L. donovani chagasi, L. donovani donovani, L. donovani infantum, L. enriettii, L. guyanensis, L. infantum, L. major, L. mexicana, L. panamensis, L. peruviana, L. pifanoi, L. tarentolae, L. tropica, Microsporidium ceylonensis, M. africanum, Nosema connori, Nosema ocularum, N. algerae, Plasmodium berghei, P. brasilianum, P. chabaudi, P. chabaudi adami, P. chabaudi chabaudi, P. cynomolgi, P. falciparum, P. fragile, P. gallinaceum, P. knowlesi, P. lophurae, P. malariae, P. ovale, P. reichenowi, P. simiovale, P. simium, P. vinckeipetteri, P. vinckei vinckei, P. vivax, P. yoelii, P. yoelii nigeriensis, P. yoelii yoelii, Pleistophora anguillarum, P. hippoglossoideos, P. mirandellae, P. ovariae, P. typicalis, Septata intestinalis, Toxoplasma gondii, Trachipleistophora hominis, T. anthropophthera, Vittaforma corneae, Trypanosoma avium, T. brucei, T. brucei brucei, T. brucei gambiense, T. brucei rhodesiense, T. cobitis, T. congolense, T. cruzi, T. cyclops, T. equiperdum, T. evansi, T. dionisii, T. godfreyi, T. grayi, T. lewisi, T. mega, T. microti, T. pestanai, T. rangeli, T. rotatorium, T. simiae, T. theileri, T. varani, T. vespertilionis*, and *T. vivax.*

Infectious fungi that may be used in the invention include yeast such as *Candida albicans, Candida stellatoidea, Candida tropicalis, Candida parapsilosis, Candida krusei, Candida pseudotropicalis, Candida quillernondii, Candida glabrata, Candida lusianiae*, and *Candida rugosa*. Other fungi include *Microsporum canis* and other *M.* spp., *Trichophyton* spp. (e.g., *T. rubrum* and *T. mentagrophytes*), *Torulopsis glabrata, Epidermophyton floccosum, Malassezia furfur, Pityropsporon orbiculare, P. ovale, Cryptococcus neoformans, Aspergillus fumigatus* and other *Aspergillus* spp., Zygomycetes (e.g., *Rhizopus, Mucor*), *Paracoccidioides brasiliensis, Blastomyces dermatitides, Histoplasma capsulatum, Coccidioides immitis*, and *Sporothrix schenckii.*

For generation of a library in a bacterial host, any vector capable of expressing the cloned polynucleotide may be used in the host bacteria. In one embodiment, a laboratory strain of *E. coli* is used; appropriate vectors for expression in *E. coli* are well known in the art and include vectors such as the pET expression vector system (EMD Biosciences, San Diego, Calif.), pDESTSL8 (described herein), and pDEST17 (Invitrogen). Vectors may be modified to include N- or C-terminal tags, as desired, for example, for use in verification of the library (e.g., as described herein). Such vectors may also contain an inducible promoter (e.g., the T7 polymerase promoter) as are well known in the art, which allow for expression upon application of an exogenous chemical (e.g., IPTG (isopropyl-beta-D-thiogalactopyranoside)) or upon application of a phage (e.g., CE6 phage) depending on the bacterial strain used.

For generation of viral libraries (e.g., phage display libraries), polynucleotides forming a library are cloned into phage vectors. Such vectors and vector systems are well known in the art and include the Novagen T7Select® phage display vectors (EMD Biosciences).

In certain embodiments, bacterial libraries of the invention, in addition to containing a first polynucleotide from the pathogenic organism, may contain an second polynucleotide sequence, either as part of the first polynucleotide (in addition to the sequence from the pathogenic organism) or as part of a second expression vector. This second polynucleotide sequence may encode a second protein, for example, listeriolysin O (LLO).

*E. coli*/LLO system

The *E. coli*/LLO system provides a means for a protein expressed in *E. coli*, following endocytosis into a cell, to escape from the vacuole in which it is endocytosed, and contact the cytosol of the cell (FIG. 3). LLO acts by perforating the vacuole, thereby allowing its contents to escape into the cytoplasm. Listeriolysin O exhibits greater pore-forming ability at mildly acidic pH (the pH conditions within the vacuole) and is therefore well suited for this purpose. This allows for enhanced processing of the expressed protein through the MHC class I pathway (see FIGS. 4-6). This system is described extensively in U.S. Pat. No. 6,004,815, which is hereby incorporated by reference. In addition to LLO, the libraries and methods of the invention may employ other proteins with similar activity; any protein (e.g., a pore-forming protein) that facilitates delivery of potentially antigenic proteins to the cytoplasm of a cell capable of endocytosing the bacteria or virus of the library of the invention may be employed. The *E. coli*/LLO system is particularly useful for screening for antigens that activate $CD8^+$ CTL cells. Libraries of the invention prepared without LLO may be used to screen for $CD4^+$ CTL cell activation.

The examples presented herein are intended to illustrate, rather than limit, the present invention.

Example 1

Cloning *Chlamydia trachomatis* Genome

Each ORF in the *Chlamydia trachomatis* serovar D/UW-3/Cx genome was amplified through a 2-step PCR procedure. The first step used primers specific for each ORF to amplify each sequence in a 96-well format. The primers were designed to remove any secretion signal sequences present in the ORFs to prevent secretion in *E. coli* when they are expressed and to minimize toxicity. The second PCR step was used to add the required recombination sequences to the 5' and 3' ends of each PCR product.

Once the ORFs were amplified and the recombination sequences were added, the PCR products were recombined into a DONR vector. This can be done using the Gateway system or the MAGIC system. For this library, the Gateway system was used. The final PCR product was incubated with the pDONR221 plasmid in the presence of Gateway BP recombinase. After an overnight incubation, the reaction solution was transformed directly into *E. coli* which were then plated on kanamycin-containing LB agar plates to select for the presence of the DONR plasmid. Any bacteria that grow must contain a DONR vector which has recombined with a PCR product because the DONR plasmid is toxic to *E. coli* if it has not recombined due to the presence of a toxin gene in the plasmid. When the DONR plasmid recombines with a PCR product this toxin gene is lost allowing the bacteria to support the presence of the plasmid.

The MAGIC recombination system works very similarly, except the PCR product is transformed directly into *E. coli* which already contain the MAGIC1 donor vector. The recombination step occurs within the bacteria. Successful recombination events are then selected for by plating the bacteria on plates containing chlorophenylalanine. This chemical is toxic to *E. coli* containing the magic donor vector that has not recombined with the PCR product due to the presence of the pheS gene in the vector, which again is lost during a successful recombination. Only *E. coli* that contain a donor vector that has recombined with the PCR product survive. The whole transformation process in either system is done in a 96-well format including the plating procedure to ensure that all colonies appearing in any well on the agar plate are the result of a successful recombination of only the single ORF sequence that was amplified in the corresponding well during the PCR step. This allows for the cloning of each ORF in clonal populations.

A clone for each ORF was inoculated into LB containing kanamycin in 96-deep well plates. The plasmid DNA from each clone was isolated through a 96-well mini-prep procedure. Primers complimentary to sequences in the DONR vector 5' and 3' of the cloned ORF sequence were used to PCR amplify the sequence that was recombined into the vector. The PCR product was run on an agarose gel and the size of the product was compared to the predicted size. Any clone that contained a recombined sequence which was significantly different from the predicted size was abandoned and a new clone for that ORF was chosen and tested for the proper size. All clones that contained sequences of the proper length were moved on to the next step of the cloning procedure.

Figure 7:
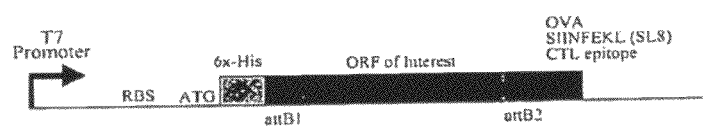
FIG. 7 is a schematic diagram of the modified Gateway system used in cloning of the *C. trachomatis* library.

For the MAGIC system, the donor vector can be used to express the ORFs; thus, no further cloning is required. In the Gateway system, however, the ORF sequence is shuttled to a second vector containing a promoter that allows for expression of the ORF. This was accomplished by incubating the isolated DONR plasmid DNA with the destination vector pDESTSL8 in the presence of Gateway LR recombinase. pDESTSL8 was constructed in our lab from pDEST17 (FIG. 7) by adding a C-terminal fusion which contains the SIINFEKL epitope (SEQ ID NO:155). After an 18 hr incubation, the reaction solution was transformed directly into *E. coli* which was then plated on carbenicillin-containing LB agar plates in a 96-well format. A clone for each ORF was inoculated into carbenicillin-containing LB in 96-well plates to select for the bacteria that have taken up pDESTSL8 that has recombined in the ORF sequence. The plasmid DNA for each clone was isolated and primers complimentary to sequences in pDESTSL8 5' and 3' of the recombined ORF were used to PCR amplify the recombined sequence. These product of the PCR amplification were analyzed by agarose gel electrophoresis; any clone with an insert of an incorrect size was abandoned and a new clone for that ORF was tested. Every clone with an insert with the correct size was deemed correct and was moved on to be tested for expression.

Generation of Libraries from Neoplastic Cells

In another embodiment of the invention, a replicable library that includes polynucleotides encoding at least fragments of polypeptides whose expression is increased (e.g., by a factor of at least 1.05, 1.1, 1.2, 1.4, 1.5, 1.75, 2, 3, 4, 5, 7, 10, 25, 50, or 100 times) in a neoplastic cell such as a cancer cell (e.g., a breast cancer cell) as compared to the corresponding normal cell is provided. Identification of a set of polynucleotides with increased expression in neoplastic cells may be performed by any method known in the art. Typically, expression is profiled using an expression array, such as those available from Affymetrix. Polynucleotides whose expression is increased in a neoplastic cell are thus identified using such expression arrays and may be subsequently used to generate a library of the invention.

Cloning of polynucleotides whose expression is increased in a neoplasm may be performed by reverse transcription of the individual mRNAs transcribed from each polynucleotide identified as having increased expression. Primers specific to each mRNA are selected and used to individually transcribe the mRNA sequences into DNA sequences. The DNA sequences may then be cloned in an appropriate vector containing a promoter capable of expression in the cell or virus of the library, typically following amplification of each DNA sequence by PCR. Once each polynucleotide is cloned into a vector, the polynucleotides may be introduced into a cell or virus as described herein.

Polynucleotides overexpressed in neoplastic cells as compared to normal cells may also be identified through the use of cDNA subtraction libraries. Methods for generating such libraries are known in the art and are commercially available, for example, the Clonetech PCR-Select products (Clonetech Laboratories, Inc., Mountain View, Calif.).

Expression of Polynucleotides

For use in the methods of the invention, a cell or virus forming a member of a library can express the polynucleotide encoding at least a portion of a polypeptide from the pathogenic organism. In bacterial systems with inducible promoters, this is accomplished by administration of the appropriate substance (e.g., chemical or phage) to induce protein expression. In the case of the *C. trachomatis* library described in Example 1, this was performed as follows.

Example 2

Expression of *C. trachomatis* Polynucleotides

Each expression plasmid containing an ORF was transformed into *E. coli* which already contained a plasmid to express the cytosolic form of listeriolysin O (cLLO). The bacteria were plated on LB agar plates containing both carbenicillin and chloramphenicol to select for both plasmids. A colony for each ORF was picked, inoculated into carbenicillin and chloramphenicol containing LB in 96-well plates and grown for 18 hrs. The stationary phase culture was then diluted into fresh LB containing 0.2% maltose, carbenicillin and chloramphenicol. After 4 hours of growth the $OD_{600}$ was taken for each well to determine the number of bacteria in each well. $MgSO_4$ was added to bring the concentration to 10 mM in each culture. CE6 phage, a replication deficient lambda phage which contains in its genome the gene for T7 polymerase under a constitutive promoter, was then added at an MOI of 12:1. Once the phage has infected the bacteria, the T7 polymerase is expressed which can then transcribe a chlamydial ORF under the control of a T7 promoter. The cultures were gently mixed and incubated without shaking for 20 minutes at 37° C. After 20 min, the cultures were incubated shaking for an additional 1 hour and 40 minutes to allow for expression of ORF. The $OD_{600}$ from each well was then measured to determine the concentration of bacteria in each culture well. $1 \times 10^8$ bacteria were harvested from each well, pelleted and resuspended in 1 mL of 0.5% paraformaldehyde. The cultures were incubated for 30 minutes at room temperature. The cultures were then pelleted and washed three times with PBS. After the final wash, the cell were pelleted and resuspended in 1 mL of RP-10 media. The cultures were then aliquoted out in volumes of 20 µL into 96-well plates and frozen at −80° C. This procedure can yield greater than 50 separate aliquots of the library to screen different T-cell lines.

Verification of the Expression of the Library

Any method known in the art may be used to determine whether each member of the library is able to express the polynucleotide from the pathogenic organism or a neoplastic cell (e.g., western blotting). In the *C. trachomatis* library described herein, verification of expression was accomplished as follows.

Example 3

Testing for Expression

Figure 8:
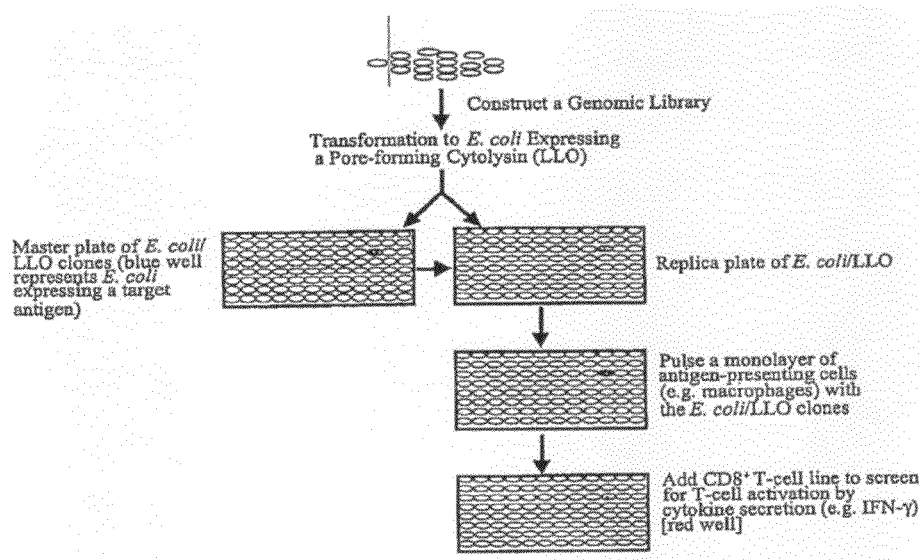
FIG. 8 is a schematic diagram showing the expression cloning strategy for identification of antigens for any pathogen of interest.
Figure 9:
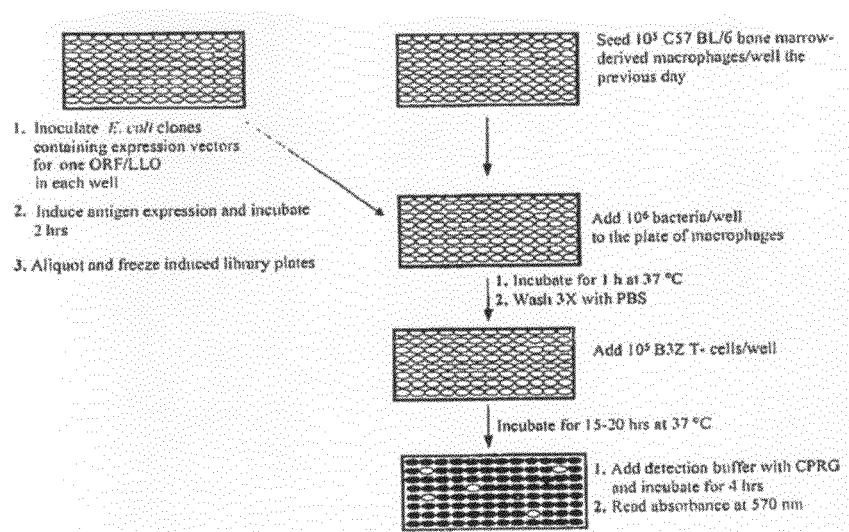
FIG. 9 is a schematic diagram of the validation strategy of the library employed using B3Z T-cells, which recognize the SIINFEKL tag (SEQ ID NO:155) present on the expressed proteins using the modified Gateway vector described herein.
Figure 10:
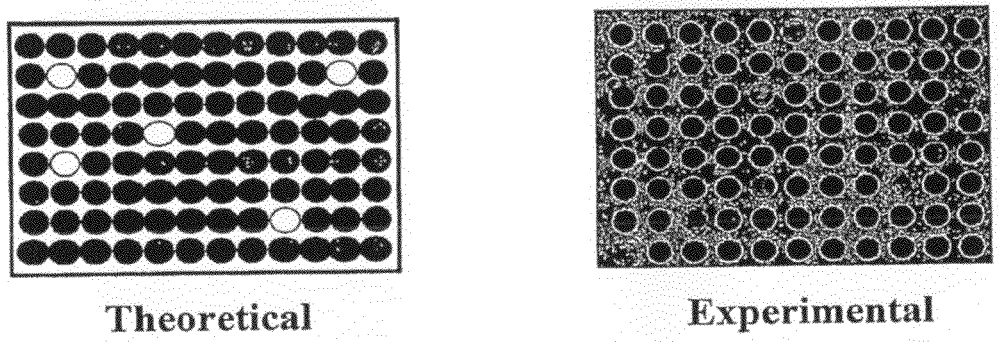
FIG. 10 is an image showing that library validation strategy works as theorized by successfully determining which proteins in the library were expressed.

We developed a high-throughput test for protein expression utilizing the SIINFEKL epitope (SEQ ID NO:155) fused to the C-terminus of each ORF for verification of protein expression (FIGS. 8-10). To perform this assay, a frozen aliquot of the library is thawed and added to macrophages of the H2$^b$ haplotype, which were seeded the previous day in 96-well plates. The macrophage/bacteria mixture is incubated for an hour during which time the bacteria are phagocytosed by the macrophages. In the phagosome, the bacteria are lysed, releasing all of the proteins being expressed by the *E. coli* into the vacuole including the chlamydial protein and cLLO. The cLLO then perforates the phagosome membrane, allowing the chlamdyial protein access to the cytosol of the macrophage where it can be processed and peptides from the protein can be presented on MHC Class I molecules. If the chlamydial protein was expressed to full length, it has the SIINFEKL epitope (SEQ ID NO:155) fused to its C-terminus. This epitope will be delivered along with the chlamydial protein and will be processed and presented on the MHC Class I molecules on the surface of the macrophages. This MHC-peptide complex is probed for by adding B3Z T-cell hybridoma cells at the end of the hour incubation. B3Z cells become activated when they recognize the MHC-SIINFEKL complex (FIG. 9). When they become activated, β-galactosidase expression is induced. The B3Z cells are incubated with the macrophages for 15-20 hours to allow the B3Z cells time to scan the macrophages for the MHC-peptide complex and upregulate β-galactosidase if the complex is present. After 15-20 hours, LacZ buffer is added to detect the amount of β-galactosidase activity in each well of the plate. LacZ buffer contains a detergent to lyse the macrophages and a β-galactosidase substrate, chlorophenyl red-β-D-galactopyranoside (CPRG), which turns from yellow to purple when it is cleaved by β-galactosidase. The amount of cleaved product is determined by measuring the OD$_{570\ nm}$ of each well in a spectrophotometer. Thus, a strong signal at 570 nm indicates both that the chlamydial protein that was expressed in that well was expressed to full length and was delivered to the MHC Class I pathway.

Determining Whether a Polypeptide from a Pathogen or Neoplastic Cell is Immunogenic A library of cells or viruses contain polynucleotides encoding polypeptides from a pathogenic organism or from a neoplastic cell may be screened to determine which of the polypeptides encoded by the polynucleotides are immunogenic. This may be accomplished by contacting each member of the library with a second cell (e.g., a macrophage) capable of endocytosing the cell or virus of the library, and displaying portions of the expressed polypeptide of the library on the surface of the second cell. This process is described, for example, in U.S. Pat. No. 6,008,415. The second cell is then contacted with a CTL cell from an organism previously infected with the pathogenic organism, a CTL cell from an organism with a neoplasm, or a CTL cell from an organism that previously had a neoplasm. Contacting with a CTL cell may be proceeded by fixing the second cell, e.g., using paraformaldehyde. A CTL capable of binding a presented portion of the antigen/protein will result in secretion of cytokines. Cytokine secretion (e.g., secretion of IFNγ, IL-2, or TNF) may be assayed for as is known in the art, for example, using an ELISA assay. In a working example, the *C. trachomatis* library described herein was screened as described in Example 4 below.

Cytotoxic T Lymphocytes

Pools of CTL cells for use in the methods of the invention may be derived by any means known in the art. Typically, in screening for antigens to pathogenic organisms, CTL cells are prepared from a mammal previously infected with the pathogen. This preparation will contain CTL cells specific for antigens from the pathogen.

*C. trachomatis*-specific CTLs may be elicited from mice as follows. A mouse was injected i.p. with 10$^7$ IFU of *C. trachomatis*. 14 days later the mouse was euthanized and the spleen was harvested. The spleen was mashed through a 70 μm screen to create a single cell solution of splenocytes. The CD8$^+$ T-cells were isolated from the splenocytes using α-CD8 antibodies bound to MACS magnetic beads using MACS separation protocols standard in the art (see, for example, MACS technology available from Miltenyi Biotec Inc., Auburn, Calif.). The isolated CD8$^+$ cells were added to macrophages of the same haplotype which were infected with *C. trachomatis* 18 hours prior in a 24-well dish. Irradiated splenocytes from a naïve mouse were added as feeder cells in media containing IL-2. The cells were incubated for 10 days during which time the *C. trachomatis*-specific T-cells were stimulated by the infected macrophages and replicated. On day 10 the T-cells were stimulated again using macrophages infected with *C. trachomatis* 18 hours prior and irradiated splenocytes. This procedure was repeated until sufficient amounts of T-cells were present to screen the entire library.

Figure 11:
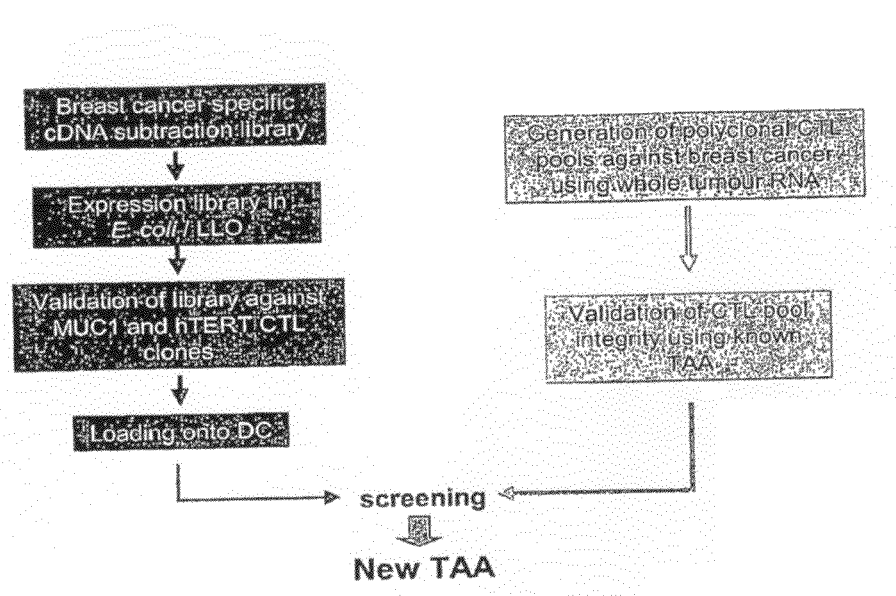
FIG. 11 is a schematic diagram showing a strategy for screening for breast cancer antigens.

For preparation of CTL cells for use in screening for antigens to neoplastic cells, e.g., breast cancer cells, polyclonal CTL pools specific to breast cancer are generated using whole tumor RNA. The CTL pool is then verified using known tumor-associated antigens (FIG. 11).

CTL cells may be cloned from a human subject as described by, for example, Hassell et al. (*Immunology* 79:513-519, 1993).

Example 4

Screening for Unknown Antigens

Figure 12:
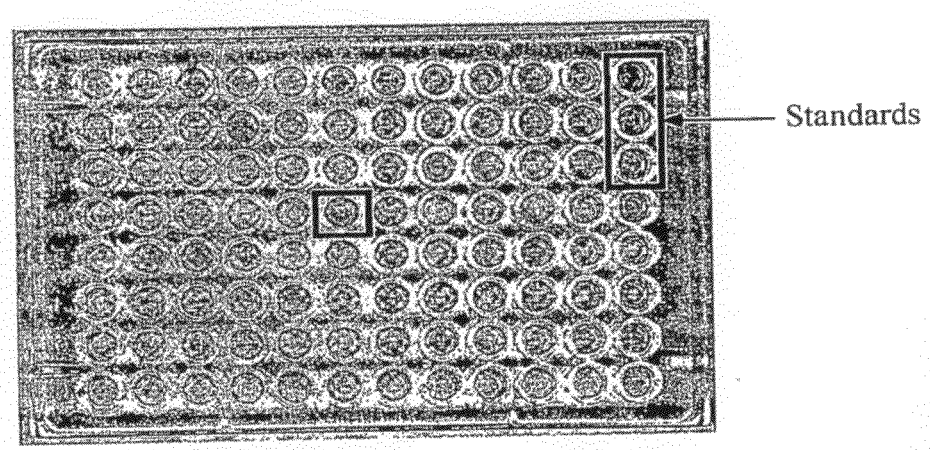
FIG. 12 is an image showing a positive result from screening of the *C. trachomatis* library using a *Chlamydia* specific T-cell line.

A frozen aliquot of the library (10 96-well plates in total) is thawed and added to macrophages which were seeded the previous day in 10 96-well plates. The plates are incubated for 2 hours, washed and fixed with 1% paraformaldehyde to kill the macrophages and stabilize any MHC Class I-peptide interactions. The cells are then washed again to remove the paraformaldehyde. *C. trachomatis*-specific CD8$^+$ T-cells of unknown specificity are then added to each well. If the epitope the T-cells recognize is being presented in a given well, the T-cells will become activated. T-cell activation is detected by measuring the amount of IFNγ present in the supernatant of each well after 18-20 hours of culture using an IFNγ ELISA kit (see FIG. 12). This may also be accomplished by testing for other cytokines released by activated T-cells such as IL-2. Any well which contains a much higher concentration of IFNγ than all the rest of the wells suggests the corresponding chlamydial protein in the library is a possible antigen. For any possible antigen, the process is repeated to ensure that the hit is not a false positive. If the antigen activates the T-cells in the secondary screen, the ORF is deemed an antigen and is moved on to epitope identification.

Epitope Identification

Once a polypeptide antigen is identified, it is often desirable to identify the epitope within the polypeptide to which the CTL cell is responding. This may be accomplished by recursively assaying each portion of the polypeptide using cloning techniques known in the art, or may be achieved using a system such as the Erase-a-Base kit (Promega). The truncated polypeptides are screened against CTL cells as described herein to determine which portions of the polypeptide are required to generate an immunogenic response.

In one embodiment, the specific peptide epitope recognized by the T-cell line is identified by making nested deletions of the full antigen sequence using the Erase-a-Base kit from Promega. The plasmid clone containing the antigen sequence is first digested with NheI and AatII. The NheI cut creates the proper 5' overhang near the 3' end of the ORF to allow the nucleases in the Erase-a-Base kit to cleave 3'-5' through the antigen sequence while the 3' overhang of the AatII cut site prevents the nuclease from digesting in the other direction and removing the sequence for the drug resistance cassette. Once the plasmid is cut with the restriction enzymes, the Erase-a-Base kit is used to make a series of 3' truncations in the sequence encoding the antigen by following the protocol supplied with the kit. These truncations are ligated and transformed into *E. coli* containing the plasmid to express cLLO. Protein expression is then induced with CE6 phage as described above. When expressed, the truncations will create proteins that are missing increasing amounts of their C-terminal peptide sequence. The different truncation clones are then rescreened with the original T-cell line using the procedure outlined above. The clones that no longer activate the T-cell line have lost the sequence of the epitope recognized by the T-cell line. The sequences of the largest truncation clone that no longer contains the epitope and the shortest truncation clone that still does contain the epitope are determined. The location of the 3' edge of the epitope resides in the peptide sequence the shortest positive clone contains and the largest negative clone does not. Overlapping 8-10 mer peptides of this sequence are synthesized. The peptides are then pulsed onto macrophages and screened for their ability to activate the T-cell line. The peptide that is capable of activating the T-cell line is deemed the epitope.

CT788

The invention also features the CT788 (Cta1) polypeptide and fragments thereof (e.g., immunogenic fragments including amino acids 133-152 of the CT788 protein (SEQ ID NO:2) and those listed in Table 1 (SEQ ID NOS:3-154) (e.g., an immunogenic fragment listed in Table 1)), pharmaceutical and vaccine compositions including the CT788 protein or fragments thereof (e.g., those described herein), and methods for treating or preventing a bacteria infection (e.g., a *Chlamydia* infection) by administration of CT788 or a fragment (e.g., an immunogenic fragment) thereof (e.g., a fragment described herein).

Identification of CT788 as an antigenic protein of *C. trachomatis* Although pathogen-specific TCR tg T cells had been used previously in other infectious disease models (Butz et al., *Immunity* 8:167-75, 1998; Sano et al., *J. Exp. Med.* 194:173-80, 2001; Roman et al., *J. Exp. Med.* 196:957-68, 2002; Coles et al., *J. Immunol.* 168:834-838, 2002; McSorley et al., *Immunity* 16:365-377, 2002), the NR1 mice described below are the first TCR tg mice with T cells specific for a pathogen that infects the genital tract. Previously, it had not been possible to examine T cell responses to genital pathogens such as *C. trachomatis* because it was difficult to identify and track naïve T cells specific for genital antigens in vivo. In particular, the inability to modify *C. trachomatis* genetically to express a heterologous T cell epitope as well as the lack of a well-defined *Chlamydia*-specific $CD4^+$ T cell antigen had made it difficult to study T cell responses to this genital pathogen.

Because murine $CD4^+$ T cell antigens recognized during *Chlamydia* infection had not been previously defined, analysis of primary *Chlamydia*-specific T cell responses had been limited to examining polyclonal T cell responses to undefined antigens (Cain et al., *Infect. Immunol.* 63:1784-1789, 1995). In these previous experiments, the investigators could not differentiate true *Chlamydia*-specific T cell responses from bystander T cell activation, which has been shown to contribute to the overall response in a number of other infectious disease models (Yang et al., *J. Immunol.* 136:1186-1193, 1986; Tough et al., *Immunol. Rev.* 150:129-142, 1996). As described below, we identified a $CD4^+$ T cell antigen Cta1 (CT788), which allows examination of an antigen-specific T cell response stimulated during *C. trachomatis* infection. This antigen was predicted to be a periplasmic protein because of an N-terminal signal sequence, but its function is unknown (Stephens et al, *Science* 282:754-759, 1998). Cta1 is conserved in all of the *C. trachomatis* serovars that have been sequenced, including those that cause genital tract infection, ocular infection, and LGV. Cta1 stimulated protective T cells following natural infection, suggesting that this protein may play a significant role in immunity against *C. trachomatis.*

Another difficulty in studying the initial encounter of T cells with antigen is the low precursor frequency of pathogen-specific T cells in an unimmunized animal. Other investigators have attempted to increase the frequency of *Chlamydia*-specific T cells by transferring T cell clones of unknown specificity into *Chlamydia*-infected mice (Hawkins et al., *Infect. Immunol.* 68:5587-5594, 2000; Hawkins et al., *Infect. Immunol.* 70:5132-5139, 2002). Because the transferred T cells are antigen-experienced and have been propagated through multiple rounds of restimulation, the response of these T cells cannot be used to model the initial encounter of naïve T cells with *C. trachomatis*. To overcome the limitations of previous approaches and study the initial *Chlamydia*-specific T cell response, we developed NR1, a TCR tg mouse line specific for Cta1. Here, adoptive transfer of NR1 cells into unimmunized mice was used to increase the frequency of naïve, *Chlamydia*-specific T cells while still maintaining the polyclonal T cell environment in the recipient animals (Pape et al., *Immunol. Rev.* 156:67-78, 1997).

The response of *Chlamydia*-specific T cells to the infected murine genital tract was then examined. An infection model where the uterus of the mouse was inoculated with the human *C. trachomatis* serovar L2 was employed. This route of infection had been previously used to prime *Chlamydia*-specific T cells that could subsequently be cultured from the spleen (Starnbach et al., *Infect. Immunol.* 63:3527-3530, 1995) and has also been demonstrated to cause salpingitis in mice (Tuffrey et al., *Br. J. Exp. Pathol.* 67:605-16, 1986; Tuffrey et al., *J. Exp. Pathol.* (*Oxford*) 71:403-10, 1990). Other studies have used a different *Chlamydia* species, *Chlamydia muridarum*, as a mouse model of infection. *C. muridarum* is not known to infect humans but causes an ascending infection when inoculated into the vaginal vault of female mice. We were, however, unable to use this model, as our Cta1-specific T cells did not recognize *C. muridarum*-infected cells (data not shown), suggesting the Cta1 epitope in *C. trachomatis* may not be conserved in the Cta1 homolog in *C. muridarum.*

Using intrauterine infection with a human serovar of *C. trachomatis, Chlamydia*-specific T cells exhibited a Th1 response in the genital tract in response to infection. These cells secreted IFNγ while still in the ILNs, and secretion continued following migration into the infected genital tract. IFNγ has long been implicated as a critical effector in *Chlamydia* clearance, but may also be a cause of the tissue pathology associated with infection. In vitro, IFNγ enhances the ability of phagocytes to control *Chlamydia* replication (Rottenberg et al., *Curr. Opin. Immunol.* 14:444-451, 2002). In vivo, susceptibility to *Chlamydia* infection is increased in IFNγ−/− mice and *Chlamydia*-specific T cells transferred into mice only appear to be protective if they secrete IFNγ (Loomis et al., *Curr. Opin. Microbiol.* 5:87-91, 2002). Besides its role in protection, IFNγ induces *Chlamydia* to develop into a persistent state in vitro (Rottenberg et al., *Curr. Opin. Immunol.* 14:444-451, 2002; Hogan et al., *Infect. Immunol.*

72:1843-1855, 2004), and there is evidence that organisms persist in some human infections (Villareal et al., *Arthritis. Res.* 4:5-9, 2002). Persistence or repeated infection with *Chlamydia* may contribute to tissue scarring in vivo (Beatty et al., *Microbiol. Rev.* 58:686-699, 1994). Consistent with the hypothesis that IFNγ may promote tissue pathology, lymphocytes from patients with *Chlamydia*-associated tubal factor infertility secreted high levels of IFNγ in response to *Chlamydia* relative to lymphocytes from control patients (Kinnunen et al., *Clin. Exp. Immunol.* 131:299-303, 2003).

In our model, upregulation of CD69 on NR1 T cells in the ILNs did not occur until three days following genital infection and proliferation did not occur until four days following the infection. The period between intrauterine *Chlamydia* inoculation and activation of NR1 cells may define the amount of time required for *Chlamydia* antigens to travel into the draining lymph nodes where the antigen can activate naïve T cells. This timing was significantly later than the proliferation induced in the spleen after systemic infection (data not shown). Elements of the immune system in the genital tissues are less well-characterized than those in intestinal tissues, but differences between these two mucosal surfaces are nonetheless apparent. Unlike the intestinal lumen, the genital mucosa lacks organized lymphoid elements (Parr et al., *Biol. Reprod.* 44:491-498, 1991; Nandi et al., *Reg. Immunol.* 5:332-338, 1993). While the intestinal lumen is equipped with Peyer's Patches that can immediately sample luminal contents, the initiation of T lymphocyte responses against genital pathogens must occur outside the genital mucosa, perhaps in the ILNs, which drain antigen from the genital tract (Parr et al., *J. Reprod. Immunol.* 17:101-14, 1990; Cain et al., *Infect. Immunol.* 63:1784-9, 1995; Hawkins et al., *Infect. Immunol.* 68:5587-94, 2000; Nandi et al., *Reg. Immunol.* 5:332-338, 1993). For example, T cells specific for the enteric pathogen *S. enterica* have been shown to be activated in the Peyer's Patches a few hours after oral infection, and T cells in these nodes proliferated extensively by two days post-infection (McSorley et al., *Immunity* 16:365-377, 2002). The amount of time it takes *Chlamydia* antigens to migrate from the genital surface to the ILNs may explain the lack of NR1 activation prior to three days post-infection.

The genital and intestinal mucosa also differ in cell surface adhesion molecules responsible for recruiting lymphocytes. Whereas interaction of the cc4f37 integrin on lymphocytes with the MAdCAM-1 adhesion molecule on the intestinal endothelium mediates recruitment of T lymphocytes to the intestinal mucosa, such an interaction does not appear to play a significant role in recruitment to the genital mucosa (Rott et al., *J. Immunol.* 156:3727-2736, 1996; Perry et al., *J. Immunol.* 160:2905-2914, 1998).

It has been previously demonstrated that T cells can protect mice against *Chlamydia* infection (Stambach et al., *J. Immunol.*, 153:5183-9, 1994; Starnbach et al., *J. Immunol.*, 171: 4742-9, 2003). However, previously it was not been possible to determine when and where naïve *Chlamydia*-specific T cells first encounter antigens, how they traffic following activation, and when and where they proliferate. A major limitation in analyzing these early events is the low precursor frequency of naïve *Chlamydia*-specific T cells. However, we have now generated the first tool to study the response of *Chlamydia*-specific naïve T cells—a T cell receptor (TCR) transgenic mouse.

Figures 13A, 13B:
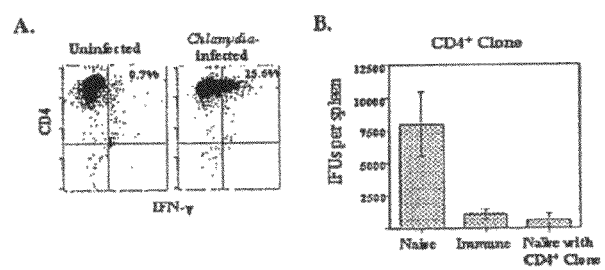
FIG. 13A is a graph showing the results of CD4 and IFNγ expression from flow cytometry using a CD4$^+$ T-cell clone being mixed with either uninfected or *Chlamydia*-infected BMM cells. Results are gated on live cells.
FIG. 13B is a graph showing the number of *Chlamydia* IFUs detected 72 hours after infection. Both previously infected (immune) mice and naive mice with the CD4$^+$ T-cell clone identified herein show low levels of infection as compared to naive mice without the CD4$^+$ T-cell clone.
Figure 15:
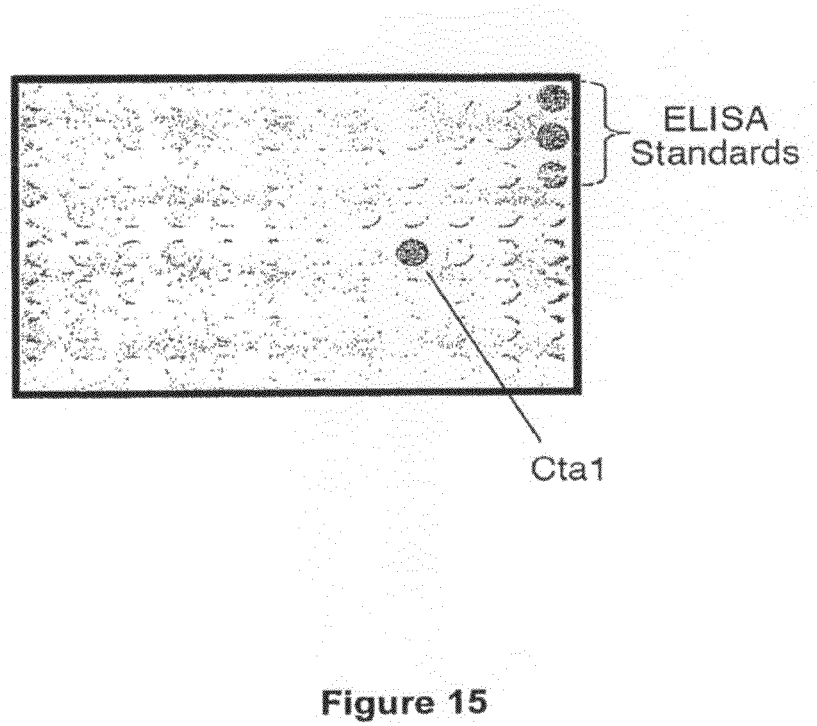
FIG. 15 is an image showing clones of *E. coli* expressing individual *C. trachomatis* ORFs cultured with BMMs and then incubated with the T cell clone NR9.2. This figure shows a plate where supernatant from the corresponding assay wells was tested for IFNγ in an ELISA assay. *E. coli* expressing Cta1 (encoded by ORF CT788) induced NR9.2 to secrete high levels of IFNγ (>370 ng/ml) whereas *E. coli* expressing other *Chlamydia* proteins in the library induced only background levels of IFNγ secretion (<26 ng/ml). The well indicated as Cta1 and ELISA Standards are yellow; other wells are colorless. The colorimetric intensity of the wells shown in the figure that do not correspond to Cta1 or the standards are typical of results seen with all the other *E. coli* clones in the library. ELISA standards corresponding to high amounts of IFNγ are indicated.

*Chlamydia* specific CD4+ T cell clone. To identify a *Chlamydia*-specific TCR for the creation of TCR transgenic mice, we generated a *Chlamydia*-specific CD4+ T cell clone named NR9.2. The clone specifically secreted IFNγ when co-cultured with *Chlamydia*-infected macrophages in an intracellular cytokine staining assay (FIG. 13A). In addition, adoptive transfer of this clone protected naïve mice from *Chlamydia* infection (FIG. 13B). A library of proteins expressed by the *C. trachomatis* ORFs contained in the genome database was screened. Of the 894 ORFs we screened, only *E. coli* expressing the protein encoded by CT788 (FIG. 14) stimulated NR9.2 to secrete significant levels of IFNγ (FIG. 15). CT788 was annotated in the published *C. trachomatis* genome as a predicted periplasmic protein of unknown function (Stephens et al., *Science* 282:754-759, 1998), and its sequence shares little homology with proteins outside of the *Chlamydia* genus. CT788 was designated Cta1 (*Chlamydia*-specific T cell antigen-1).

Figure 16A:
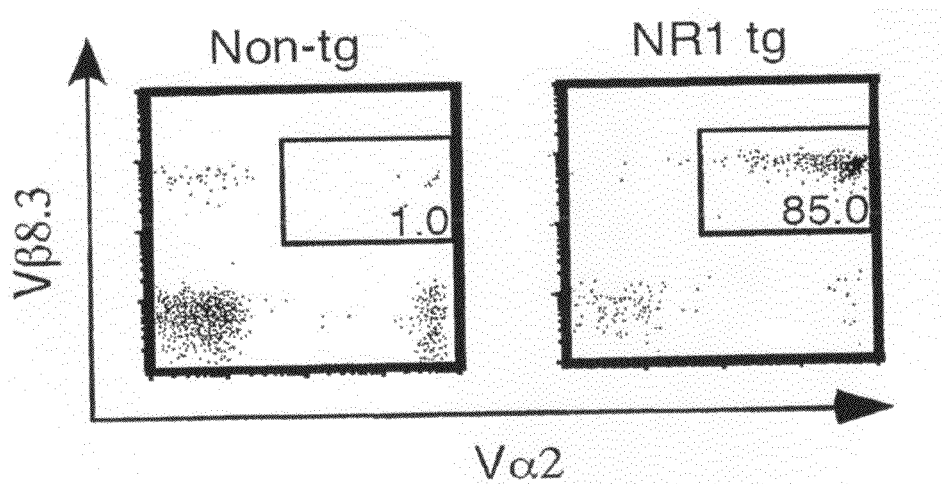
FIG. 16A is a plot showing CD4$^+$ peripheral blood lymphocytes from non-transgenic and NR1 transgenic mice stained for the Vα2 and Vβ8.3 TCR elements expressed by T cell clone NR9.2. Results are gated on live CD4$^+$ cells.

Mice expressing the TCR from the NR9.2 clone. We then generated mice expressing the TCR from the NR9.2 clone. Peripheral blood mononuclear cells from the resulting TCR transgenic mice expressed the same variable chain elements (Vα2, Vβ8.3) as the T cell clone from which they were derived. We cloned the rearranged genomic TCRα and TCRβ sequences from NR9.2 into expression vectors and injected these constructs into C57BL/6 fertilized oocytes. Pseudopregnant female recipients were then implanted with the oocytes and individual pups born from the foster mothers were screened using primers specific for the NR9.2 TCR. A TCR tg founder line was identified and designated NR1. To confirm that the NR9.2 TCR was expressed on the transgenic cells in NR1, cells from the peripheral blood of these animals were tested for expression of the Vα2 and Vβ8.3 TCR elements. Vα2 and Vβ8.3 were the variable chains expressed by the original NR9.2 T cell clone (data not shown). A significant percentage of CD4+ T cells from the peripheral blood of the transgenic mice expressed Vα2 and Vβ38.3 (FIG. 16A), demonstrating that both the TCRα and TCRβ transgenes from NR9.2 were efficiently expressed. The transgenic cells were also CD69$^{lo}$, CD25$^{lo}$, CD62L$^{hi}$, CD44$^{lo}$, and CTLA4$^{lo}$, indicating that they were naïve T cells (data not shown).

Figure 16B:
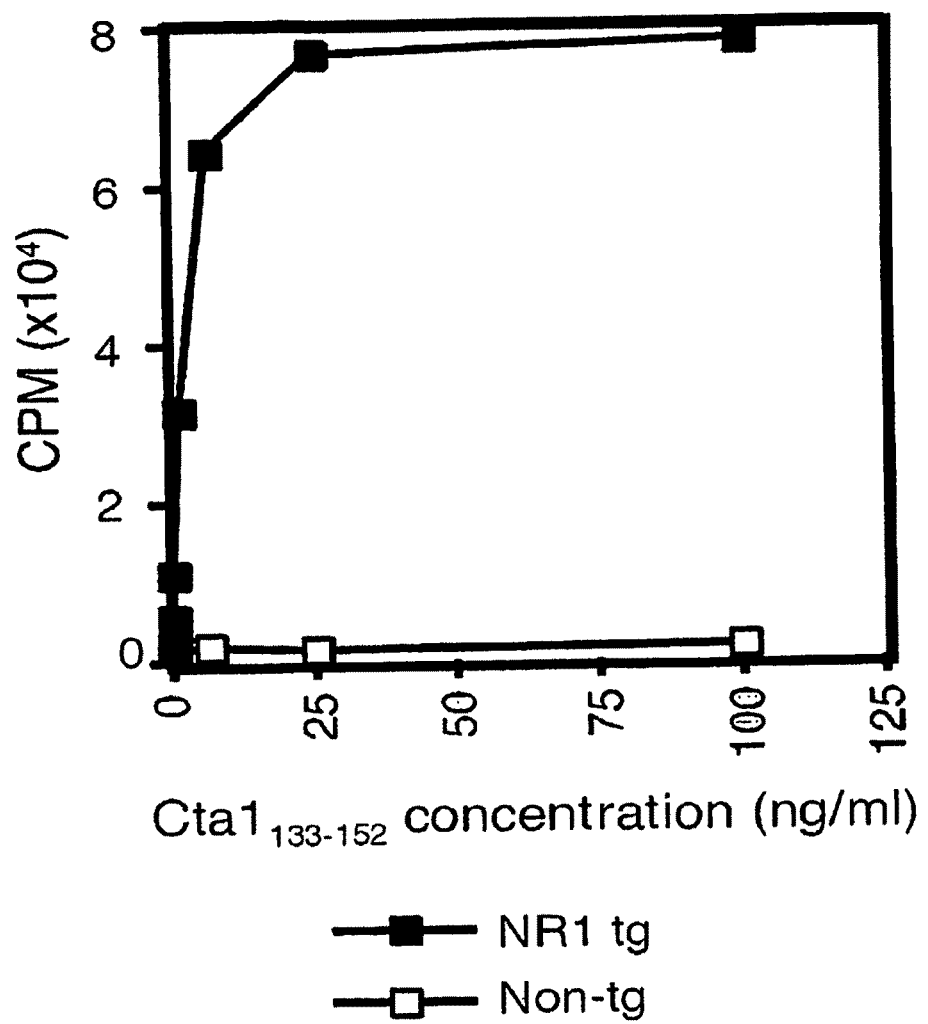
FIG. 16B is a graph showing proliferation of splenocytes from NR1 transgenic or non-transgenic mice in response to the indicated concentrations of Cta1$_{133-152}$ (SEQ ID NO:2). Proliferation was measured by [$^3$H]thymidine incorporation into cells. These results indicate that NR1 TCR tg cells recognize Cta1$_{133-152}$ (SEQ ID NO:2).

To determine whether the NR1 transgenic T cells were specific and responsive to Cta1, we tested the proliferation of transgenic spleen cells in response to Cta1$_{133-152}$ (see FIG. 14; SEQ ID NO:2). Spleen cells from naïve NR1 mice showed a strong proliferative response to Cta1$_{133-152}$ (FIG. 16B). NR1 spleen cells also secreted high levels of IFNγ in response to this peptide (data not shown). In contrast, spleen cells from NR1 did not proliferate in response to a control peptide from ovalbumin, OVA$_{323-336}$ (data not shown).

To determine whether the NR1 transgenic T cells responded to *Chlamydia* in vivo, thirty million cells from the spleen and peripheral lymph nodes of NR1 mice were labeled with the fluorescent dye carboxyfluorescein diacetate succinimidyl ester (CFSE) and adoptively transferred into C57BL/6 recipients. As approximately 10% of NR1 cells were CD4+ T cells expressing the Cta1-specific TCR (data not shown), the transferred population contained approximately 3×10$^6$ Cta1-specific T cells. CFSE-labeled NR1 transgenic cells retained high levels of CFSE following transfer into uninfected recipient mice, indicating that the transgenic cells did not divide in the absence of infection.

Figure 17:
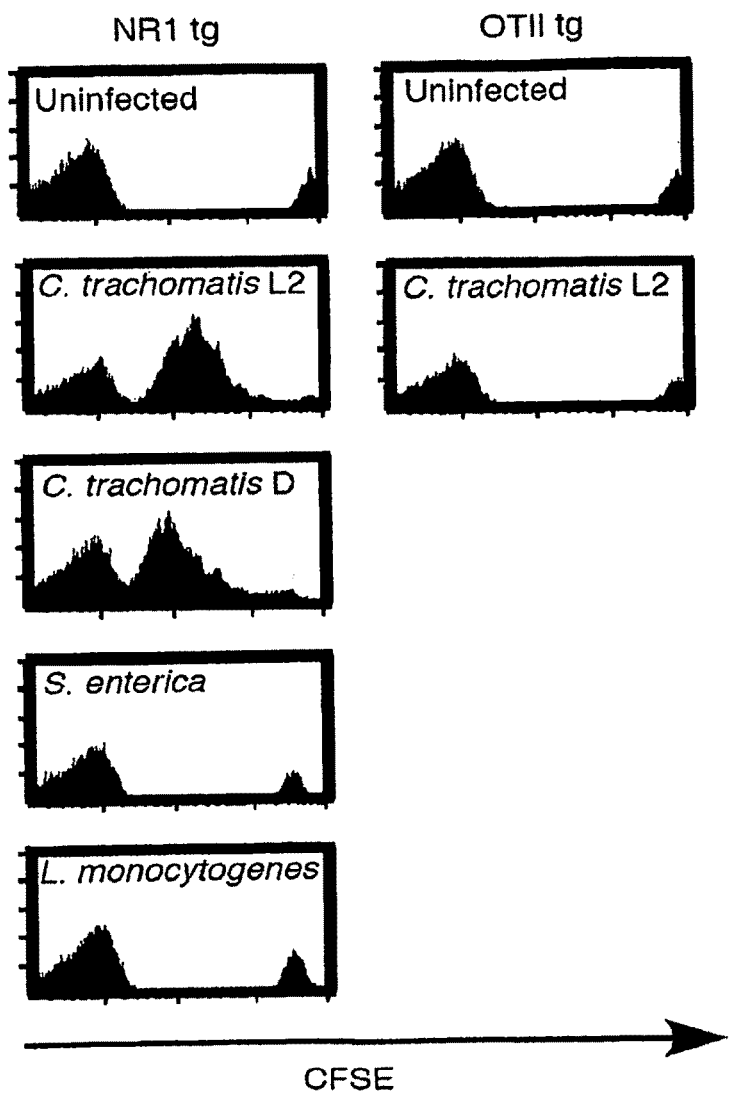
FIG. 17 is a graph showing that the CD4$^+$ T-cell clone (NR9.2) injected into naive mice proliferates following infection by *Chlamydia*. Proliferation of the CFSE-labeled TCR transgenic T-cells is observed as a shift in the transferred population to the left into an arbitrarily set gate. CFSE-labeled NR1 or OTII cells were transferred into C57BL/6 recipients. One day later, mice were infected intravenously with the indicated pathogen. Spleens were harvested three days later. Results were gated on live CD4$^+$Vα2$^+$ cells to detect the NR1 TCR tg cells.

In other C57BL/6 animals that had received the CFSE-labeled transgenic cells, the animals were infected intravenously with 10$^7$ IFU of *C. trachomatis*. The *C. trachomatis* organisms used for infection were serovar L2, which is associated with lymphogranuloma venereum (LGV) in humans, or serovar D, which is associated with typical human genital tract infection. Within three days of infection with either *C. trachomatis* serovar, the transgenic cells had proliferated extensively (FIG. 17). We also observed that the proliferation of NR1 cells was specific for *C. trachomatis* infection. When animals that had received NR1 cells were infected intravenously with *Salmonella enterica* or *Listeria monocytogenes*, the transgenic T cells were not stimulated to proliferate. As an additional control to demonstrate that TCR tg T cells with other specificities would not respond to *C. trachomatis* infection in the recipient mice, we showed that ovalbumin-specific OTII transgenic T cells proliferated in response to ovalbumin protein with adjuvant (data not shown) but not in response to *C. trachomatis* infection (FIG. 17).

Figure 18A:
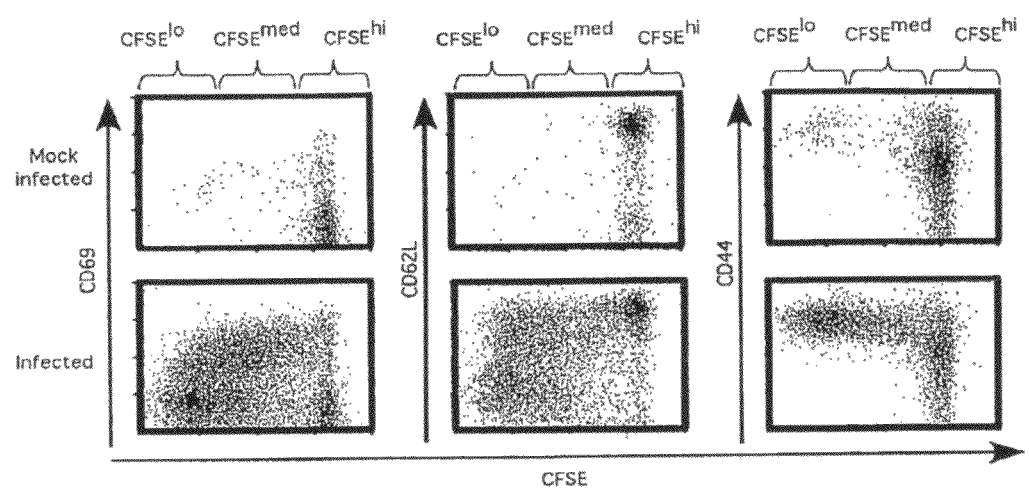
FIG. 18A is a set of plots showing CD69 and CD44 are upregulated and CD62L is downregulated on proliferating transgenic T cells in the draining lymph nodes. Proliferation (reflected as a shift in the population to the left) of CFSE-labeled CD4$^+$ TCR transgenic cells transferred into naive mice was measured 5-7 days after infection of the recipient mice with C. trachomatis serovar L2. CD69 was upregulated on proliferating cells as reflected in a population shift from the bottom of the graph to the top. CD62L was downregulated on proliferating cells as reflected in a population shift from the top of the graph to the bottom. Results are gated on live Thy1.2$^+$CD4$^+$ cells.
Figure 18B:
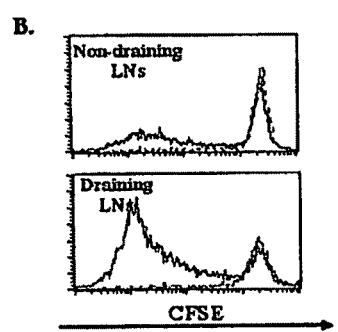
FIG. 18B is a pair of graphs showing transferred TCR transgenic cells begin proliferating extensively at four days post-infection in the lymph nodes draining the genital tract, but not in lymph notes draining other sites. Dotted line represents uninfected mice; the solid line represents infected mice. Results are gated on live Thy1.2$^+$(CD90.2)$^+$CD4$^+$ cells.
Figure 18C:
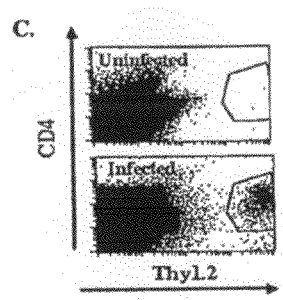
FIG. 18C is a set of plots showing transferred TCR transgenic T cells are recruited to the genital tracts of mice following intrauterine infection with Chlamydia. CFSE-labeled NR1 cells were transferred into CD90.1 recipients and then mock-infected or infected in the uterus with 106 IFU of C. trachomatis serovar L2. Seven days after infection, the genital tracts were removed from the mice and analyzed for the presence of the transferred NR1 cells. The presence of CD90.2$^+$CD4$^+$NR1 cells was compared in the genital tracts of mock infected and infected recipients. Results were gated on live cells. The box shows adoptively transferred T cells in the genital tissue of mice.

To study CD4+ T cell responses to *C. trachomatis* in the context of a mucosal infection, Thy1.1 (CD90.1) recipient mice adoptively transferred with CFSE-labeled transgenic cells were infected in the uterine horns with *C. trachomatis* L2. Using Thy1.1 recipient mice, donor transgenic cells were readily distinguished from endogenous cells in the recipient animals. The activation status of the transgenic cells was assessed by examining cell surface expression of the early activation marker CD69 and the naïve T cell marker CD62L on T cells from iliac lymph nodes (ILNs), which drain antigen from the genital tract (Parr et al., *J. Reprod. Immunol.* 17:101-14, 1990; Cain et al., *Infect. Immunol.* 63:1784-9, 1995; Hawkins et al., *Infect. Immunol.* 68:5587-94, 2000). The ILNs were removed five days after infection and NR1 T cells in the nodes were examined for CD69 upregulation and loss of CFSE fluorescence. Transgenic cells in uninfected mice were predominantly not activated (CD69$^{lo}$) and of the naïve phenotype (CD62L$^{hi}$). Following infection, CD69 was upregulated on cells that had undergone a few rounds of cell division and downregulated on cells that had undergone further rounds of division. CD62L was downregulated on a sub-population of transgenic cells that had extensively divided (FIG. 18A). Whereas T cell proliferation was weak in the non-draining lymph nodes, extensive T cell proliferation was observed four days post-infection in the draining lymph nodes (FIG. 18B). After activation and proliferation, transgenic cells were also recruited to the genital mucosa in infected mice (FIG. 18C).

As shown in FIG. 18A, a significant number of NR1 T cells from infected animals showed progressive dilution of CFSE, suggesting that extensive proliferation had occurred. Furthermore, recently divided (CFSE$^{med}$) NR1 T cells expressed high levels of CD69, indicating that these cells also had been recently activated. Once NR1 cells had undergone extensive proliferation (CFSE$^{lo}$), they expressed lower levels of CD69. These results are consistent with CD69 as an early T cell activation marker that is only transiently upregulated following antigen encounter (Ziegler et al., *Stem Cells* 12:456-65, 1994; Cochran et al., *Immunity* 12:241-50, 2000). Cells from the ILNs of mock infected recipients were CFSE$^{hi}$ and had not upregulated CD69, suggesting that they were not activated. Interestingly, there was a similar population of CFSE$^{hi}$CD69$^{lo}$ NR1 cells in the infected recipients. These could be cells that did not encounter antigen, or they could be cells that were not expressing the appropriate Cta1-specific TCR because of endogenous TCR rearrangements (von Boehmer, *Annu. Rev. Immunol.* 8:531-556, 1990; Balomenos et al., *J. Immunol.* 155:3308-3312, 1995).

Other characteristics of activated T cells include downregulation of the naïve marker CD62L and upregulation of the activation molecule CD44. To confirm that NR1 cells were activated following *Chlamydia* genital infection, the expression of CD62L and CD44 on transferred CFSE-labeled NR1 T cells from the ILNs of recipient mice was analyzed. Seven days after infection, a subset of NR1 T cells that had proliferated extensively (CFSE$^{lo}$) had reduced expression of CD62L (FIG. 18A). By contrast, undivided (CFSE$^{hi}$) NR1 cells in both mock infected and infected recipients were mostly CD62L$^{hi}$. In addition to displaying a CD62L$^{lo}$ phenotype, effector T cells typically express high levels of the activation marker CD44. Proliferating NR1 T cells from the ILNs of infected recipients were exclusively CD44$^{hi}$ (FIG. 18A). Thus, NR1 cells were activated and proliferated in the ILNs of mice following genital infection with *Chlamydia*.

Extensive proliferation of NR1 cells occurs preferentially in the ILNs. To confirm that activation and proliferation of NR1 cells in the ILNs resulted from antigen draining from the genital tract to these nodes, the response of NR1 cells in the ILNs was compared to the response in the lymph nodes that do not drain the genital tract (nondraining lymph nodes, NDLNs). T cell activation and proliferation was monitored over time to ensure that any activity that may have occurred in the NDLNs over the course of infection would be observed. 3×10$^7$ CFSE-labeled NR1 cells were transferred into CD90.1 mice. The mice were then infected in the uterus with 10$^6$ IFU *C. trachomatis* serovar L2. Lymph nodes were then harvested at various times following infection. In the ILNs, upregulation of CD69 was seen on NR1 cells beginning three days after infection. Four days after infection, downregulation of CD62L and upregulation of CD44 was observed. Acquisition of the activation markers occurred preferentially in NR1 cells from the ILNs and not in NR1 cells from the NDLNs (data not shown). Thus, NR1 cells were specifically activated in the ILNs following genital infection with *Chlamydia*.

Figure 19:
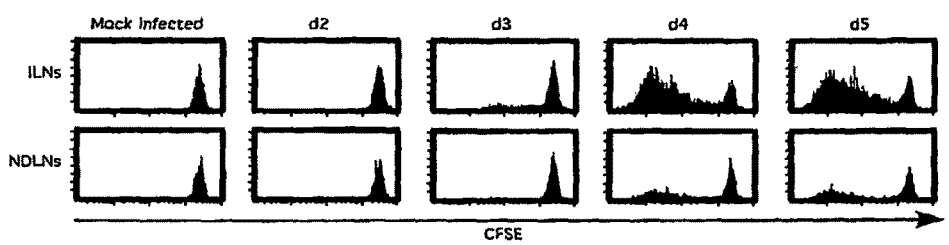
FIG. 19 is a set of graphs showing that NR1 cells proliferate preferentially in the ILNs following intrauterine infection with C. trachomatis. CFSE-labeled NR1 cells were transferred into CD90.1 recipients, which were then mock infected or infected in the uterus with $10^6$ IFU of C. trachomatis serovar L2. ILNs and NDLNs were harvested at the indicated times post-infection and proliferation of CD4$^+$ NR1 cells was examined. Results were gated on live CD90.2$^+$ CD4$^+$ V$\alpha$2$^+$ cells to specifically detect the NR1 TCR tg cells.

By monitoring proliferation of the transferred NR1 cells at various times following infection, we confirmed that NR1 cells preferentially encountered antigen in the ILNs. In the ILNs, NR1 cells were predominantly CFSE$^{hi}$ two and three days post infection, suggesting that these cells had not proliferated at these early time points (FIG. 19), but NR1 cells in the ILNs had proliferated extensively within four days of infection. While NR1 cells had also proliferated in the NDLNs within four days of infection, the number was significantly less than that seen in the ILNs. The proliferating NR1 cells in the NDLNs contained lower levels of CFSE and did not express significant levels of CD69 relative those in the ILNs (data not shown), suggesting that these cells migrated to the NDLNs from other sites following activation. Significant expansion of NR1 T cells in the NDLNs did not occur even one week after infection (data not shown), again demonstrating that proliferation of NR1 cells occurred preferentially in the ILNs.

Figure 20:
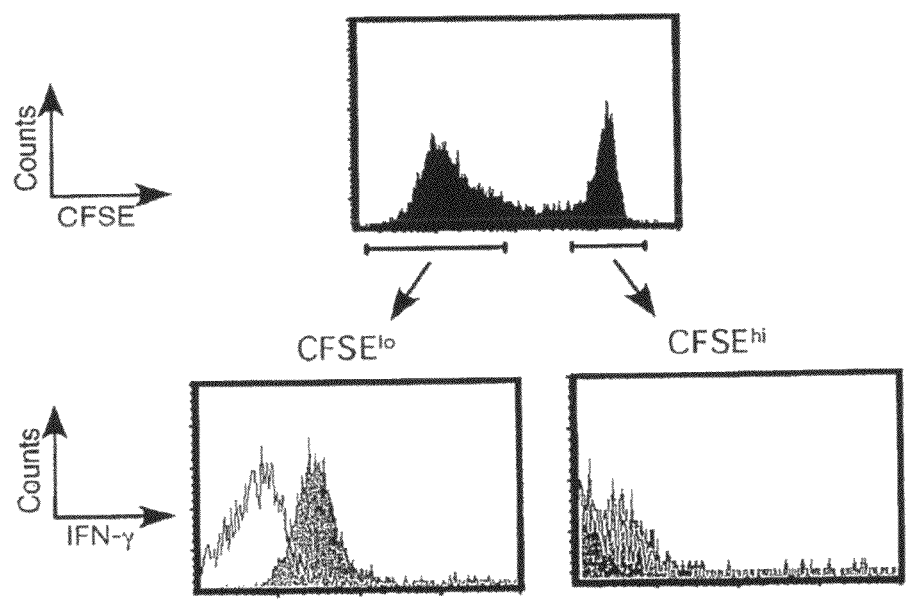
FIG. 20 is a set of graphs showing that NR1 cells differentiate into Th1 cells. CFSE-labeled NR1 cells were transferred into CD90.1 recipients which were then infected in the uterus with $10^6$ IFU of C. trachomatis serovar L2. Six days later, cells from the ILNs were stimulated with PMA/ionomycin and examined for intracellular IFN$\gamma$ by flow cytometry. Cta1-specific T cells (CD90.2$^+$CD4$^+$) were gated on CFSE$^{lo}$ and CFSE$^{hi}$ cells, and intracellular IFN$\gamma$ levels in these two populations were compared. Solid lines represent isotype control; gray filled histograms indicate IFN$\gamma$.

NR1 cells in the ILNs develop the ability to secrete IFNγ. To examine the differentiation of antigen-activated NR1 cells into effector T cells, we determined that proliferating NR1 cells secreted effector cytokines in response to *C. trachomatis* infection. 3×10$^7$ CFSE-labeled NR1 cells were transferred into CD90.1 congenic mice, and then these mice were infected in the uterus with 10$^6$ IFU of *C. trachomatis* serovar L2. The ILNs were removed six days later, and the NR1 T cells were analyzed by flow cytometry for production of cytokines. Proliferating NR1 cells) (CFSE$^{lo}$) secreted IFNγ whereas non-proliferating cells (CFSE$^{hi}$) did not secrete IFNγ (FIG. 20). The NR1 cells did not secrete IL-4 (data not shown). Thus, NR1 cells differentiated preferentially into effector T cells of the Th1 phenotype following genital infection with *Chlamydia*.

Figure 21A:
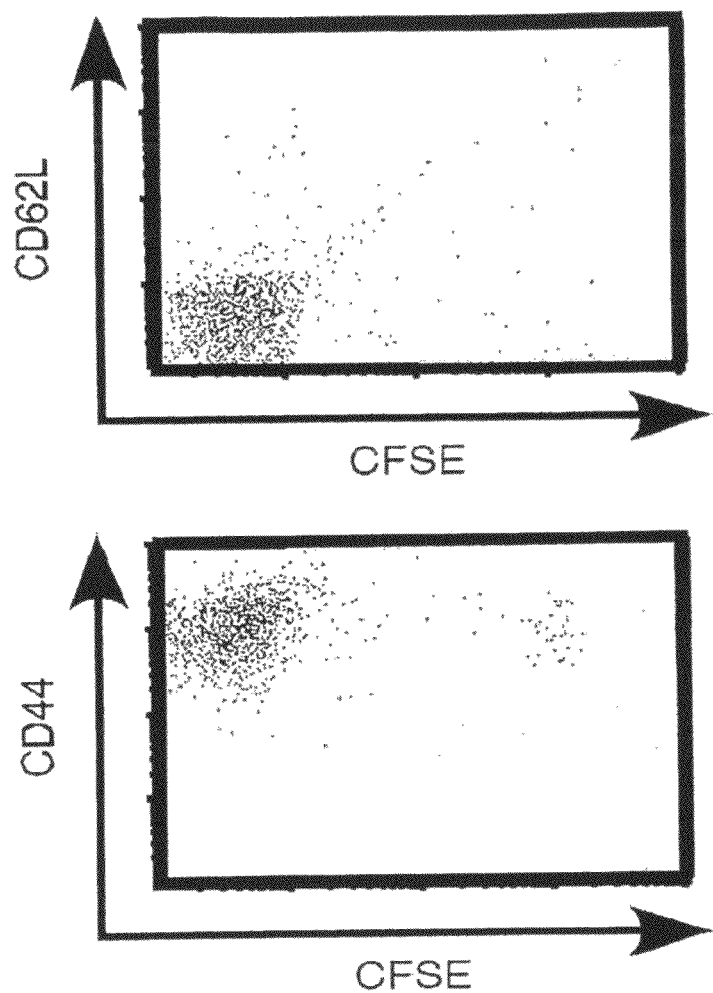
FIG. 21A is a set of graphs showing the levels of CD62L, CD44, and CFSE on NR1 cells in the genital tracts of mock infected and infected mice. Results were gated on live CD90.2$^+$CD4$^+$ cells to specifically detect the NR1 TCR tg cells.
Figure 21B:
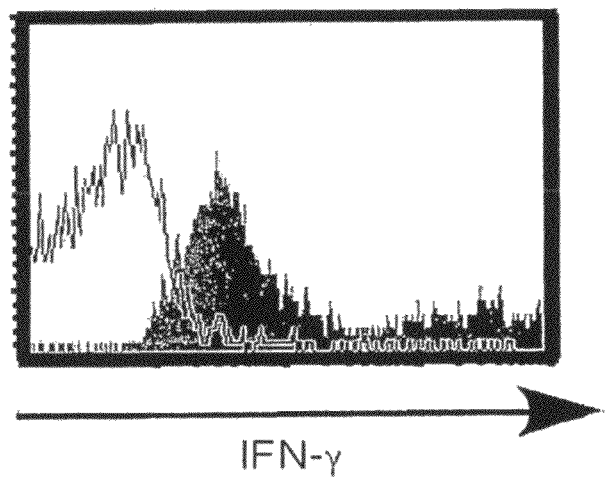
FIG. 21B is a graph showing NR1 cells from the genital tract stimulated with PMA/ionomycin and analyzed by flow cytometry to detect production of IFN$\gamma$. Results are gated on live CD90.2$^+$ CD4$^+$ cells to detect the NR1 TCR tg cells specifically. The solid line represents the isotype control; the filled histogram represents IFN$\gamma$.

Antigen-experienced NR1 cells traffic to the genital tract. Following activation, effector T cells are typically recruited to the site of infection where they contribute to the elimination of the pathogen (Swain et al., *Adv. Exp. Med. Biol.* 512:113-120, 2002; Gallichan et al., *J. Exp. Med.* 184:1879-1890, 1996). To determine whether *Chlamydia*-specific NR1 cells migrated to the site of genital infection in mice, 3×10$^7$ CFSE-labeled NR1 cells were transferred into CD90.1 congenic mice. These recipients were infected in the uterus with $10^6$ IFU of C. trachomatis serovar L2. Genital tract tissue was then isolated and the presence of transferred Chlamydia-specific T cells was determined. Significantly more NR1 cells were observed in the genital mucosa of animals infected with C. trachomatis than in animals that were mock infected (FIG. 18C). Transgenic cells that were recruited to the genital tract had the phenotype of antigen-experienced cells (CFSE$^{lo}$ CD62L$^{lo}$ CD44$^{hi}$) and secreted IFNγ (FIGS. 21A and 21B). In summary, activated NR1 TCR tg T cells that secrete IFNγ are recruited to the genital mucosa in response to C. trachomatis infection.

Antigenic Fragments of Cta1

Figure 22:
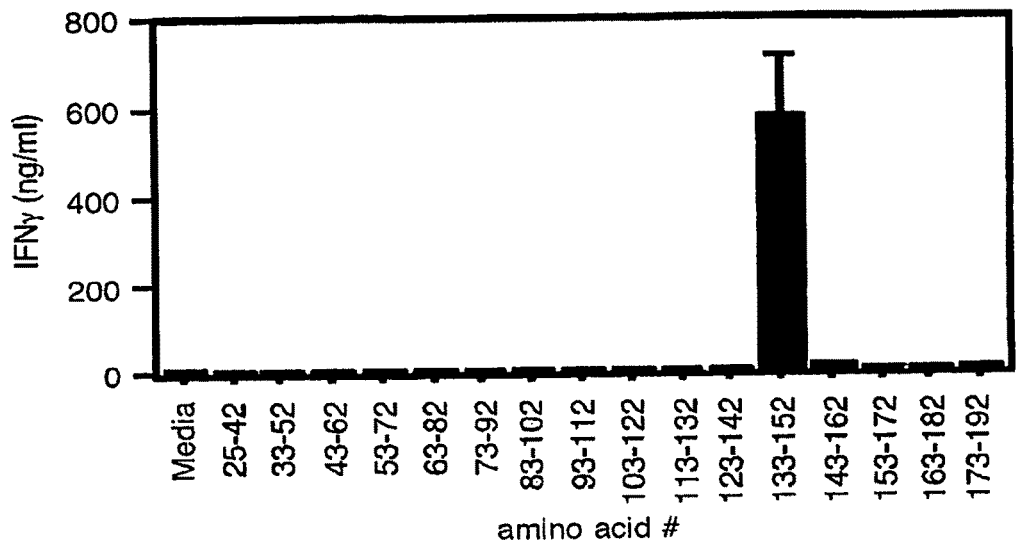
FIG. 22 is a graph showing T cell clone NR9.2 recognizes the novel T cell antigen Cta1$_{133-152}$ (SEQ ID NO:2). The antigenic peptide from Cta1 was mapped by testing overlapping 20-mer synthetic peptides for their ability to stimulate NR9.2 to secrete IFN$\gamma$. Only Cta1$_{133-152}$ stimulated NR9.2 to secrete significant levels of IFN$\gamma$ in an IFN$\gamma$ ELISA. Shown below is the protein sequence of Cta1 (SEQ ID NO:1) with Cta1$_{133-452}$ (SEQ ID NO:2) underlined.

To map more closely the epitope within Cta1 recognized by the NR9.2 T cells, a series of overlapping 20-mer peptides covering the Cta1 sequence for their ability to stimulate NR9.2 to secrete IFNγ were screened (Table 2). The 20-mer peptide Cta1$_{133-152}$ (KGIDPQELWVWICKOMPNWEK; SEQ ID NO:2) induced NR9.2 to secrete significant levels of IFNγ (FIG. 22), confirming the specificity of these C. trachomatis-specific T cells to an epitope within these 20 amino acids.

TABLE 2

Antigen/T cell line, peptide, and IFNγ measured (ng) (SEQ ID NOS: 2 and 156-171)

| Cta1/NR9.2 | LESTSLYKKAGCANKKNRNL | 0.4 (±0.2) |
|---|---|---|
| | GCANKKNRNLIGWFLAGMFF | 0.5 (±0.3) |
| | IGWFLAGMFFGIFAIIFLLI | 0.6 (±0.3) |
| | GIFAIIFLLILPPLPSSTQD | 0.4 (±0.2) |
| | LPPLPSSTQDNRSMDQQDSE | 0.6 (±0.2) |
| | NRSMDQQDSEEFLLQNTLED | 0.6 (±0.3) |
| | EFLLQNTLEDSEIISIPDTM | 0.6 (±0.2) |
| | SEIISIPDTMNQIAIDTEKW | 0.6 (±0.2) |
| | NQIAIDTEKWFYLNKDYTNV | 0.5 (±0.2) |
| | FYLNKDYTNVGPISIVQLTA | 0.7 (±0.4) |
| | GPISIVQLTAFLKECKHSPE | 0.5 (±0.3) |
| | FLKECKHSPEKGIDPQELWV | 0.5 (±0.4) |
| | KGIDPQELWVWKKGMPNWEK | 58.0 (±14.0) |
| | WKKGMPNWEKVKNIPELSGT | 1.4 (±0.2) |
| | VKNIPELSGTVKDESPSFLV | 0.8 (±0.1) |
| | VKDESPSFLVQSGVAGLEQL | 0.7 (±0.2) |
| | QSGVAGLEQLESI | 0.8 (±0.2) |

By screening deletion peptides of this 20-mer, a minimal sequence required for activation of the NR9.2 can be identified. Epitopic sequences can include 3, 4, 5, 6, 7, 8, 9, 10, 11, 12, 13, 14, 15, 16, 17, 18, and 19 amino acid fragments of Cta1$_{133-152}$ and can include N-terminal or C-terminal deletions of the Cta1$_{133-152}$ fragment, or a combination of N- and C-terminal deletions (see, e.g., Table 1). Further, antigenic peptides in other regions of Cta1 or using other T cell clones can also be identified similarly. Compositions and methods of the invention may include or employ combinations of epitopic fragments described herein. Antigenicity of Cta1 fragments can be determined using methods known in the art and methods described herein.

The experiments described above were performed as follows.

Mice. C57BL/6J (H-2$^b$), B6.PL-thy1$^a$0Cy (CD90.1 congenic), and OTII mice were obtained from the Jackson Laboratory.

Tissue culture. Bone marrow derived dendritic cells (BM-DCs) and bone marrow derived macrophages (BMMs) were cultured as previously described (Steele et al., J. Immunol. 173:6327-6337, 2004; Shaw et al., Infect. Immunol. 74:1001-1008, 2006).

Growth, isolation, and detection of bacteria. Elementary bodies (EBs) of C. trachomatis serovar L2 434/Bu and C. trachomatis serovar D (UW-3/Cs) were propagated and quantitated as previously described (Starnbach et al., J. Immunol. 171:4742-4749, 2003). Salmonella enterica serovar Typhimurium (ATCC 14028) was grown at 37° C. in Luria-Bertani (LB) medium. Listeria monocytogenes 10403s was grown at 30° C. in brain heart infusion (BHI) medium (Difco/Becton Dickinson, Sparks, Md.).

Generation of the NR9.2 T cell clone. Splenocytes from mice were isolated 21 days after infection with C. trachomatis serovar L2 and were cultured with irradiated (2,000 rads) BMDCs, UV-inactivated C. trachomatis serovar L2, and naïve syngeneic splenocytes in RP-10 (RPMI 1640 supplemented with 10% FCS, L-glutamine, HEPES, 50 μM 2-βME, 50 U/ml penicillin, and 50 μg/ml streptomycin) with α-methyl mannoside and 5% supernatant from concanavalin A-stimulated rat spleen cells. CD8$^+$ T cells were depleted from the culture using Dynabeads Mouse CD8 (Invitrogen). The CD4$^+$ T cells were restimulated every seven days with C. trachomatis-pulsed BMDCs. Once a C. trachomatis-specific CD4$^+$ T cell line was established, the T cell clone NR9.2 was isolated by limiting dilution.

Identification of the T cell antigen Cta1. An expression library of genomic sequences from C. trachomatis serovar D was inserted into a modified form of the pDEST17 vector (Invitrogen) and transformed into the Stb12 strain of E. coli (Invitrogen). Following induction of protein expression, the bacteria were fixed in 0.5% paraformaldehyde and incubated with BMMs. NR9.2 T cells were then added and after 24 h, the supernatant was tested for the level of IFNγ by ELISA (Endogen, Rockford, Ill.). To identify the reactive peptide epitope within Cta1, synthetic 20-mer peptides (MIT Biopolymers Lab, Cambridge, Mass.) were used at a concentration of 25 μM in an IFNγ ELISA (Endogen).

Flow cytometry and antibodies. Antibodies specific for CD4, CD90.2, Vα2, Vβ8.3, CD69, CD25, CD44, CD62L, CTLA-4, IFNγ, and IL-4 were purchased from BD Biosciences (San Diego, Calif.). Data were collected on a BD Biosciences FACSCalibur™ flow cytometer (San Jose, Calif.) and analyzed using CellQuest™ software. Intracellular cytokine staining was performed by incubating NR9.2 T cells with Chlamydia-infected BMMs (MOI 5:1) in the presence of GolgiPlug™ reagent (BD Biosciences). Intracellular cytokine staining of NR1 transgenic cells was performed by stimulating cells for 4 hours in the presence of PMA (50 ng/ml, MP Biomedicals, Solon, Ohio), ionomycin (1 μg/ml, Sigma, St. Louis, Mo.), and GolgiPlug™ reagent (BD Biosciences). Cells were permeabilized with the Cytofix/Cytoperm Plus kit (BD Biosciences). PE-conjugated rat IgG1 (BD Biosciences) was used as an isotype control antibody.

Generation of NR1 TCR tg mice. The rearranged TCR from NR9.2 uses the Vα2Jα16 and Vβ8.3DJβ1.2 receptor chains. The genomic TCR sequences were cloned and inserted into the TCR vectors pTα and pTβ at the recommended restriction sites (Kouskoff et al., J. Immunol. Methods 180:273-80, 1995). Prokaryotic DNA sequences were then removed from both vectors prior to injection into the pronuclei of fertilized C57BL/6J oocytes. TCR transgenic founders were identified by PCR. Routine screening to identify transgenic mice was carried out by staining samples of orbital blood from the mice with antibodies specific for Vα2 and Vβ8.3, followed by flow cytometry.

Adoptive transfer of NR1 cells, infection of mice, and preparation of tissues from mice. Spleen and peripheral lymph nodes were isolated from NR1 TCR tg mice and labeled with the dye CFSE (5 μM, Molecular Probes, Eugene, Ore.). Recipient mice were injected i.v. with $3\times10^7$ NR1 cells. Mice were infected one day after transfer of the cells. Where indicated, mice were infected intravenously with $10^7$ IFU of C. trachomatis, $3\times10^3$ CFU of L. monocytogenes, or $5\times10^3$ CFU of S. enterica. To infect the genital tract, mice were treated with 2.5 mg of medroxyprogesterone acetate subcutaneously one week prior to infection to synchronize the mice into a diestrus state (Perry et al., Infect. Immunol. 67:3686-3689, 1999; Ramsey et al., Infect. Immunol. 67:3019-3025, 1999). Intrauterine infection was carried out by inoculating the uterine horns with $10^6$ IFU of C. trachomatis serovar L2. At various times after infection, single-cell suspensions of spleen, ILNs, or NDLNs taken from the axillary and cervical lymph nodes were prepared, stained, and analyzed by flow cytometry as described above. To isolate lymphocytes from the genital mucosa, genital tracts (oviduct, uterus, and cervix) were removed from mice and digested with collagenase (type XI, Sigma) for one hour prior to staining and flow cytometry.

Intracellular cytokine staining. Bone marrow-derived macrophages were infected with C. trachomatis L2 at an MOI of 5:1 for 16-18 hours. T cells were added at an effector-to-target ratio of 5:1 and incubated for another 6 hours in the presence of brefeldin A (Pharmingen). Cells were permeabilized and stained for the presence of IFNγ. Cells were then analyzed using standard flow cytometric techniques on a FACScan flow cytometer.

Protection assay. Ten days after T cell restimulation, $10^7$ T cells were washed twice with PBS and adoptively transferred into C57BL/6 recipient mice. Mice were then infected i.v. with $10^7$ IFUs C. trachomatis L2. Spleens were titered three days later on a McCoy cell monolayer. As controls, naïve mice and Chlamydia-immune mice were also infected with C. trachomatis L2 and spleens were titered three days later.

Intrauterine infection. Intrauterine infection with C. trachomatis was carried out by surgical inoculation of the uterine horns with $10^6$ IFUs C. trachomatis L2. Draining (iliac) and non-draining (axillary, cervical, mandibular) lymph nodes were harvested and single cell suspensions were analyzed using standard flow cytometric techniques on a FACScan flow cytometer.

CT788 Polypeptide Expression

A CT788 polypeptide or fragment thereof may be produced by transformation of a suitable host cell with all or part of a polypeptide-encoding polynucleotide molecule or fragment thereof in a suitable expression vehicle.

Those skilled in the field of molecular biology will understand that any of a wide variety of expression systems may be used to provide the polypeptide CT788 or fragment thereof. The precise host cell used is not critical to the invention. The CT788 polypeptide or fragment thereof may be produced in a prokaryotic host (e.g., E. coli) or in a eukaryotic host (e.g., Saccharomyces cerevisiae, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (Pouwels, P. H. et al., 1985, Supp. 1987).

Once the recombinant CT788 polypeptide or fragment thereof is expressed, it is isolated, e.g., using affinity chromatography. In one example, an antibody raised against a CT788 polypeptide or fragment thereof may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant CT788 polypeptide or fragment thereof can, if desired, be further purified, e.g., by high performance liquid chromatography (see, e.g., Fisher, Laboratory Techniques In Biochemistry And Molecular Biology, eds., Work and Burdon, Elsevier, 1980).

Short fragments of CT788, can also be produced by chemical synthesis (e.g., by the methods described in Solid Phase Peptide Synthesis, 2nd ed., 1984 The Pierce Chemical Co., Rockford, Ill.).

Also included in the invention are CT788 proteins or fragments thereof fused to heterologous sequences, such as detectable markers (for example, proteins that may be detected directly or indirectly such as green fluorescent protein, hemagglutinin, or alkaline phosphatase), DNA binding domains (for example, GAL4 or LexA), gene activation domains (for example, GAL4 or VP16), purification tags, or secretion signal peptides. These fusion proteins may be produced by any standard method. Fusion protein may also include fusions to immunogenic proteins such as an Ig protein, e.g., as IgG, IgM, IgA, or IgE or the Fc region of an Ig protein. For production of stable cell lines expressing a CT788 fusion protein, PCR-amplified CT788 nucleic acids may be cloned into the restriction site of a derivative of a mammalian expression vector. For example, KA, which is a derivative of pcDNA3 (Invitrogen, Carlsbad, Calif.) contains a DNA fragment encoding an influenza virus hemagglutinin (HA). Alternatively, vector derivatives encoding other tags, such as c-myc or poly Histidine tags, can be used.

Other sequences that may be fused to CT788 include those that provide immunostimulatory function, such as interleukin-2 (Fan et al., Acta Biochim. Biophys. Sin. 38:683-690, 2006), Toll-like receptor-5 flagellin (Huleatt et al., Vaccine 8:763-775, 2007), simian immunodeficiency virus Tat (Chen et al., Vaccine 24:708-715, 2006), or fibrinogen-albumin-IgG receptor of group C streptococci (Schulze et al., Vaccine 23:1408-1413, 2005). In addition, heterologous sequences may be added to enhance solubility or increase half-life, for example, hydrophilic amino acid residues (Murby et al., Eur. J. Biochem. 230:38-44, 1995), glycosylation sequences (Sinclair and Elliott, J. Pharm. Sci. 94:1626-1635, 2005), or the carboxy terminus of human chorionic gonadotropin or thrombopoeitin (Lee et al., Biochem. Biophys. Res. Comm. 339: 380-385, 2006).

Vaccine Production.

The invention also provides for a vaccine composition including a CT788 polypeptide, an fragment (e.g., an immunogenic fragment) of CT788, any polypeptide identified in a method of the invention, or an fragment (e.g., an immunogenic fragment) thereof. The vaccine may further include an additional antigenic peptide fragment (e.g., 2, 3, 4, 5, 6, 10, or more different fragments). The invention further includes a method of inducing an immunological response in an individual, particularly a human, the method including inoculating the individual with a CT788 polypeptide or a fragment or fragments thereof (e.g., an immunogenic fragment), in a suitable carrier for the purpose of inducing an immune response to protect an individual from infection, particularly bacterial infection, and most particularly Chlamydia infection. The administration of this immunological composition may be used either therapeutically in individuals already experiencing an infection, or may be used prophylactically to prevent an infection.

The preparation of vaccines that contain immunogenic polypeptides is known to one skilled in the art. The CT788 polypeptide, fragment of a CT788 polypeptide, polypeptide identified in a method of the invention, or fragment thereof may serve as an antigen for vaccination, or an expression vector encoding the polypeptide, or fragments or variants thereof, might be delivered in vivo in order to induce an immunological response comprising the production of antibodies or, in particular, a T cell immune response.

A CT788 polypeptide, polypeptide identified in a method of the invention, or fragment or variant thereof may be fused to a recombinant protein that stabilizes the polypeptide, aids in its solubilization, facilitates its production or purification, or acts as an adjuvant by providing additional stimulation of the immune system. The compositions and methods comprising the polypeptides or nucleotides of the invention and immunostimulatory DNA sequences are described in (Sato et al., Science 273:352, 1996).

Typically vaccines are prepared in an injectable form, either as a liquid solution or as a suspension. Solid forms suitable for injection may also be prepared as emulsions, or with the polypeptides encapsulated in liposomes. Vaccine antigens are usually combined with a pharmaceutically acceptable carrier, which includes any carrier that does not induce the production of antibodies harmful to the individual receiving the carrier. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

Adjuvants are immunostimulating agents that enhance vaccine effectiveness. Effective adjuvants include, but are not limited to, aluminum salts such as aluminum hydroxide and aluminum phosphate, muramyl peptides (e.g., muramyl dipeptide), bacterial cell wall components, saponin adjuvants, and other substances that act as immunostimulating agents to enhance the effectiveness of the composition. Other adjuvants include liposomal formulations, synthetic adjuvants, such as saponins (e.g., QS21), monophosphoryl lipid A, and polyphosphazine.

Immunogenic compositions of the invention, e.g., the CT788 polypeptide, a CT788 fragment, polypeptide identified in a method of the invention, or a fragment thereof, a pharmaceutically acceptable carrier, and adjuvant, also typically contain diluents, such as water, saline, glycerol, ethanol. Auxiliary substances may also be present, such as wetting or emulsifying agents, pH buffering substances, and the like. Proteins may be formulated into the vaccine as neutral or salt forms. The vaccines are typically administered parenterally, by injection; such injection may be subcutaneous, intradermal, intramuscular, intravenous, or intraperitoneal. Additional formulations are suitable for other forms of administration, such as by suppository or orally. Oral compositions may be administered as a solution, suspension, tablet, pill, capsule, or sustained release formulation. Vaccines may also be administered by an ocular, intranasal, gastric, pulmonary, intestinal, rectal, vaginal, or urinary tract route. The administration can be achieved in a single dose or repeated at intervals. The appropriate dosage depends on various parameters that are understood by those skilled in the art, such as the nature of the vaccine itself, the route of administration, and the condition of the mammal to be vaccinated (e.g., the weight, age, and general health of the mammal).

In addition, the vaccine can also be administered to individuals to generate polyclonal antibodies (purified or isolated from serum using standard methods) that may be used to passively immunize an individual. These polyclonal antibodies can also serve as immunochemical reagents.

Antigenic peptides (e.g., CT788 peptides such as those described herein including $CT788_{133-152}$ or any fragment thereof) may also be administered as fusion peptides. For example, a polypeptide or polypeptide derivative may be fused to a polypeptide having adjuvant activity, such as, e.g., subunit B of either cholera toxin or E. coli heat-labile toxin. Several possibilities are can be used for achieving fusion. First, the polypeptide of the invention can be fused to the N- or C-terminal end of the polypeptide having adjuvant activity. Second, a polypeptide fragment can be fused within the amino acid sequence of the polypeptide having adjuvant activity.

Pharmaceutical Compositions

In addition to vaccines, the invention also provides pharmaceutical compositions that include a polypeptide or a fragment thereof identified using a method of the invention or compositions that include at CT788 polypeptide or a fragment thereof (e.g., an immunogenic fragment or any fragment described herein). Such compositions may be incorporated into a pharmaceutical composition, dispersed in a pharmaceutically-acceptable carrier, vehicle or diluent. In one embodiment, the pharmaceutical composition includes a pharmaceutically-acceptable excipient. The compounds of the present invention may be administered by any suitable means, depending, for example, on their intended use, as is well known in the art, based on the present description. For example, if compounds of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compounds of the present invention may be formulated as eye drops or eye ointments. These formulations may be prepared by conventional means, and, if desired, the compounds may be mixed with any conventional additive, such as an excipient, a binder, a disintegrating agent, a lubricant, a corrigent, a solubilizing agent, a suspension aid, an emulsifying agent or a coating agent.

Subject compounds may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of agent that may be combined with a carrier material to produce a single dose vary depending upon the subject being treated, and the particular mode of administration.

Pharmaceutical compositions of this invention suitable for parenteral administration includes one or more components of a supplement in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Methods of Treating a Pathogenic Disease or Neoplasm

The polypeptides, vaccines, and pharmaceutical compositions described herein may be used in a variety of treatments of diseases including a pathogenic infection and in the treatment of a neoplastic disorder. Those skilled in the art will understand, the dosage of any composition described herein will vary depending on the symptoms, age and body weight of the patient, the nature and severity of the disorder to be treated or prevented, the route of administration, and the form of the supplement. Any of the subject formulations may be administered in any suitable dose, such as, for example, in a single dose or in divided doses. Dosages for the compounds of the present invention, alone or together with any other compound of the present invention, or in combination with any compound deemed useful for the particular disorder, disease or condition sought to be treated, may be readily determined by techniques known to those of skill in the art. Also, the present invention provides mixtures of more than one subject compound, as well as other therapeutic agents.

The combined use of several compounds of the present invention, or alternatively other therapeutic agents, may reduce the required dosage for any individual component because the onset and duration of effect of the different components may be complimentary. In such combined therapy, the different active agents may be delivered together or separately, and simultaneously or at different times within the day.

Therapeutic Antibodies and T-Cell Depletion

Alternatively, the immune response to *Chlamydia*, rather than the infection itself, may be responsible for symptoms which accompany infection, including sterility and pelvic inflammatory disease. In this case, it may be desirable to limit the immune response by a subset of CD4$^+$ or CD8$^+$ T-cells within an infected individual. Antibodies targeted towards T-cell clones identified in the methods of the invention (e.g., antibodies specific to $CD4^+$ cells targeted to CT788) may therefore be useful in treating or preventing deleterious effects associated with *Chlamydia* infection. Methods for selective depletion of specific populations of T-cell are described, for example, in Weinberg et al., *Nat. Med.* 2(2): 183-189, 1996.

All patents, patent applications, and publications mentioned in this specification are herein incorporated by reference to the same extent as if each independent patent, patent application, or publication was specifically and individually indicated to be incorporated by reference.

What is claimed is:

1. A method of determining whether a member of a library contains or encodes an immunogenic polypeptide, wherein said library comprises at least 20 discrete members in defined locations and said members each comprise a cell or virus comprising a pre-determined open reading frame from the genome of a pathogenic organism, said pre-predetermined open reading frame operably linked to a promoter, said method comprising:
   (a) individually contacting a member of said library with a second cell capable of (i) endocytosing said cell or said virus and (ii) displaying a polypeptide encoded by said pre-determined open reading frame on its surface through the major histocompatibility complex (MHC) class I pathway;
   (b) individually contacting said second cell from step (a) with a cytotoxic T lymphocyte (CTL) cell derived from a mammal previously infected with said pathogenic organism; and
   (c) detecting whether said CTL cell is activated, wherein activation of said CTL cell indicates that said member of said library contains said pre-determined open reading frame which encodes at least a portion of said immunogenic polypeptide.

2. The method of claim 1, wherein said member of said library further comprises a polynucleotide encoding a pore-forming protein.

3. The method of claim 2, wherein said pore-forming protein is listeriolysin O (LLO).

4. The method of claim 1, wherein said second cell is a macrophage.

5. The method of claim 1, wherein said member of said library is killed prior to said contacting step (a).

6. The method of claim 1, wherein prior to said contacting step (b), said second cell is killed.

7. The method of claim 1, further comprising step:
   (d) recovering said polypeptide identified in step (c) from a replica copy of said library.

8. The method of claim 1, wherein, prior to said contacting step (a), a replica of said library is made.

9. The method of claim 1, further comprising step:
   (d) identifying an epitope sufficient for CTL activation within said polypeptide determined to be immunogenic in step (c).

10. The method of claim 1, wherein said members of said library comprise polypeptides from at least 75% of the proteome of said pathogenic organism.

11. The method of claim 10, wherein said members of said library comprise polypeptides from at least 90% of the proteome of said pathogenic organism.

12. The method of claim 11, wherein said members of said library comprise polypeptides from at least 95% of the proteome of said pathogenic organism.

13. The method of claim 1, wherein said contacting step (b) is performed using a plurality of CTL cells.

14. The method of claim 1, further comprising performing steps (b) and (c) at least one further time using said library.

15. The method of claim 14, wherein a different CTL cell is contacted in step (b) each time said method is performed.

16. The method of claim 1, wherein said pre-determined open reading frames include an N-terminal and a C-terminal tag.

17. The method of claim 1, wherein said library includes at least 10% of the open reading frames present in the genome of the pathogenic organism.

18. The method of claim 1, wherein said library includes at least 20% of the open reading frames present in the genome of the pathogenic organism.

19. The method of claim 1, wherein said library includes at least 50% of the open reading frames present in the genome of the pathogenic organism.

* * * * *

SEQUENCE LISTING

```
<160> NUMBER OF SEQ ID NOS: 171

<210> SEQ ID NO 1
<211> LENGTH: 166
<212> TYPE: PRT
<213> ORGANISM: Chlamydia trachomatis

<400> SEQUENCE: 1

Met Asn Ser Gly Met Phe Pro Phe Thr Phe Phe Leu Leu Tyr Ile Cys
1               5                   10                  15

Leu Gly Met Leu Thr Ala Tyr Leu Ala Asn Lys Lys Asn Arg Asn Leu
            20                  25                  30

Ile Gly Trp Phe Leu Ala Gly Met Phe Phe Gly Ile Phe Ala Ile Ile
        35                  40                  45

Phe Leu Leu Ile Leu Pro Pro Leu Pro Ser Ser Thr Gln Asp Asn Arg
    50                  55                  60

Ser Met Asp Gln Gln Asp Ser Glu Glu Phe Leu Leu Gln Asn Thr Leu
65                  70                  75                  80

Glu Asp Ser Glu Ile Ile Ser Ile Pro Asp Thr Met Asn Gln Ile Ala
                85                  90                  95

Ile Asp Thr Glu Lys Trp Phe Tyr Leu Asn Lys Asp Tyr Thr Asn Val
            100                 105                 110

Gly Pro Ile Ser Ile Val Gln Leu Thr Ala Phe Leu Lys Glu Cys Lys
        115                 120                 125

His Ser Pro Glu Lys Gly Ile Asp Pro Gln Glu Leu Trp Val Trp Lys
    130                 135                 140

Lys Gly Met Pro Asn Trp Glu Lys Val Lys Asn Ile Pro Glu Leu Ser
145                 150                 155                 160

Gly Thr Val Lys Asp Glu
                165

<210> SEQ ID NO 2
<211> LENGTH: 20
<212> TYPE: PRT
<213> ORGANISM: Chlamydia trachomatis

<400> SEQUENCE: 2

Lys Gly Ile Asp Pro Gln Glu Leu Trp Val Trp Lys Lys Gly Met Pro
1               5                   10                  15
```

Asn Trp Glu Lys
            20

<210> SEQ ID NO 3
<211> LENGTH: 4
<212> TYPE: PRT
<213> ORGANISM: Chlamydia trachomatis

<400> SEQUENCE: 3

Lys Gly Ile Asp
1

<210> SEQ ID NO 4
<211> LENGTH: 4
<212> TYPE: PRT
<213> ORGANISM: Chlamydia trachomatis

<400> SEQUENCE: 4

Gly Ile Asp Pro
1

<210> SEQ ID NO 5
<211> LENGTH: 4
<212> TYPE: PRT
<213> ORGANISM: Chlamydia trachomatis

<400> SEQUENCE: 5

Ile Asp Pro Gln
1

<210> SEQ ID NO 6
<211> LENGTH: 4
<212> TYPE: PRT
<213> ORGANISM: Chlamydia trachomatis

<400> SEQUENCE: 6

Asp Pro Gln Glu
1

<210> SEQ ID NO 7
<211> LENGTH: 4
<212> TYPE: PRT
<213> ORGANISM: Chlamydia trachomatis

<400> SEQUENCE: 7

Pro Gln Glu Leu
1

<210> SEQ ID NO 8
<211> LENGTH: 4
<212> TYPE: PRT
<213> ORGANISM: Chlamydia trachomatis

<400> SEQUENCE: 8

Gln Glu Leu Trp
1

<210> SEQ ID NO 9
<211> LENGTH: 4
<212> TYPE: PRT
<213> ORGANISM: Chlamydia trachomatis

<400> SEQUENCE: 9

Glu Leu Trp Val
1

```
<210> SEQ ID NO 10
<211> LENGTH: 4
<212> TYPE: PRT
<213> ORGANISM: Chlamydia trachomatis

<400> SEQUENCE: 10

Leu Trp Val Trp
1

<210> SEQ ID NO 11
<211> LENGTH: 4
<212> TYPE: PRT
<213> ORGANISM: Chlamydia trachomatis

<400> SEQUENCE: 11

Trp Val Trp Lys
1

<210> SEQ ID NO 12
<211> LENGTH: 4
<212> TYPE: PRT
<213> ORGANISM: Chlamydia trachomatis

<400> SEQUENCE: 12

Val Trp Lys Lys
1

<210> SEQ ID NO 13
<211> LENGTH: 4
<212> TYPE: PRT
<213> ORGANISM: Chlamydia trachomatis

<400> SEQUENCE: 13

Trp Lys Lys Gly
1

<210> SEQ ID NO 14
<211> LENGTH: 4
<212> TYPE: PRT
<213> ORGANISM: Chlamydia trachomatis

<400> SEQUENCE: 14

Lys Lys Gly Met
1

<210> SEQ ID NO 15
<211> LENGTH: 4
<212> TYPE: PRT
<213> ORGANISM: Chlamydia trachomatis

<400> SEQUENCE: 15

Lys Gly Met Pro
1

<210> SEQ ID NO 16
<211> LENGTH: 4
<212> TYPE: PRT
<213> ORGANISM: Chlamydia trachomatis

<400> SEQUENCE: 16

Gly Met Pro Asn
1
```

```
<210> SEQ ID NO 17
<211> LENGTH: 4
<212> TYPE: PRT
<213> ORGANISM: Chlamydia trachomatis

<400> SEQUENCE: 17

Met Pro Asn Trp
1

<210> SEQ ID NO 18
<211> LENGTH: 4
<212> TYPE: PRT
<213> ORGANISM: Chlamydia trachomatis

<400> SEQUENCE: 18

Pro Asn Trp Glu
1

<210> SEQ ID NO 19
<211> LENGTH: 4
<212> TYPE: PRT
<213> ORGANISM: Chlamydia trachomatis

<400> SEQUENCE: 19

Asn Trp Glu Lys
1

<210> SEQ ID NO 20
<211> LENGTH: 5
<212> TYPE: PRT
<213> ORGANISM: Chlamydia trachomatis

<400> SEQUENCE: 20

Lys Gly Ile Asp Pro
1               5

<210> SEQ ID NO 21
<211> LENGTH: 5
<212> TYPE: PRT
<213> ORGANISM: Chlamydia trachomatis

<400> SEQUENCE: 21

Gly Ile Asp Pro Gln
1               5

<210> SEQ ID NO 22
<211> LENGTH: 5
<212> TYPE: PRT
<213> ORGANISM: Chlamydia trachomatis

<400> SEQUENCE: 22

Ile Asp Pro Gln Glu
1               5

<210> SEQ ID NO 23
<211> LENGTH: 5
<212> TYPE: PRT
<213> ORGANISM: Chlamydia trachomatis

<400> SEQUENCE: 23

Asp Pro Gln Glu Leu
1               5

<210> SEQ ID NO 24
<211> LENGTH: 5
```

```
<212> TYPE: PRT
<213> ORGANISM: Chlamydia trachomatis

<400> SEQUENCE: 24

Pro Gln Glu Leu Trp
1               5

<210> SEQ ID NO 25
<211> LENGTH: 5
<212> TYPE: PRT
<213> ORGANISM: Chlamydia trachomatis

<400> SEQUENCE: 25

Gln Glu Leu Trp Val
1               5

<210> SEQ ID NO 26
<211> LENGTH: 5
<212> TYPE: PRT
<213> ORGANISM: Chlamydia trachomatis

<400> SEQUENCE: 26

Glu Leu Trp Val Trp
1               5

<210> SEQ ID NO 27
<211> LENGTH: 5
<212> TYPE: PRT
<213> ORGANISM: Chlamydia trachomatis

<400> SEQUENCE: 27

Leu Trp Val Trp Lys
1               5

<210> SEQ ID NO 28
<211> LENGTH: 5
<212> TYPE: PRT
<213> ORGANISM: Chlamydia trachomatis

<400> SEQUENCE: 28

Trp Val Trp Lys Lys
1               5

<210> SEQ ID NO 29
<211> LENGTH: 5
<212> TYPE: PRT
<213> ORGANISM: Chlamydia trachomatis

<400> SEQUENCE: 29

Val Trp Lys Lys Gly
1               5

<210> SEQ ID NO 30
<211> LENGTH: 5
<212> TYPE: PRT
<213> ORGANISM: Chlamydia trachomatis

<400> SEQUENCE: 30

Trp Lys Lys Gly Met
1               5

<210> SEQ ID NO 31
<211> LENGTH: 5
<212> TYPE: PRT
<213> ORGANISM: Chlamydia trachomatis
```

<400> SEQUENCE: 31

Lys Lys Gly Met Pro
1               5

<210> SEQ ID NO 32
<211> LENGTH: 5
<212> TYPE: PRT
<213> ORGANISM: Chlamydia trachomatis

<400> SEQUENCE: 32

Lys Gly Met Pro Asn
1               5

<210> SEQ ID NO 33
<211> LENGTH: 5
<212> TYPE: PRT
<213> ORGANISM: Chlamydia trachomatis

<400> SEQUENCE: 33

Gly Met Pro Asn Trp
1               5

<210> SEQ ID NO 34
<211> LENGTH: 5
<212> TYPE: PRT
<213> ORGANISM: Chlamydia trachomatis

<400> SEQUENCE: 34

Met Pro Asn Trp Glu
1               5

<210> SEQ ID NO 35
<211> LENGTH: 5
<212> TYPE: PRT
<213> ORGANISM: Chlamydia trachomatis

<400> SEQUENCE: 35

Pro Asn Trp Glu Lys
1               5

<210> SEQ ID NO 36
<211> LENGTH: 6
<212> TYPE: PRT
<213> ORGANISM: Chlamydia trachomatis

<400> SEQUENCE: 36

Lys Gly Ile Asp Pro Gln
1               5

<210> SEQ ID NO 37
<211> LENGTH: 6
<212> TYPE: PRT
<213> ORGANISM: Chlamydia trachomatis

<400> SEQUENCE: 37

Gly Ile Asp Pro Gln Glu
1               5

<210> SEQ ID NO 38
<211> LENGTH: 6
<212> TYPE: PRT
<213> ORGANISM: Chlamydia trachomatis

<400> SEQUENCE: 38

```
Ile Asp Pro Gln Glu Leu
1               5

<210> SEQ ID NO 39
<211> LENGTH: 6
<212> TYPE: PRT
<213> ORGANISM: Chlamydia trachomatis

<400> SEQUENCE: 39

Asp Pro Gln Glu Leu Trp
1               5

<210> SEQ ID NO 40
<211> LENGTH: 6
<212> TYPE: PRT
<213> ORGANISM: Chlamydia trachomatis

<400> SEQUENCE: 40

Pro Gln Glu Leu Trp Val
1               5

<210> SEQ ID NO 41
<211> LENGTH: 6
<212> TYPE: PRT
<213> ORGANISM: Chlamydia trachomatis

<400> SEQUENCE: 41

Gln Glu Leu Trp Val Trp
1               5

<210> SEQ ID NO 42
<211> LENGTH: 6
<212> TYPE: PRT
<213> ORGANISM: Chlamydia trachomatis

<400> SEQUENCE: 42

Glu Leu Trp Val Trp Lys
1               5

<210> SEQ ID NO 43
<211> LENGTH: 6
<212> TYPE: PRT
<213> ORGANISM: Chlamydia trachomatis

<400> SEQUENCE: 43

Leu Trp Val Trp Lys Lys
1               5

<210> SEQ ID NO 44
<211> LENGTH: 6
<212> TYPE: PRT
<213> ORGANISM: Chlamydia trachomatis

<400> SEQUENCE: 44

Trp Val Trp Lys Lys Gly
1               5

<210> SEQ ID NO 45
<211> LENGTH: 6
<212> TYPE: PRT
<213> ORGANISM: Chlamydia trachomatis

<400> SEQUENCE: 45

Val Trp Lys Lys Gly Met
```

```
1               5

<210> SEQ ID NO 46
<211> LENGTH: 6
<212> TYPE: PRT
<213> ORGANISM: Chlamydia trachomatis

<400> SEQUENCE: 46

Trp Lys Lys Gly Met Pro
1               5

<210> SEQ ID NO 47
<211> LENGTH: 6
<212> TYPE: PRT
<213> ORGANISM: Chlamydia trachomatis

<400> SEQUENCE: 47

Lys Lys Gly Met Pro Asn
1               5

<210> SEQ ID NO 48
<211> LENGTH: 6
<212> TYPE: PRT
<213> ORGANISM: Chlamydia trachomatis

<400> SEQUENCE: 48

Lys Gly Met Pro Asn Trp
1               5

<210> SEQ ID NO 49
<211> LENGTH: 6
<212> TYPE: PRT
<213> ORGANISM: Chlamydia trachomatis

<400> SEQUENCE: 49

Gly Met Pro Asn Trp Glu
1               5

<210> SEQ ID NO 50
<211> LENGTH: 6
<212> TYPE: PRT
<213> ORGANISM: Chlamydia trachomatis

<400> SEQUENCE: 50

Met Pro Asn Trp Glu Lys
1               5

<210> SEQ ID NO 51
<211> LENGTH: 7
<212> TYPE: PRT
<213> ORGANISM: Chlamydia trachomatis

<400> SEQUENCE: 51

Lys Gly Ile Asp Pro Gln Glu
1               5

<210> SEQ ID NO 52
<211> LENGTH: 7
<212> TYPE: PRT
<213> ORGANISM: Chlamydia trachomatis

<400> SEQUENCE: 52

Gly Ile Asp Pro Gln Glu Leu
1               5
```

<210> SEQ ID NO 53
<211> LENGTH: 7
<212> TYPE: PRT
<213> ORGANISM: Chlamydia trachomatis

<400> SEQUENCE: 53

Ile Asp Pro Gln Glu Leu Trp
1               5

<210> SEQ ID NO 54
<211> LENGTH: 7
<212> TYPE: PRT
<213> ORGANISM: Chlamydia trachomatis

<400> SEQUENCE: 54

Asp Pro Gln Glu Leu Trp Val
1               5

<210> SEQ ID NO 55
<211> LENGTH: 7
<212> TYPE: PRT
<213> ORGANISM: Chlamydia trachomatis

<400> SEQUENCE: 55

Pro Gln Glu Leu Trp Val Trp
1               5

<210> SEQ ID NO 56
<211> LENGTH: 7
<212> TYPE: PRT
<213> ORGANISM: Chlamydia trachomatis

<400> SEQUENCE: 56

Gln Glu Leu Trp Val Trp Lys
1               5

<210> SEQ ID NO 57
<211> LENGTH: 7
<212> TYPE: PRT
<213> ORGANISM: Chlamydia trachomatis

<400> SEQUENCE: 57

Glu Leu Trp Val Trp Lys Lys
1               5

<210> SEQ ID NO 58
<211> LENGTH: 7
<212> TYPE: PRT
<213> ORGANISM: Chlamydia trachomatis

<400> SEQUENCE: 58

Leu Trp Val Trp Lys Lys Gly
1               5

<210> SEQ ID NO 59
<211> LENGTH: 7
<212> TYPE: PRT
<213> ORGANISM: Chlamydia trachomatis

<400> SEQUENCE: 59

Trp Val Trp Lys Lys Gly Met
1               5

<210> SEQ ID NO 60

```
<211> LENGTH: 7
<212> TYPE: PRT
<213> ORGANISM: Chlamydia trachomatis

<400> SEQUENCE: 60

Val Trp Lys Lys Gly Met Pro
1               5

<210> SEQ ID NO 61
<211> LENGTH: 7
<212> TYPE: PRT
<213> ORGANISM: Chlamydia trachomatis

<400> SEQUENCE: 61

Trp Lys Lys Gly Met Pro Asn
1               5

<210> SEQ ID NO 62
<211> LENGTH: 7
<212> TYPE: PRT
<213> ORGANISM: Chlamydia trachomatis

<400> SEQUENCE: 62

Lys Lys Gly Met Pro Asn Trp
1               5

<210> SEQ ID NO 63
<211> LENGTH: 7
<212> TYPE: PRT
<213> ORGANISM: Chlamydia trachomatis

<400> SEQUENCE: 63

Lys Gly Met Pro Asn Trp Glu
1               5

<210> SEQ ID NO 64
<211> LENGTH: 7
<212> TYPE: PRT
<213> ORGANISM: Chlamydia trachomatis

<400> SEQUENCE: 64

Gly Met Pro Asn Trp Glu Lys
1               5

<210> SEQ ID NO 65
<211> LENGTH: 8
<212> TYPE: PRT
<213> ORGANISM: Chlamydia trachomatis

<400> SEQUENCE: 65

Lys Gly Ile Asp Pro Gln Glu Leu
1               5

<210> SEQ ID NO 66
<211> LENGTH: 8
<212> TYPE: PRT
<213> ORGANISM: Chlamydia trachomatis

<400> SEQUENCE: 66

Gly Ile Asp Pro Gln Glu Leu Trp
1               5

<210> SEQ ID NO 67
<211> LENGTH: 8
<212> TYPE: PRT
```

<213> ORGANISM: Chlamydia trachomatis

<400> SEQUENCE: 67

Ile Asp Pro Gln Glu Leu Trp Val
1               5

<210> SEQ ID NO 68
<211> LENGTH: 8
<212> TYPE: PRT
<213> ORGANISM: Chlamydia trachomatis

<400> SEQUENCE: 68

Asp Pro Gln Glu Leu Trp Val Trp
1               5

<210> SEQ ID NO 69
<211> LENGTH: 8
<212> TYPE: PRT
<213> ORGANISM: Chlamydia trachomatis

<400> SEQUENCE: 69

Pro Gln Glu Leu Trp Val Trp Lys
1               5

<210> SEQ ID NO 70
<211> LENGTH: 8
<212> TYPE: PRT
<213> ORGANISM: Chlamydia trachomatis

<400> SEQUENCE: 70

Gln Glu Leu Trp Val Trp Lys Lys
1               5

<210> SEQ ID NO 71
<211> LENGTH: 8
<212> TYPE: PRT
<213> ORGANISM: Chlamydia trachomatis

<400> SEQUENCE: 71

Glu Leu Trp Val Trp Lys Lys Gly
1               5

<210> SEQ ID NO 72
<211> LENGTH: 8
<212> TYPE: PRT
<213> ORGANISM: Chlamydia trachomatis

<400> SEQUENCE: 72

Leu Trp Val Trp Lys Lys Gly Met
1               5

<210> SEQ ID NO 73
<211> LENGTH: 8
<212> TYPE: PRT
<213> ORGANISM: Chlamydia trachomatis

<400> SEQUENCE: 73

Trp Val Trp Lys Lys Gly Met Pro
1               5

<210> SEQ ID NO 74
<211> LENGTH: 8
<212> TYPE: PRT
<213> ORGANISM: Chlamydia trachomatis

```
<400> SEQUENCE: 74

Val Trp Lys Lys Gly Met Pro Asn
1               5

<210> SEQ ID NO 75
<211> LENGTH: 8
<212> TYPE: PRT
<213> ORGANISM: Chlamydia trachomatis

<400> SEQUENCE: 75

Trp Lys Lys Gly Met Pro Asn Trp
1               5

<210> SEQ ID NO 76
<211> LENGTH: 8
<212> TYPE: PRT
<213> ORGANISM: Chlamydia trachomatis

<400> SEQUENCE: 76

Lys Lys Gly Met Pro Asn Trp Glu
1               5

<210> SEQ ID NO 77
<211> LENGTH: 8
<212> TYPE: PRT
<213> ORGANISM: Chlamydia trachomatis

<400> SEQUENCE: 77

Lys Gly Met Pro Asn Trp Glu Lys
1               5

<210> SEQ ID NO 78
<211> LENGTH: 9
<212> TYPE: PRT
<213> ORGANISM: Chlamydia trachomatis

<400> SEQUENCE: 78

Lys Gly Ile Asp Pro Gln Glu Leu Trp
1               5

<210> SEQ ID NO 79
<211> LENGTH: 9
<212> TYPE: PRT
<213> ORGANISM: Chlamydia trachomatis

<400> SEQUENCE: 79

Gly Ile Asp Pro Gln Glu Leu Trp Val
1               5

<210> SEQ ID NO 80
<211> LENGTH: 9
<212> TYPE: PRT
<213> ORGANISM: Chlamydia trachomatis

<400> SEQUENCE: 80

Ile Asp Pro Gln Glu Leu Trp Val Trp
1               5

<210> SEQ ID NO 81
<211> LENGTH: 9
<212> TYPE: PRT
<213> ORGANISM: Chlamydia trachomatis

<400> SEQUENCE: 81
```

Asp Pro Gln Glu Leu Trp Val Trp Lys
1               5

<210> SEQ ID NO 82
<211> LENGTH: 9
<212> TYPE: PRT
<213> ORGANISM: Chlamydia trachomatis

<400> SEQUENCE: 82

Pro Gln Glu Leu Trp Val Trp Lys Lys
1               5

<210> SEQ ID NO 83
<211> LENGTH: 9
<212> TYPE: PRT
<213> ORGANISM: Chlamydia trachomatis

<400> SEQUENCE: 83

Gln Glu Leu Trp Val Trp Lys Lys Gly
1               5

<210> SEQ ID NO 84
<211> LENGTH: 9
<212> TYPE: PRT
<213> ORGANISM: Chlamydia trachomatis

<400> SEQUENCE: 84

Glu Leu Trp Val Trp Lys Lys Gly Met
1               5

<210> SEQ ID NO 85
<211> LENGTH: 9
<212> TYPE: PRT
<213> ORGANISM: Chlamydia trachomatis

<400> SEQUENCE: 85

Leu Trp Val Trp Lys Lys Gly Met Pro
1               5

<210> SEQ ID NO 86
<211> LENGTH: 9
<212> TYPE: PRT
<213> ORGANISM: Chlamydia trachomatis

<400> SEQUENCE: 86

Trp Val Trp Lys Lys Gly Met Pro Asn
1               5

<210> SEQ ID NO 87
<211> LENGTH: 9
<212> TYPE: PRT
<213> ORGANISM: Chlamydia trachomatis

<400> SEQUENCE: 87

Val Trp Lys Lys Gly Met Pro Asn Trp
1               5

<210> SEQ ID NO 88
<211> LENGTH: 9
<212> TYPE: PRT
<213> ORGANISM: Chlamydia trachomatis

<400> SEQUENCE: 88

Trp Lys Lys Gly Met Pro Asn Trp Glu
1               5

```
<210> SEQ ID NO 89
<211> LENGTH: 9
<212> TYPE: PRT
<213> ORGANISM: Chlamydia trachomatis

<400> SEQUENCE: 89

Lys Lys Gly Met Pro Asn Trp Glu Lys
1               5

<210> SEQ ID NO 90
<211> LENGTH: 10
<212> TYPE: PRT
<213> ORGANISM: Chlamydia trachomatis

<400> SEQUENCE: 90

Lys Gly Ile Asp Pro Gln Glu Leu Trp Val
1               5                   10

<210> SEQ ID NO 91
<211> LENGTH: 10
<212> TYPE: PRT
<213> ORGANISM: Chlamydia trachomatis

<400> SEQUENCE: 91

Gly Ile Asp Pro Gln Glu Leu Trp Val Trp
1               5                   10

<210> SEQ ID NO 92
<211> LENGTH: 10
<212> TYPE: PRT
<213> ORGANISM: Chlamydia trachomatis

<400> SEQUENCE: 92

Ile Asp Pro Gln Glu Leu Trp Val Trp Lys
1               5                   10

<210> SEQ ID NO 93
<211> LENGTH: 10
<212> TYPE: PRT
<213> ORGANISM: Chlamydia trachomatis

<400> SEQUENCE: 93

Asp Pro Gln Glu Leu Trp Val Trp Lys Lys
1               5                   10

<210> SEQ ID NO 94
<211> LENGTH: 10
<212> TYPE: PRT
<213> ORGANISM: Chlamydia trachomatis

<400> SEQUENCE: 94

Pro Gln Glu Leu Trp Val Trp Lys Lys Gly
1               5                   10

<210> SEQ ID NO 95
<211> LENGTH: 10
<212> TYPE: PRT
<213> ORGANISM: Chlamydia trachomatis

<400> SEQUENCE: 95

Gln Glu Leu Trp Val Trp Lys Lys Gly Met
1               5                   10
```

-continued

```
<210> SEQ ID NO 96
<211> LENGTH: 10
<212> TYPE: PRT
<213> ORGANISM: Chlamydia trachomatis

<400> SEQUENCE: 96

Glu Leu Trp Val Trp Lys Lys Gly Met Pro
1               5                   10

<210> SEQ ID NO 97
<211> LENGTH: 10
<212> TYPE: PRT
<213> ORGANISM: Chlamydia trachomatis

<400> SEQUENCE: 97

Leu Trp Val Trp Lys Lys Gly Met Pro Asn
1               5                   10

<210> SEQ ID NO 98
<211> LENGTH: 10
<212> TYPE: PRT
<213> ORGANISM: Chlamydia trachomatis

<400> SEQUENCE: 98

Trp Val Trp Lys Lys Gly Met Pro Asn Trp
1               5                   10

<210> SEQ ID NO 99
<211> LENGTH: 10
<212> TYPE: PRT
<213> ORGANISM: Chlamydia trachomatis

<400> SEQUENCE: 99

Val Trp Lys Lys Gly Met Pro Asn Trp Glu
1               5                   10

<210> SEQ ID NO 100
<211> LENGTH: 10
<212> TYPE: PRT
<213> ORGANISM: Chlamydia trachomatis

<400> SEQUENCE: 100

Trp Lys Lys Gly Met Pro Asn Trp Glu Lys
1               5                   10

<210> SEQ ID NO 101
<211> LENGTH: 11
<212> TYPE: PRT
<213> ORGANISM: Chlamydia trachomatis

<400> SEQUENCE: 101

Lys Gly Ile Asp Pro Gln Glu Leu Trp Val Trp
1               5                   10

<210> SEQ ID NO 102
<211> LENGTH: 11
<212> TYPE: PRT
<213> ORGANISM: Chlamydia trachomatis

<400> SEQUENCE: 102

Gly Ile Asp Pro Gln Glu Leu Trp Val Trp Lys
1               5                   10

<210> SEQ ID NO 103
<211> LENGTH: 11
```

```
<212> TYPE: PRT
<213> ORGANISM: Chlamydia trachomatis

<400> SEQUENCE: 103

Ile Asp Pro Gln Glu Leu Trp Val Trp Lys Lys
1               5                   10

<210> SEQ ID NO 104
<211> LENGTH: 11
<212> TYPE: PRT
<213> ORGANISM: Chlamydia trachomatis

<400> SEQUENCE: 104

Asp Pro Gln Glu Leu Trp Val Trp Lys Lys Gly
1               5                   10

<210> SEQ ID NO 105
<211> LENGTH: 11
<212> TYPE: PRT
<213> ORGANISM: Chlamydia trachomatis

<400> SEQUENCE: 105

Pro Gln Glu Leu Trp Val Trp Lys Lys Gly Met
1               5                   10

<210> SEQ ID NO 106
<211> LENGTH: 11
<212> TYPE: PRT
<213> ORGANISM: Chlamydia trachomatis

<400> SEQUENCE: 106

Gln Glu Leu Trp Val Trp Lys Lys Gly Met Pro
1               5                   10

<210> SEQ ID NO 107
<211> LENGTH: 11
<212> TYPE: PRT
<213> ORGANISM: Chlamydia trachomatis

<400> SEQUENCE: 107

Glu Leu Trp Val Trp Lys Lys Gly Met Pro Asn
1               5                   10

<210> SEQ ID NO 108
<211> LENGTH: 11
<212> TYPE: PRT
<213> ORGANISM: Chlamydia trachomatis

<400> SEQUENCE: 108

Leu Trp Val Trp Lys Lys Gly Met Pro Asn Trp
1               5                   10

<210> SEQ ID NO 109
<211> LENGTH: 11
<212> TYPE: PRT
<213> ORGANISM: Chlamydia trachomatis

<400> SEQUENCE: 109

Trp Val Trp Lys Lys Gly Met Pro Asn Trp Glu
1               5                   10

<210> SEQ ID NO 110
<211> LENGTH: 11
<212> TYPE: PRT
<213> ORGANISM: Chlamydia trachomatis
```

<400> SEQUENCE: 110

Val Trp Lys Lys Gly Met Pro Asn Trp Glu Lys
1               5                   10

<210> SEQ ID NO 111
<211> LENGTH: 12
<212> TYPE: PRT
<213> ORGANISM: Chlamydia trachomatis

<400> SEQUENCE: 111

Lys Gly Ile Asp Pro Gln Glu Leu Trp Val Trp Lys
1               5                   10

<210> SEQ ID NO 112
<211> LENGTH: 12
<212> TYPE: PRT
<213> ORGANISM: Chlamydia trachomatis

<400> SEQUENCE: 112

Gly Ile Asp Pro Gln Glu Leu Trp Val Trp Lys Lys
1               5                   10

<210> SEQ ID NO 113
<211> LENGTH: 12
<212> TYPE: PRT
<213> ORGANISM: Chlamydia trachomatis

<400> SEQUENCE: 113

Ile Asp Pro Gln Glu Leu Trp Val Trp Lys Lys Gly
1               5                   10

<210> SEQ ID NO 114
<211> LENGTH: 12
<212> TYPE: PRT
<213> ORGANISM: Chlamydia trachomatis

<400> SEQUENCE: 114

Asp Pro Gln Glu Leu Trp Val Trp Lys Lys Gly Met
1               5                   10

<210> SEQ ID NO 115
<211> LENGTH: 12
<212> TYPE: PRT
<213> ORGANISM: Chlamydia trachomatis

<400> SEQUENCE: 115

Pro Gln Glu Leu Trp Val Trp Lys Lys Gly Met Pro
1               5                   10

<210> SEQ ID NO 116
<211> LENGTH: 12
<212> TYPE: PRT
<213> ORGANISM: Chlamydia trachomatis

<400> SEQUENCE: 116

Gln Glu Leu Trp Val Trp Lys Lys Gly Met Pro Asn
1               5                   10

<210> SEQ ID NO 117
<211> LENGTH: 12
<212> TYPE: PRT
<213> ORGANISM: Chlamydia trachomatis

<400> SEQUENCE: 117

```
Glu Leu Trp Val Trp Lys Lys Gly Met Pro Asn Trp
1               5                   10
```

<210> SEQ ID NO 118
<211> LENGTH: 12
<212> TYPE: PRT
<213> ORGANISM: Chlamydia trachomatis

<400> SEQUENCE: 118

```
Leu Trp Val Trp Lys Lys Gly Met Pro Asn Trp Glu
1               5                   10
```

<210> SEQ ID NO 119
<211> LENGTH: 12
<212> TYPE: PRT
<213> ORGANISM: Chlamydia trachomatis

<400> SEQUENCE: 119

```
Trp Val Trp Lys Lys Gly Met Pro Asn Trp Glu Lys
1               5                   10
```

<210> SEQ ID NO 120
<211> LENGTH: 13
<212> TYPE: PRT
<213> ORGANISM: Chlamydia trachomatis

<400> SEQUENCE: 120

```
Lys Gly Ile Asp Pro Gln Glu Leu Trp Val Trp Lys Lys
1               5                   10
```

<210> SEQ ID NO 121
<211> LENGTH: 13
<212> TYPE: PRT
<213> ORGANISM: Chlamydia trachomatis

<400> SEQUENCE: 121

```
Gly Ile Asp Pro Gln Glu Leu Trp Val Trp Lys Lys Gly
1               5                   10
```

<210> SEQ ID NO 122
<211> LENGTH: 13
<212> TYPE: PRT
<213> ORGANISM: Chlamydia trachomatis

<400> SEQUENCE: 122

```
Ile Asp Pro Gln Glu Leu Trp Val Trp Lys Lys Gly Met
1               5                   10
```

<210> SEQ ID NO 123
<211> LENGTH: 13
<212> TYPE: PRT
<213> ORGANISM: Chlamydia trachomatis

<400> SEQUENCE: 123

```
Asp Pro Gln Glu Leu Trp Val Trp Lys Lys Gly Met Pro
1               5                   10
```

<210> SEQ ID NO 124
<211> LENGTH: 13
<212> TYPE: PRT
<213> ORGANISM: Chlamydia trachomatis

<400> SEQUENCE: 124

```
Pro Gln Glu Leu Trp Val Trp Lys Lys Gly Met Pro Asn
```

<210> SEQ ID NO 125
<211> LENGTH: 13
<212> TYPE: PRT
<213> ORGANISM: Chlamydia trachomatis

<400> SEQUENCE: 125

Gln Glu Leu Trp Val Trp Lys Lys Gly Met Pro Asn Trp
1               5                   10

<210> SEQ ID NO 126
<211> LENGTH: 13
<212> TYPE: PRT
<213> ORGANISM: Chlamydia trachomatis

<400> SEQUENCE: 126

Glu Leu Trp Val Trp Lys Lys Gly Met Pro Asn Trp Glu
1               5                   10

<210> SEQ ID NO 127
<211> LENGTH: 13
<212> TYPE: PRT
<213> ORGANISM: Chlamydia trachomatis

<400> SEQUENCE: 127

Leu Trp Val Trp Lys Lys Gly Met Pro Asn Trp Glu Lys
1               5                   10

<210> SEQ ID NO 128
<211> LENGTH: 14
<212> TYPE: PRT
<213> ORGANISM: Chlamydia trachomatis

<400> SEQUENCE: 128

Lys Gly Ile Asp Pro Gln Glu Leu Trp Val Trp Lys Lys Gly
1               5                   10

<210> SEQ ID NO 129
<211> LENGTH: 14
<212> TYPE: PRT
<213> ORGANISM: Chlamydia trachomatis

<400> SEQUENCE: 129

Gly Ile Asp Pro Gln Glu Leu Trp Val Trp Lys Lys Gly Met
1               5                   10

<210> SEQ ID NO 130
<211> LENGTH: 14
<212> TYPE: PRT
<213> ORGANISM: Chlamydia trachomatis

<400> SEQUENCE: 130

Ile Asp Pro Gln Glu Leu Trp Val Trp Lys Lys Gly Met Pro
1               5                   10

<210> SEQ ID NO 131
<211> LENGTH: 14
<212> TYPE: PRT
<213> ORGANISM: Chlamydia trachomatis

<400> SEQUENCE: 131

Asp Pro Gln Glu Leu Trp Val Trp Lys Lys Gly Met Pro Asn
1               5                   10

<210> SEQ ID NO 132
<211> LENGTH: 14
<212> TYPE: PRT
<213> ORGANISM: Chlamydia trachomatis

<400> SEQUENCE: 132

Pro Gln Glu Leu Trp Val Trp Lys Lys Gly Met Pro Asn Trp
1               5                   10

<210> SEQ ID NO 133
<211> LENGTH: 14
<212> TYPE: PRT
<213> ORGANISM: Chlamydia trachomatis

<400> SEQUENCE: 133

Gln Glu Leu Trp Val Trp Lys Lys Gly Met Pro Asn Trp Glu
1               5                   10

<210> SEQ ID NO 134
<211> LENGTH: 14
<212> TYPE: PRT
<213> ORGANISM: Chlamydia trachomatis

<400> SEQUENCE: 134

Glu Leu Trp Val Trp Lys Lys Gly Met Pro Asn Trp Glu Lys
1               5                   10

<210> SEQ ID NO 135
<211> LENGTH: 15
<212> TYPE: PRT
<213> ORGANISM: Chlamydia trachomatis

<400> SEQUENCE: 135

Lys Gly Ile Asp Pro Gln Glu Leu Trp Val Trp Lys Lys Gly Met
1               5                   10                  15

<210> SEQ ID NO 136
<211> LENGTH: 15
<212> TYPE: PRT
<213> ORGANISM: Chlamydia trachomatis

<400> SEQUENCE: 136

Gly Ile Asp Pro Gln Glu Leu Trp Val Trp Lys Lys Gly Met Pro
1               5                   10                  15

<210> SEQ ID NO 137
<211> LENGTH: 15
<212> TYPE: PRT
<213> ORGANISM: Chlamydia trachomatis

<400> SEQUENCE: 137

Ile Asp Pro Gln Glu Leu Trp Val Trp Lys Lys Gly Met Pro Asn
1               5                   10                  15

<210> SEQ ID NO 138
<211> LENGTH: 15
<212> TYPE: PRT
<213> ORGANISM: Chlamydia trachomatis

<400> SEQUENCE: 138

Asp Pro Gln Glu Leu Trp Val Trp Lys Lys Gly Met Pro Asn Trp
1               5                   10                  15

<210> SEQ ID NO 139

```
<211> LENGTH: 15
<212> TYPE: PRT
<213> ORGANISM: Chlamydia trachomatis

<400> SEQUENCE: 139

Pro Gln Glu Leu Trp Val Trp Lys Lys Gly Met Pro Asn Trp Glu
1               5                   10                  15

<210> SEQ ID NO 140
<211> LENGTH: 15
<212> TYPE: PRT
<213> ORGANISM: Chlamydia trachomatis

<400> SEQUENCE: 140

Gln Glu Leu Trp Val Trp Lys Lys Gly Met Pro Asn Trp Glu Lys
1               5                   10                  15

<210> SEQ ID NO 141
<211> LENGTH: 16
<212> TYPE: PRT
<213> ORGANISM: Chlamydia trachomatis

<400> SEQUENCE: 141

Lys Gly Ile Asp Pro Gln Glu Leu Trp Val Trp Lys Lys Gly Met Pro
1               5                   10                  15

<210> SEQ ID NO 142
<211> LENGTH: 16
<212> TYPE: PRT
<213> ORGANISM: Chlamydia trachomatis

<400> SEQUENCE: 142

Gly Ile Asp Pro Gln Glu Leu Trp Val Trp Lys Lys Gly Met Pro Asn
1               5                   10                  15

<210> SEQ ID NO 143
<211> LENGTH: 16
<212> TYPE: PRT
<213> ORGANISM: Chlamydia trachomatis

<400> SEQUENCE: 143

Ile Asp Pro Gln Glu Leu Trp Val Trp Lys Lys Gly Met Pro Asn Trp
1               5                   10                  15

<210> SEQ ID NO 144
<211> LENGTH: 16
<212> TYPE: PRT
<213> ORGANISM: Chlamydia trachomatis

<400> SEQUENCE: 144

Asp Pro Gln Glu Leu Trp Val Trp Lys Lys Gly Met Pro Asn Trp Glu
1               5                   10                  15

<210> SEQ ID NO 145
<211> LENGTH: 16
<212> TYPE: PRT
<213> ORGANISM: Chlamydia trachomatis

<400> SEQUENCE: 145

Pro Gln Glu Leu Trp Val Trp Lys Lys Gly Met Pro Asn Trp Glu Lys
1               5                   10                  15

<210> SEQ ID NO 146
<211> LENGTH: 17
<212> TYPE: PRT
```

<213> ORGANISM: Chlamydia trachomatis

<400> SEQUENCE: 146

Lys Gly Ile Asp Pro Gln Glu Leu Trp Val Trp Lys Lys Gly Met Pro
1 5 10 15

Asn

<210> SEQ ID NO 147
<211> LENGTH: 17
<212> TYPE: PRT
<213> ORGANISM: Chlamydia trachomatis

<400> SEQUENCE: 147

Gly Ile Asp Pro Gln Glu Leu Trp Val Trp Lys Lys Gly Met Pro Asn
1 5 10 15

Trp

<210> SEQ ID NO 148
<211> LENGTH: 17
<212> TYPE: PRT
<213> ORGANISM: Chlamydia trachomatis

<400> SEQUENCE: 148

Ile Asp Pro Gln Glu Leu Trp Val Trp Lys Lys Gly Met Pro Asn Trp
1 5 10 15

Glu

<210> SEQ ID NO 149
<211> LENGTH: 17
<212> TYPE: PRT
<213> ORGANISM: Chlamydia trachomatis

<400> SEQUENCE: 149

Asp Pro Gln Glu Leu Trp Val Trp Lys Lys Gly Met Pro Asn Trp Glu
1 5 10 15

Lys

<210> SEQ ID NO 150
<211> LENGTH: 18
<212> TYPE: PRT
<213> ORGANISM: Chlamydia trachomatis

<400> SEQUENCE: 150

Lys Gly Ile Asp Pro Gln Glu Leu Trp Val Trp Lys Lys Gly Met Pro
1 5 10 15

Asn Trp

<210> SEQ ID NO 151
<211> LENGTH: 18
<212> TYPE: PRT
<213> ORGANISM: Chlamydia trachomatis

<400> SEQUENCE: 151

Gly Ile Asp Pro Gln Glu Leu Trp Val Trp Lys Lys Gly Met Pro Asn
1 5 10 15

Trp Glu

<210> SEQ ID NO 152
<211> LENGTH: 18
<212> TYPE: PRT
<213> ORGANISM: Chlamydia trachomatis

```
<400> SEQUENCE: 152

Ile Asp Pro Gln Glu Leu Trp Val Trp Lys Lys Gly Met Pro Asn Trp
1               5                   10                  15

Glu Lys

<210> SEQ ID NO 153
<211> LENGTH: 19
<212> TYPE: PRT
<213> ORGANISM: Chlamydia trachomatis

<400> SEQUENCE: 153

Lys Gly Ile Asp Pro Gln Glu Leu Trp Val Trp Lys Lys Gly Met Pro
1               5                   10                  15

Asn Trp Glu

<210> SEQ ID NO 154
<211> LENGTH: 19
<212> TYPE: PRT
<213> ORGANISM: Chlamydia trachomatis

<400> SEQUENCE: 154

Gly Ile Asp Pro Gln Glu Leu Trp Val Trp Lys Lys Gly Met Pro Asn
1               5                   10                  15

Trp Glu Lys

<210> SEQ ID NO 155
<211> LENGTH: 8
<212> TYPE: PRT
<213> ORGANISM: Artificial
<220> FEATURE:
<223> OTHER INFORMATION: tag

<400> SEQUENCE: 155

Ser Ile Ile Asn Phe Glu Lys Leu
1               5

<210> SEQ ID NO 156
<211> LENGTH: 20
<212> TYPE: PRT
<213> ORGANISM: Chlamydia trachomatis

<400> SEQUENCE: 156

Leu Glu Ser Thr Ser Leu Tyr Lys Lys Ala Gly Cys Ala Asn Lys Lys
1               5                   10                  15

Asn Arg Asn Leu
            20

<210> SEQ ID NO 157
<211> LENGTH: 20
<212> TYPE: PRT
<213> ORGANISM: Chlamydia trachomatis

<400> SEQUENCE: 157

Gly Cys Ala Asn Lys Lys Asn Arg Asn Leu Ile Gly Trp Phe Leu Ala
1               5                   10                  15

Gly Met Phe Phe
            20

<210> SEQ ID NO 158
<211> LENGTH: 20
<212> TYPE: PRT
```

<213> ORGANISM: Chlamydia trachomatis

<400> SEQUENCE: 158

Ile Gly Trp Phe Leu Ala Gly Met Phe Phe Gly Ile Phe Ala Ile Ile
1 5 10 15

Phe Leu Leu Ile
20

<210> SEQ ID NO 159
<211> LENGTH: 20
<212> TYPE: PRT
<213> ORGANISM: Chlamydia trachomatis

<400> SEQUENCE: 159

Gly Ile Phe Ala Ile Ile Phe Leu Leu Ile Leu Pro Pro Leu Pro Ser
1 5 10 15

Ser Thr Gln Asp
20

<210> SEQ ID NO 160
<211> LENGTH: 20
<212> TYPE: PRT
<213> ORGANISM: Chlamydia trachomatis

<400> SEQUENCE: 160

Leu Pro Pro Leu Pro Ser Ser Thr Gln Asp Asn Arg Ser Met Asp Gln
1 5 10 15

Gln Asp Ser Glu
20

<210> SEQ ID NO 161
<211> LENGTH: 20
<212> TYPE: PRT
<213> ORGANISM: Chlamydia trachomatis

<400> SEQUENCE: 161

Asn Arg Ser Met Asp Gln Gln Asp Ser Glu Glu Phe Leu Leu Gln Asn
1 5 10 15

Thr Leu Glu Asp
20

<210> SEQ ID NO 162
<211> LENGTH: 20
<212> TYPE: PRT
<213> ORGANISM: Chlamydia trachomatis

<400> SEQUENCE: 162

Glu Phe Leu Leu Gln Asn Thr Leu Glu Asp Ser Glu Ile Ile Ser Ile
1 5 10 15

Pro Asp Thr Met
20

<210> SEQ ID NO 163
<211> LENGTH: 20
<212> TYPE: PRT
<213> ORGANISM: Chlamydia trachomatis

<400> SEQUENCE: 163

Ser Glu Ile Ile Ser Ile Pro Asp Thr Met Asn Gln Ile Ala Ile Asp
1 5 10 15

Thr Glu Lys Trp
20

<210> SEQ ID NO 164
<211> LENGTH: 20
<212> TYPE: PRT
<213> ORGANISM: Chlamydia trachomatis

<400> SEQUENCE: 164

Asn Gln Ile Ala Ile Asp Thr Glu Lys Trp Phe Tyr Leu Asn Lys Asp
1               5                   10                  15

Tyr Thr Asn Val
            20

<210> SEQ ID NO 165
<211> LENGTH: 20
<212> TYPE: PRT
<213> ORGANISM: Chlamydia trachomatis

<400> SEQUENCE: 165

Phe Tyr Leu Asn Lys Asp Tyr Thr Asn Val Gly Pro Ile Ser Ile Val
1               5                   10                  15

Gln Leu Thr Ala
            20

<210> SEQ ID NO 166
<211> LENGTH: 20
<212> TYPE: PRT
<213> ORGANISM: Chlamydia trachomatis

<400> SEQUENCE: 166

Gly Pro Ile Ser Ile Val Gln Leu Thr Ala Phe Leu Lys Glu Cys Lys
1               5                   10                  15

His Ser Pro Glu
            20

<210> SEQ ID NO 167
<211> LENGTH: 20
<212> TYPE: PRT
<213> ORGANISM: Chlamydia trachomatis

<400> SEQUENCE: 167

Phe Leu Lys Glu Cys Lys His Ser Pro Glu Lys Gly Ile Asp Pro Gln
1               5                   10                  15

Glu Leu Trp Val
            20

<210> SEQ ID NO 168
<211> LENGTH: 20
<212> TYPE: PRT
<213> ORGANISM: Chlamydia trachomatis

<400> SEQUENCE: 168

Trp Lys Lys Gly Met Pro Asn Trp Glu Lys Val Lys Asn Ile Pro Glu
1               5                   10                  15

Leu Ser Gly Thr
            20

<210> SEQ ID NO 169
<211> LENGTH: 20
<212> TYPE: PRT
<213> ORGANISM: Chlamydia trachomatis

<400> SEQUENCE: 169

```
Val Lys Asn Ile Pro Glu Leu Ser Gly Thr Val Lys Asp Glu Ser Pro
1               5                   10                  15

Ser Phe Leu Val
            20

<210> SEQ ID NO 170
<211> LENGTH: 20
<212> TYPE: PRT
<213> ORGANISM: Chlamydia trachomatis

<400> SEQUENCE: 170

Val Lys Asp Glu Ser Pro Ser Phe Leu Val Gln Ser Gly Val Ala Gly
1               5                   10                  15

Leu Glu Gln Leu
            20

<210> SEQ ID NO 171
<211> LENGTH: 13
<212> TYPE: PRT
<213> ORGANISM: Chlamydia trachomatis

<400> SEQUENCE: 171

Gln Ser Gly Val Ala Gly Leu Glu Gln Leu Glu Ser Ile
1               5                   10
```